(12) United States Patent
Cortopassi et al.

(10) Patent No.: US 11,685,713 B2
(45) Date of Patent: Jun. 27, 2023

(54) SMALL MOLECULE SHC BLOCKERS USED FOR TREATING LIVER DISEASE AND METABOLIC DISEASE

(71) Applicant: Buto Corporation, Davis, CA (US)

(72) Inventors: Gino Cortopassi, Davis, CA (US);
Alexey Tomilov, Davis, CA (US);
Dmytro Kovalskyy, San Antonio, TX (US)

(73) Assignee: Buto Corporation, Davis, CA (US)

( * ) Notice: Subject to any disclaimer, the term of this patent is extended or adjusted under 35 U.S.C. 154(b) by 0 days.

(21) Appl. No.: 17/809,158

(22) Filed: Jun. 27, 2022

(65) Prior Publication Data
US 2023/0002317 A1  Jan. 5, 2023

Related U.S. Application Data

(63) Continuation of application No. PCT/US2020/067511, filed on Dec. 30, 2020.

(60) Provisional application No. 62/955,057, filed on Dec. 30, 2019.

(51) Int. Cl.
*C07D 207/20* (2006.01)
*C07D 413/12* (2006.01)

(52) U.S. Cl.
CPC ......... *C07D 207/20* (2013.01); *C07D 413/12* (2013.01)

(58) Field of Classification Search
CPC .............................. C07D 207/20; C07D 413/12
See application file for complete search history.

(56) References Cited

U.S. PATENT DOCUMENTS

2008/0287866 A1  11/2008  Heller
2019/0144447 A1   5/2019  Bhamra et al.

FOREIGN PATENT DOCUMENTS

JP           147803 B  * 11/2012
WO   WO 2018/0264442 A1    2/2018
WO   WO 2021/138450 A1     7/2021

OTHER PUBLICATIONS

PubChem SID 128227974, Deposit Date Dec. 4, 2011, pp. 1-7.
PCT/US2020/067511 International Search Report and Written Opinion dated May 20, 2021.
PCT/US2020/067511 International Preliminary Report on Patentability dated Jul. 5, 2022.

* cited by examiner

*Primary Examiner* — Samira J Jean-Louis
(74) *Attorney, Agent, or Firm* — Alston & Bird LLP

(57) ABSTRACT

The subject matter disclosed herein is directed to novel She inhibitors of Formula (II). These compounds are useful for treating impaired insulin sensitivity, glucose tolerance, obesity, diabetes, metabolic syndrome, NAFLD, NASH, PSC, PBC, or other metabolic syndrome component conditions.

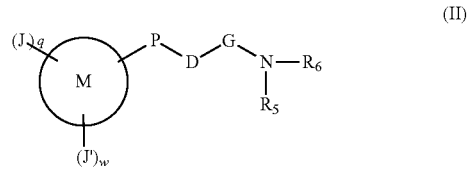

16 Claims, 4 Drawing Sheets

| Compound Information | | | | | | |
|---|---|---|---|---|---|---|
| Compound | TopAffinity | TopInsulin | Palmitate | Alcohol | Amylo | Overall |
| RTX06107454 | <1uM | Insulin 34 best | Palmitate | | Amyloid | 4 |
| RTX57548183 | <1uM | | Palmitate | Alcohol | Amyloid | 4 |
| RTX45332746 | <1uM | Insulin 34 best | Palmitate | Alcohol | | 4 |
| RTX60933293 | <1uM | Insulin 34 best | Palmitate | Alcohol | | 4 |
| RTX89483884 | <1uM | | Palmitate | Alcohol | Amyloid | 4 |
| RTX04306230 | <1uM | Insulin 34 best | Palmitate | | | 3 |
| RTX73145433 | <1uM | | Palmitate | | Amyloid | 3 |
| RTX95655369 | | | Palmitate | Alcohol | Amyloid | 3 |
| RTX26466486 | <1uM | | | Alcohol | | 2 |
| RTX70558122 | | | Palmitate | | Amyloid | 2 |
| RTX24380616 | | | Palmitate | | Amyloid | 2 |
| RTX71280707 | | | Palmitate | | Amyloid | 2 |

Fig. 2

SMALL MOLECULE SHC BLOCKERS USED FOR TREATING LIVER DISEASE AND METABOLIC DISEASE

CROSS-REFERENCE TO RELATED APPLICATIONS

This application is a continuation of International Application No. PCT/US2020/067511, filed on Dec. 30, 2020, which claims the benefit of priority to U.S. Provisional Patent Application No. 62/955,057, filed on Dec. 30, 2019, the contents of each of which are incorporated by reference herein in their entirety for all purposes.

BACKGROUND

Obesity is a well-known risk factor for the development of many common diseases, such as atherosclerosis, hypertension, type 2 diabetes (non-insulin dependent diabetes mellitus (NIDDM)), dyslipidemia, coronary heart disease, and osteoarthritis. Obesity has been shown to increase the risk of developing type 2 diabetes about ten-fold (Field et al., Arch Intern Med, 161: 1581-6 (2001). Even mild obesity increases the risk for premature death and conditions such as diabetes, dyslipidemia, hypertension, atherosclerosis, gallbladder disease and certain types of cancer. The term Metabolic Syndrome has been coined to describe a cluster of interrelated common clinical conditions, including obesity, insulin resistance, glucose intolerance, hypertension and dyslipidemia (Reaven, (1988) Diabetes 37; 1595-1607). Metabolic syndrome, its components, conditions, and sequelae are a severe and increasing health problem world-wide (Zimmet et al., Obesity, 14:1-3, 2006).

SUMMARY OF THE CLAIMED INVENTION

In certain embodiments, the subject matter described herein is directed to a compound of Formula II,

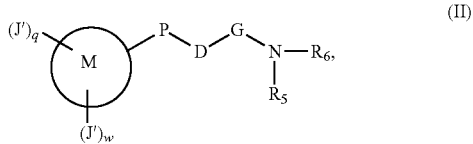

or a pharmaceutically acceptable salt thereof, wherein J, ring M, J', w, q, P, D, G, N, $R_5$, and $R_6$ are defined herein.

In certain embodiments, the subject matter described herein is directed to a pharmaceutical composition comprising a compound of Formula II and a carrier acceptable for human administration. In certain embodiments, the pharmaceutical composition is formulated for oral administration, such as in a pill or capsule. In certain embodiments, the pharmaceutical composition is formulated for parenteral administration. In certain other embodiments, the pharmaceutical composition is packaged in a vial containing a unit dose of the compound.

In certain embodiments, the subject matter described herein is directed to a method of treating or effecting prophylaxis of impaired insulin sensitivity, glucose tolerance, or obesity, comprising administering to a subject having the impaired insulin sensitivity, glucose tolerance, or obesity an effective regime of a compound of Formula II.

In certain embodiments, the subject matter described herein is directed to a method of treating a subject having non-alcoholic fatty liver disease (NAFLD), comprising administering to the subject an effective regime of a compound of Formula II.

In certain embodiments, the subject matter described herein is directed to a method of treating a subject having nonalcoholic steatohepatitis (NASH), comprising administering to the subject an effective regime of a compound of Formula II.

In certain embodiments, the subject matter described herein is directed to a method of treating a subject having primary sclerosing cholangitis (PSC), comprising administering to the subject an effective regime of a compound of Formula II.

In certain embodiments, the subject matter described herein is directed to a method of treating a subject having primary biliary cholangitis (PBC), comprising administering to the subject an effective regime of a compound of Formula II.

In certain embodiments, the subject matter described herein is directed to a method of inhibiting beta amyloid toxicity in a subject, comprising administering to a subject in need thereof an effective regime of a compound of Formula II.

Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through or perpendicular across the end of a line in a structure indicates a specified point of attachment of a group. Unless chemically or structurally required, no directionality or stereochemistry is indicated or implied by the order in which a chemical group is written or named.

The prefix "$C_u$-$C_v$" indicates that the following group has from u to v carbon atoms. For example, "$C_1$-$C_6$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±50%. In certain other embodiments, the term "about" includes the indicated amount ±20%. In certain other embodiments, the term "about" includes the indicated amount ±10%. In other embodiments, the term "about" includes the indicated amount ±5%. In certain other embodiments, the term "about" includes the indicated amount 1%. In certain other embodiments, the term "about" includes the indicated amount ±0.5% and in certain other embodiments, 0.1%. Such variations are appropriate to perform the disclosed methods or employ the disclosed compositions. Also, to the term "about x" includes description of "x". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Deuterium" as used herein alone or as part of another group, refers to a safe, non-radioactive relative of hydrogen. Any hydrogen may be replaced with deuterium to modify/improve metabolic stability, resulting in better safety, tolerability and/or efficacy.

"Alkyl" as used herein alone or as part of another group, refers to a straight or branched chain hydrocarbon containing from 1 to 10 carbon atoms, 1 to 3 carbon atoms, 1 to 6 carbon atoms, and 1 to 12 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "lower alkyl" is intended to include both substituted and unsubstituted alkyl or lower alkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heteroaryl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstitutedamino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in lower alkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "lower alkenyl" is intended to include both substituted and unsubstituted alkenyl or lower alkenyl unless otherwise indicated and these groups may be substituted with groups as described in connection with alkyl and lower alkyl above.

"Alkynyl" as used herein alone or as part of another group, refers to a straight or branched chain hydrocarbon containing from 1 to 10 carbon atoms (or in lower alkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "lower alkynyl" is intended to include both substituted and unsubstituted alkynyl or lower alkynyl unless otherwise indicated and these groups may be substituted with the same groups as set forth in connection with alkyl and lower alkyl above.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one sp$^3$ carbon atom (i.e., at least one non-aromatic ring). As used herein, cycloalkyl has from 3 to 20 ring carbon atoms (i.e., $C_3$-$C_{20}$ cycloalkyl), 3 to 12 ring carbon atoms (i.e., $C_3$-$C_{12}$ cycloalkyl), 3 to 10 ring carbon atoms (i.e., $C_3$-$C_{10}$ cycloalkyl), 3 to 8 ring carbon atoms (i.e., $C_3$-$C_8$ cycloalkyl), 3 to 7 ring carbon atoms (i.e., $C_3$-$C_7$ cycloalkyl), or 3 to 6 ring carbon atoms (i.e., $C_3$-$C_6$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Heterocyclo" or "heterocyclic group" refers to a saturated or partially unsaturated cyclic alkyl group, with one or more ring heteroatoms independently selected from nitrogen, oxygen and sulfur. The term "heterocyclo" includes heterocycloalkenyl groups (i.e., the heterocyclo group having at least one double bond), bridged-heterocyclo groups, fused-heterocyclo groups and spiro-heterocyclo groups. A heterocyclo may be a single ring or multiple rings wherein the multiple rings may be fused, bridged or spiro, and may comprise one or more (e.g., 1 to 3) oxo (=O) or N-oxide (—O$^-$) moieties. Any non-aromatic ring containing at least one heteroatom is considered a heterocyclo, regardless of the attachment (i.e., can be bound through a carbon atom or a heteroatom). Further, the term heterocyclo is intended to encompass any non-aromatic ring containing at least one heteroatom, which ring may be fused to an aryl or heteroaryl ring, regardless of the attachment to the remainder of the molecule. As used herein, heterocyclo has 2 to 20 ring carbon atoms (i.e., $C_2$-$C_{20}$ heterocyclo), 2 to 12 ring carbon atoms (i.e., $C_2$-$C_{12}$ heterocyclo), 2 to 10 ring carbon atoms (i.e., $C_2$-$C_{10}$ heterocyclo), 2 to 8 ring carbon atoms (i.e., $C_2$-$C_8$ heterocyclo), 3 to 12 ring carbon atoms (i.e., $C_3$-$C_{12}$ heterocyclo), 3 to 8 ring carbon atoms (i.e., $C_3$-$C_8$ heterocyclo), or 3 to 6 ring carbon atoms (i.e., $C_3$-$C_6$ heterocyclo); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclo groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocyclo" also includes "spiroheterocyclo" when there are two positions for substitution on the same carbon atom. Examples of the spiro-heterocyclo rings include, e.g., bicyclic and tricyclic ring systems, such as 2-oxa-7-azaspiro[3.5]nonanyl, 2-oxa-6-azaspiro[3.4]octanyl and 6-oxa-1- azaspiro[3.3]heptanyl. Examples of the fused-heterocyclo rings include, but are not limited to, 1,2,3,4-tetrahydroisoquinolinyl, 4,5,6,7-tetrahydrothieno[2,3-c]pyridinyl, indolinyl and isoindolinyl, where the heterocyclo can be bound via either ring of the fused system.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_6$-$C_{20}$ aryl), 6 to 12 carbon ring atoms (i.e., $C_6$-$C_{12}$ aryl), or 6 to 10 carbon ring atoms (i.e., $C_6$-$C_{10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl regardless of the point of attachment. If one or more aryl groups are fused with a heterocyclo, the resulting ring system is heterocyclo regardless of the point of attachment.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Cycloalkylalkyl" refers to the group "cycloalkyl-alkyl-".
"Cycloalkylalkyl" refers to the group "cycloalkyl-alkyl-".
"Alkenyloxy" refers to the group "alkenyl-o-."
"Alkynyloxy" refers to the group "alkynyl-o-."
"Cycloalkoxy" refers to the group "cycloalkyl-o-."
"Cycloalkylalkyloxy" refers to the group "cycloalkylalkyl-o-."
"Aryloxy" refers to the group "aryloxy-o-."
"Arylalkyloxy" refers to the group "arylalkyl-o-."
"Heterocyclooxy refers to the group "heterocyclo-o-."
"Heterocycloalkyloxy" refers to the group "heterocyclolalkyl-o-."
"Heteroarylalkyl" refers to the group "heteroaryl-alkyl-".
"Heterocyclolalkyl" refers to the group "heterocycloalkyl-."

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., $C_1$-$C_{20}$ heteroaryl), 3 to 12 ring carbon atoms (i.e., $C_3$-$C_{12}$ heteroaryl), or 3 to 8 carbon ring atoms (i.e., $C_3$-$C_8$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 9-10 membered ring systems (i.e., 9-10 membered heteroaryl), 5-10 membered ring systems (i.e., 5-10 membered heteroaryl), 5-7 membered ring systems (i.e., 5-7 membered heteroaryl), 5-6 membered ring systems (i.e., 5-6 membered heteroaryl), or 4-6 membered ring systems (i.e., 4-6 membered heteroaryl), each independently having 1 to 4 ring heteroatoms, 1 to 3 ring heteroatoms, 1 to 2 ring heteroatoms, or 1 ring heteroatom independently selected from nitrogen, oxygen and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Alkoxy" as used herein alone or as part of another group, refers to an alkyl or lower alkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.
"Azido" as used herein refers to an —$N_3$ group.
"Cyano" as used herein refers to a —CN group.
"Formyl" as used herein refers to a —C(O)H group.
"Carboxylic acid" as used herein refers to a —C(O)OH group.

"Hydroxyl" as used herein refers to an —OH group. In certain embodiments, "hydroxy" may also be used to refer to an —OH group.

"Hydroxyalkyl" as used herein refers to an alkyl group as defined above, wherein one or more (e.g., 1 to 6, or 1 to 3) hydrogen atoms are replaced by a hydroxy group (e.g., hydroxy-$C_1$-$C_3$-alkyl, hydroxy-$C_1$-$C_6$-alkyl). Non-limiting examples of hydroxyalkyl include —$CH_2OH$, —$CH_2CH_2OH$, and —$C(CH_3)_2CH_2OH$.

"Nitro" as used herein refers to an —$NO_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —$NH_2$.

"Alkylamino" as used herein alone or as part of another group means the radical —NHR, where R is an alkyl group.

"Alkenylamino" as used herein alone or as part of another group means the radical —NHR, where R is an alkenyl group.

"Alkynylamino" as used herein alone or as part of another group means the radical —NHR, where R is an alkynyl group.

"Haloalkylamino" as used herein alone or as part of another group means the radical —NHR, where R is a haloalkyl group.

"Arylalkylamino" as used herein alone or as part of another group means the radical —NHR, where R is an arylalkyl group.

"Cycloalkylamino" as used herein alone or as part of another group means the radical —NHR, where R is a cycloalkyl group.

"Cycloalkylalkylamino" as used herein alone or as part of another group means the radical —NHR, where R is a cycloalkylalkyl group.

"Arylamino" as used herein alone or as part of another group means the radical —NHR, where R is an aryl group.

"Arylalkylamino" as used herein alone or as part of another group means the radical —NHR, where R is an arylalkyl group.

"Heterocycloamino" as used herein alone or as part of another group means the radical —NHR, where R is a heterocyclo group.

"Heterocycloalkylamino" as used herein alone or as part of another group means the radical —NHR, where R is a heterocycloalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heteroaryl, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as amino, alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, halo, hydroxyl, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, N-tert-butoxycarbonyl (or "t-BOC") groups, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates). The polar group can be an ionic group.

"Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5, 1 to 4, or 1 to 3) hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclo, heteroaryl, and/or heteroalkyl) wherein at least one (e.g., 1 to 5, 1 to 4, or 1 to 3) hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocyclo, heterocycloalkyl, —NHNH$_2$, =NNH$_2$, imino, imido, hydroxyl, oxo, oxime, nitro, sulfonyl, sulfinyl, alkylsulfonyl, alkylsulfinyl, thiocyanate, —S(O)OH, —S(O)$_2$OH, sulfonamido, thiol, thioxo, N-oxide or —Si(R$^y$)$_3$, wherein each R$^y$ is independently hydrogen, alkyl, alkenyl, alkynyl, heteroalkyl, cycloalkyl, aryl, heteroaryl or heterocyclo.

In certain embodiments, "substituted" includes any of the above alkyl, alkenyl, alkynyl, cycloalkyl, heterocyclo, aryl or heteroaryl groups in which one or more (e.g., 1 to 5, 1 to 4, or 1 to 3) hydrogen atoms are independently replaced with deuterium, halo, cyano, nitro, azido, oxo, alkyl, alkenyl, alkynyl, haloalkyl, cycloalkyl, heterocyclo, aryl, heteroaryl, —NR$^g$R$^h$, —NR$^g$C(=O)R$^h$, —NR$^g$C(=O)NR$^g$R$^h$, —NR$^g$C(=O)OR$^h$, —NR$^g$S(=O)$_{1-2}$R$^h$, —C(=O)R$^g$, —C(=O)OR$^g$, —OC(=O)OR$^g$, —OC(=O)R$^g$, —C(=O)

NR$^g$R$^h$, —OC(=O)NR$^g$R$^h$, —OR$^g$, —SR$^g$, —S(=O)R$^g$, —S(=O)$_2$R$^g$, —OS(=O)$_{1-2}$R$^g$, —S(=O)$_{1-2}$OR$^g$, —NR$^g$S(=O)$_{1-2}$NR$^g$R$^h$, =NSO$_2$R$^g$, =NOR$^g$, —S(=O)$_{1-2}$NR$^g$R$^h$, —SF$_5$, —SCF$_3$ or —OCF$_3$. In certain embodiments, "substituted" also means any of the above groups in which one or more (e.g., 1 to 5, 1 to 4, or 1 to 3) hydrogen atoms are replaced with —C(=O)R$^g$, —C(=O)OR$^g$, —C(=O)NR$^g$R$^h$, —CH$_2$SO$_2$R$^g$, or —CH$_2$SO$_2$NR$^g$R$^h$. In the foregoing, R$^g$ and R$^h$ are the same or different and independently hydrogen, alkyl, alkenyl, alkynyl, alkoxy, thioalkyl, aryl, aralkyl, cycloalkyl, cycloalkylalkyl, haloalkyl, heterocyclo, heterocycloalkyl, heteroaryl, and/or heteroarylalkyl. In certain embodiments, "substituted" also means any of the above groups in which one or more (e.g., 1 to 5, 1 to 4, or 1 to 3) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclo, N-heterocyclo, heterocycloalkyl, heteroaryl, and/or heteroarylalkyl, or two of R$^g$ and R$^h$ and R$^i$ are taken together with the atoms to which they are attached to form a heterocyclo ring optionally substituted with oxo, halo or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to four. In certain embodiments, as used herein, the phrase "one or more" refers to one to three.

Any compound or structure given herein, is intended to represent unlabeled forms as well as isotopically labeled forms (isotopologues) of the compounds. These forms of compounds may also be referred to as and include "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Various isotopically labeled compounds of the present disclosure, for example those into which radioactive isotopes such as $^3$H, $^{13}$C and $^4$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F, $^3$H, $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium. Further, in some embodiments, the corresponding deuterated analog is provided.

In many cases, the compounds of this disclosure are capable of forming acid and/or base salts by virtue of the presence of amino and/or carboxyl groups or groups similar thereto.

Provided also are a pharmaceutically acceptable salt, isotopically enriched analog, deuterated analog, isomer (such as a stereoisomer), mixture of isomers (such as a mixture of stereoisomers), prodrug, and metabolite of the compounds described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include, e.g., hydrochloric acid, hydrobromic acid, sulfuric acid, nitric acid, phosphoric acid and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, aluminum, ammonium, calcium and magnesium salts. Salts derived from organic bases include, but are not limited to, salts of primary, secondary and tertiary amines, such as alkyl amines (i.e., $NH_2$ (alkyl)), dialkyl amines (i.e., $HN(alkyl)_2$), trialkyl amines (i.e., $N(alkyl)_3$), substituted alkyl amines (i.e., $NH_2$ (substituted alkyl)), di(substituted alkyl) amines (i.e., HN (substituted alkyl)$_2$), tri(substituted alkyl) amines (i.e., N (substituted alkyl)$_3$), alkenyl amines (i.e., $NH_2$ (alkenyl)), dialkenyl amines (i.e., HN (alkenyl)$_2$), trialkenyl amines (i.e., N (alkenyl)$_3$), substituted alkenyl amines (i.e., $NH_2$ (substituted alkenyl)), di(substituted alkenyl) amines (i.e., HN (substituted alkenyl)$_2$), tri(substituted alkenyl) amines (i.e., N (substituted alkenyl)$_3$, mono-, di- or tricycloalkyl amines (i.e., $NH_2$ (cycloalkyl), HN (cycloalkyl)$_2$, N (cycloalkyl)$_3$), mono-, di- or tri-arylamines (i.e., $NH_2$ (aryl), HN (aryl)$_2$, N (aryl)$_3$) or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxyl, amino, carboxyl, or sulfhydryl group in a compound described herein is bonded to any group that may be cleaved in vivo to regenerate the free hydroxyl, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The term, "metabolite," as used herein refers to a resulting product formed when a compound disclosed herein is metabolized. As used herein, the term "metabolized" refers to the sum of processes (including but not limited to hydrolysis reactions and reactions catalyzed by enzymes) by which a particular substance, such as a compound disclosed herein, is changed by an organism. For example, an aldehyde moiety (—C(O)H) of the compounds of the invention may be reduced in vivo to a —$CH_2OH$. A subject refers to a mammal, usually a human, but which can be a non-human primate, a domesticated mammal (e.g., a canine or a feline), an agricultural mammal (e.g., equine, bovine, ovine, porcine), or a laboratory mammal (e.g., *rattus*, murine, lagomorpha, hamster).

Treating refers to delaying the onset of, reducing, inhibiting deterioration of, or ameliorating at least one sign or symptom of a condition.

An effective regime refers to a combination of an amount, frequency of administration and route of administration effective to treat a condition.

"Metabolic syndrome" is a condition characterized by combinations of signs and symptoms of type 2 diabetes, glucose tolerance, impaired insulin sensitivity, hypertension, obesity, increased abdominal girth, hypertriglyceridemia, low HDL, hyperuricaemia, hypercoagulability and/or microalbuminemia. The International Diabetes Federation consensus worldwide definition of the metabolic syndrome (2006) is: Central obesity AND any two of the following: raised triglycerides: >150 mg/dL (1.7 mmol/L), or specific treatment for this lipid abnormality; reduced HDL cholesterol: <40 mg/dL (1.03 mmol/L) in males, <50 mg/dL (1.29 mmol/L) in females, or specific treatment for this lipid abnormality; raised blood pressure (BP): systolic BP>130 or diastolic BP>85 mm Hg, or treatment of previously diagnosed hypertension; raised fasting plasma glucose (FPG): >100 mg/dL (5.6 mmol/L), or previously diagnosed type 2 diabetes.

"Impaired insulin sensitivity" is a condition in which one or more of the body's normal physiological responses to insulin are impaired or lost. Impaired insulin sensitivity in a subject is characterized by a reduced biological response to endogenous or exogenous insulin. Impaired insulin sensitivity is associated with a number of conditions in humans, including increased risk of developing type 2 diabetes. Impaired insulin sensitivity is also a feature of metabolic syndrome, which is a cluster of abnormalities that create risk for many of our most common medial conditions. Impaired insulin sensitivity can be determined by methods such as the oral glucose tolerance test (OGTT), IV glucose tolerance test (FSIVGTT), insulin tolerance test (ITT), insulin sensitivity test (1ST), and continuous infusion of glucose with model assessment (CIGMA), or the glucose clamp. See, e.g., Krentz, Insulin Resistance (Wiley-Blackwell, 2002); de Paula Martins et al., Eur. J. Obst. Gynecol. Reprod. Biol., 133 (2):203-207. Obesity, Body Mass Index (BMI) and Visceral Adiposity.

"Diabetes" is a condition generally characterized by metabolic defects in production and utilization of glucose that result in the failure to maintain appropriate blood sugar levels in the body. The result of these defects is elevated blood glucose, referred to as "hyperglycemia." Diabetes can be defined as a condition corresponding to a fasting plasma glucose concentration greater than or equal to 126 mg/dl (6.9 mmol/l), or a plasma glucose concentration greater than or equal to 200 mg/dl (11.1 mmol/l) two hours after ingestion of a 75 g oral glucose load. Two major forms of diabetes are type 1 diabetes and type 2 diabetes. Type 1 diabetes is generally the result of an absolute deficiency of insulin, the hormone that regulates glucose utilization. Type 2 diabetes often occurs in the face of normal, or even elevated levels of insulin and can result from the inability of tissues to respond appropriately to insulin. Most Type 2 diabetic patients are insulin resistant (i.e., having impaired insulin sensitivity) and have a relative deficiency of insulin, in that insulin secretion cannot compensate for the resistance of peripheral tissues to respond to insulin. In addition, many type 2 diabetics are obese. Type 1.5 diabetes (late autoimmune onset in adults) shows some characteristics of type 1 and type 2 diabetes.

"Obese" and "obesity" are defined according to the World Health Organization, as a Body Mass Index ("BMI") greater than or equal to 30 (BMI equals weight (kg)/height (m$^2$)). Obesity is linked to a variety of medical conditions including diabetes II and hyperlipidemia. (see, e.g., Barrett-Conner E, Epidemol. Rev. (1989) 11: 172-181; and Knowler, et al., Am. J. Clin. Nutr. (1991) 53: 1543-1551).

"Abdominal obesity" is a cutoff point of waist circumference >102 cm in men and >80 cm in women, as recommended by the third report of the national cholesterol education program expert panel on detection, evaluation, and treatment of high blood cholesterol in adults (NCEP/ATP Panel III).

"Glucose tolerance" refers to a state of proper functioning of the homeostatic mechanisms by which insulin is secreted in response to an elevation in serum glucose concentrations. Impairment in this system results in transient hyperglycemia as the organism is unable to maintain normoglycemia following a glucose load (for example, a carbohydrate containing meal) because of insufficient secretion of insulin from the islet beta-cells or because of insensitivity of target tissues to circulating insulin. "Impaired glucose tolerance" can be defined as a plasma glucose concentration greater than or equal to 140 mg/dl (7.8 mmol/l) two hours after ingestion of a 75 g oral glucose load.

"Body mass index" (BMI) is s a measure of body fat. The BMI of an individual is derived in a two-step mathematical formula. The individual's weight in pounds is first multiplied by 703. The product of the first step is then divided by the square of the individual's height in inches. In a metric version, BMI is calculated as the individual's weight in kilograms divided by the square of their height in meters. BMI is a frequently used medical standard to evaluate overweight and obesity.

"Hyperglycemia" refers to an above-normal level of glucose in the blood, where a normal level is in the range of from about 65 mg/dL to about 140 mg/dL. Generally, hyperglycemia refers to a blood glucose level in excess of about 140 mg/dL.

"Dyslipidemia" refers to a condition of lipoprotein metabolism, including lipoprotein overproduction or deficiency. Dyslipidemias may be manifested by elevation of the total cholesterol, the "bad" low-density lipoprotein (LDL) cholesterol and the triglyceride concentrations, and a decrease in the "good" high-density lipoprotein (HDL) cholesterol concentration in the blood. In adult subjects dyslipidemia/hyperlipidemia is indicated when LDL cholesterol levels are more than 100 mg/dL (2.60 mmol/L), HDL cholesterol levels are equal to or lower than 40 mg/dL (1.02 mmol/L), and triglyceride levels are more than 150 mg/dL (1.7 mmol/L).

"Microalbuminuria" refers to the presence of albumin in the urine, excreted at a rate of about 20 to 200 µg/min or at a level of about 30 to 300 mg/L in humans (see, for example, Abbott, K. C., et al., Arch. Internal Med. 154: 146-153, 1994). When defined by the urinary ACR, "microalbuminuria" refers to a urinary ACR of greater than about 30 mg/g, or a urinary ACR of about 3.5 mg/mmol or greater for women and about 2.5 mg/mmol or greater for men. Methods to detect and diagnosis microalbuminuria include radioimmunoassays, immunoassays with latex bodies, fluoroimmunoassays, enzyme immunoassays, agglutination inhibition, immunoturbidimetry, immunonephelometry and radial immunodiffusion assays. (Keen, H. et al., Lancet 2: 913-916, 1968; Silver, A. et al., Clin. Chem 32: 1303-1306, 1986; Close, C. et al., Diabet. Med. 4: 491-492, 1987; Harmoinen, A. et al., Clin. Chim. Acta 166: 85-89, 1987; Marre, M. et al., Clin. Chem. 33: 209-213, 1987; McCormik, C. P. et al., Ann. Clin. Lab Sci. 19: 944-951, 1989; Cambiaso, C. L. et al., Clin. Chem. 34: 416-418, 1988; Niwa, T. et al., Clin. Chim. Acta 186: 391-396, 1990).

"Nonalcoholic fatty liver disease" or "NAFLD" refers to a condition in which fat is deposited in the liver (hepatic steatosis), with or without inflammation and fibrosis, in the absence of excessive alcohol use.

"Nonalcoholic steatohepatitis" or "NASH" refers to NAFLD in which there is inflammation and ballooning of hepatocytes with or without fibrosis in the liver. NASH may be divided into four stages. Exemplary methods of determining the stage of NASH are described, for example, in Kleiner et al., 2005, Hepatology, 41(6):1313-1321, and Brunt et al., 2007, Modern Pathol., 20: S40-S48.

A "subject having NAFLD" refers to a subject that has been diagnosed with NAFLD by a qualified medical professional as the most likely condition causing the patient's signs and symptoms. The diagnosis of NAFLD is often based on some or all of the following three criteria: zero or low-alcoholic intake, detection of steatosis either by imaging or by histology, and appropriate exclusion of other liver diseases (Hashimoto, J Gastroenterol Hepatol. 2013 December; 28 Suppl 4:64-70). In some embodiments, NAFLD is suspected during a routine checkup, monitoring of metabolic syndrome and obesity, or monitoring for possible side effects of drugs (e.g., cholesterol lowering agents or steroids). In some instance, liver enzymes such AST and ALT are high. In some embodiments, a subject is diagnosed following abdominal or thoracic imaging, liver ultrasound, or magnetic resonance imaging. In some embodiments, other conditions such as excess alcohol consumption, hepatitis C, and Wilson's disease have been ruled out prior to an NAFLD diagnosis. In some embodiments, a subject has been diagnosed following a liver biopsy.

A "subject having NASH" refers to a subject that has been diagnosed with NASH by a qualified medical professional as the most likely condition causing the patient's signs and symptoms. The diagnosis of NASH is based on similar criterion to NAFLD with differentiation being on hepatocellular morphology including steatosis and inflammation with hepatocyte ballooning with or without fibrosis. A biopsy is useful for identifying the characteristic pathology of NASH.

"Primary sclerosing cholangitis" or "PSC" refers to a chronic cholestatic condition that affects all sizes of bile ducts (Angulo, et al. Clinics in Liver Disease, 1999. 3 (3): p. 529-70; Angulo, et al. Hepatology, 1999. 30 (1): p. 325-32). As in PBC, the inflammation in PSC usually starts adjacent the biliary system resulting in cholestatic disease leading to fibrosis and cirrhosis. Up to about 80% of PSC cases are associated with inflammatory bowel disease, in particular ulcerative colitis. The disease can be complicated by the development of bile duct cancer in up to 15%. In addition, the incidence of pancreatic cancer and colonic cancer is increased relative to unaffected individuals. Diagnosis is usually based on the endoscopic retrograde cholangiography (ERC) and/or magnetic resonance cholangiography (MRC), which are showing the typical strictures and dilations in intra- and extra-hepatic bile ducts, along with the exclusion of other causes of the typical multifocal biliary strictures and intervening dilatations. On liver biopsy, periductular fibrosis with concentric layers of fibrous tissue called onion skin fibrosis can be observed. PSC is more common in men than women.

"Primary biliary cholangitis" or "PBC" is a chronic inflammatory autoimmune disease that mainly targets the cholangiocytes of the interlobular bile ducts in the liver. The condition primarily affects middle-aged women. Without treatment, PBC generally progresses to cirrhosis and eventually liver failure over a period of 10-20 years. PBC is a rare disease with prevalence of less than 1/2000. PBC is thought to result from a combination of multiple genetic factors and superimposed environmental triggers. The contribution of the genetic predisposition is evidenced by the familial clustering. Several risk factors, including exposure to infectious agents and chemical xenobiotics, have been suggested. The detection of serum antimitochondrial antibodies (AMA) and increased levels of immunoglobulin M (IgM) are biochemical features of this disease along with biochemical evidence of cholestasis with elevation of alkaline phosphatase activity. Histopathologically, it is characterized by portal inflammation and the slow progressive destruction of the portal interlobular bile ducts due to chronic non-suppurative cholangitis. The loss of bile ducts leads to cholestasis, which leads to further hepatic damage, fibrosis, cirrhosis, and ultimately, liver failure (Kaplan M, Gershwin M E. Primary biliary cirrhosis. N Engl J Med, 353, 2005, 1261-1273). There are three major forms of PBC. The typical or classical form is represented by the slowly progressive decline of small bile ducts and parallel increase in liver fibrosis, leading to biliary cirrhosis over a period of 10-20 years. A second form, which affects 10-20% of patients, is characterized by the fluctuating or persistent presence of the features of Autoimmune hepatitis (AIH) (R. Poupon Autoimmune overlapping syndromes, Clin Liver Dis, 7, 2003, pp. 865-878). These patients have a more severe disease course, with early development of liver fibrosis and liver failure. A third form, which affects 5-10% of patients, is represented by the so-called premature ductopenic variant (F. P. Vleggaar, H. R. van Buuren, P. E. Zondervan, F. J. ten Kate, W. C. Hop, Jaundice in non-cirrhotic primary biliary cirrhosis: the premature ductopenic variant, Gut, 49, 2001, 276-281). Its hallmark is a very rapid onset of ductopenia and severe icteric cholestasis, progressing very quickly towards cirrhosis in less than 5 years.

An "antagonist" is a molecule which, when bound to a target protein (such as Shc), decreases the amount (expression) or the duration of the effect of the biological or immunological activity of the target protein. Antagonists can be small molecules, proteins, nucleic acids, carbohydrates, or antibodies that decrease the amount (expression) or effect of the target protein present in the sample.

Subject at risk of a condition means subjects who by virtue of a known characteristic, such as a genetic marker, biomarker, or family history, are at significantly higher risk ($p \leq 0.05$) than a control population of individuals not known to have such genetic marker, biomarker or family history or the like of developing the condition.

A condition refers to any disease or condition characterized by abnormal sign(s) and/or symptom(s), whether caused by infection, heredity, the environment or otherwise.

Compounds are preferably provided substantially pure of contaminants arising from their production. Preferably a compound is at least 50, 90, 95 or 99% pure by weight. Purity does not exclude the presence of pharmaceutically acceptable carriers and the like intended to facilitate storage or use of a compound.

Pharmaceutically acceptable for human administration means approved or approvable by the FDA.

BRIEF DESCRIPTION OF THE FIGURES

FIG. 2 shows data for compounds examined herein. The compound information refers to the number of compounds out of 210 that exhibited biological activity under the category designated within each column (top affinity, top insulin, palmitate, alcohol, amyloid, and overall). "Top affinity" refers to compounds that exhibited binding to Shc protein having KD (equilibrium dissociation constant) values less than 1 μM. "Top insulin 34" refers to the top 34 compounds exhibiting a 2-fold change in insulin-dependent P-Akt activation over vehicle in assay screens. "Palmitate" refers to compounds that expressed 2 standard deviations different from the assay mean, and exhibited a 10% false discovery rate estimate in protection of primary hepatocyte from palmitate toxicity assays. "Alcohol" refers to compounds that expressed 2 standard deviations different from the assay mean, and had a 10% false discovery rate estimate in protection of primary hepatocyte from alcohol toxicity assays. "Amyloid" refers to compounds that expressed 2 standard deviations different form the assay mean, and had a 10% false discovery rate estimate in protection from amyloid beta toxicity in a N2A neuronal cell line assay. The number in the "Overall" column was determined by adding up the individual properties (top affinity, top insulin, palmitate, alcohol, and amyloid) for each compound.

DETAILED DESCRIPTION

I. General

Figure 1:
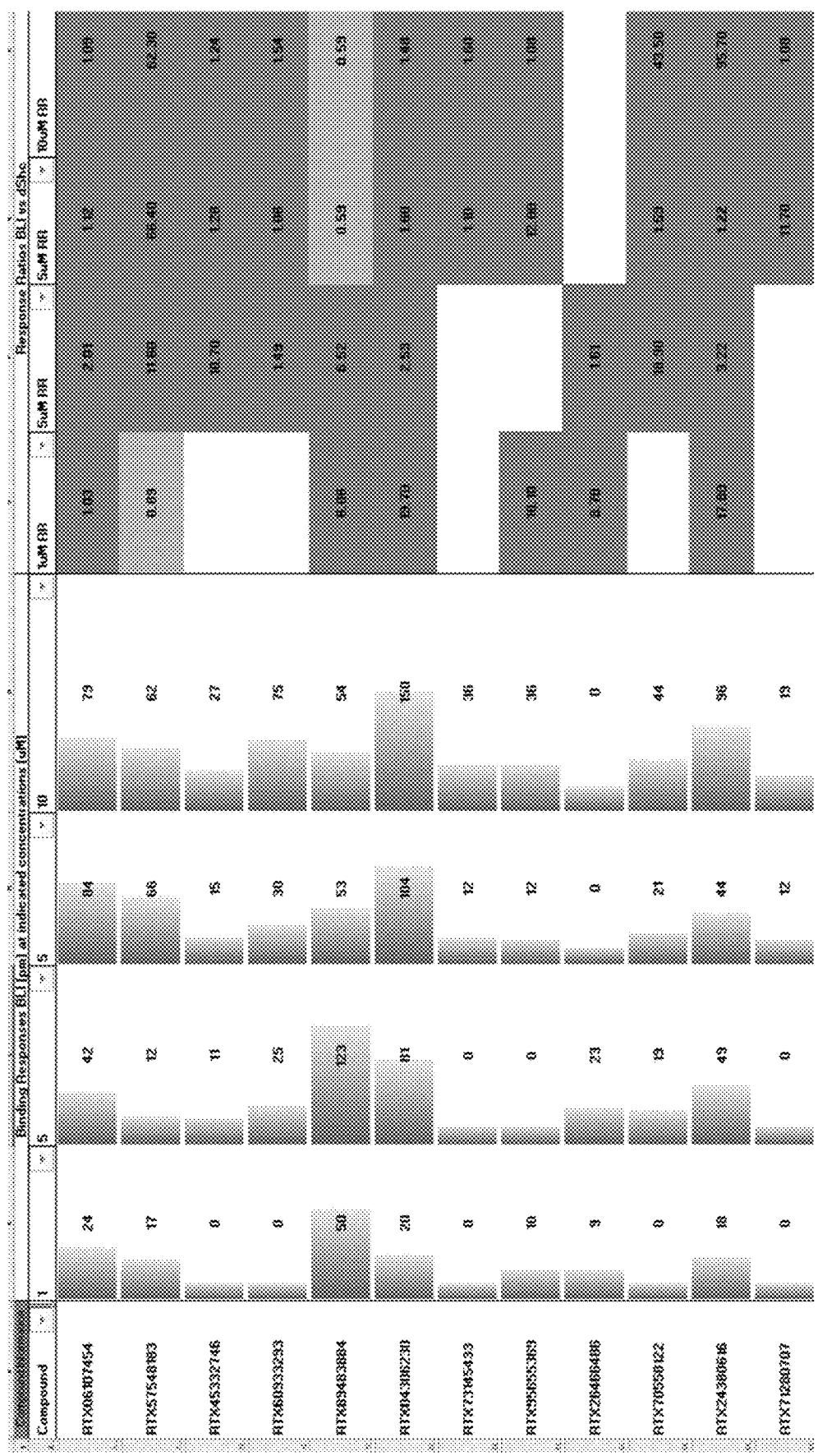
FIG. 1 shows binding response data for compounds examined herein at various concentrations and response ratios (i.e. binding of molecule to full-length Shc vs. Shc from which PTB has been deleted), by Biolayer Interferometry.

The subject matter described herein identifies novel Shc inhibitors identified by a combination of in silico screening and various bioassays. These compounds are useful for treating impaired insulin sensitivity, glucose tolerance, obesity, diabetes, metabolic syndrome, NAFLD, NASH, PSC, PBC, or other metabolic syndrome component conditions.

II. Shc Protein

Unless otherwise apparent from the context, Shc refers to human Shc-1, for which the canonical form (p66Shc) is assigned Swiss Prot P29353. Allelic variants and isoforms of the canonical form are also included. The canonical form has 583 amino acids. Residues 156-339 constitute a phosphotyrosine binding (PTB) domain. Residues 488-579 constitute a SH2 domain. At least three Shc protein isoforms including the canonical form are known to exist in mammals. These isoforms originate from alternative splicing followed by usage of alternative start codons at a single DNA locus and are p66Shc-minor, p52Shc-major (Swiss Prot P29353-2) or the metabolic isoform, and p46Shc—the mitochondrial isoform (Swiss-Prot P29353-3). P52Shc and p46Shc differ from the canonical form in omission of amino acids 1-110 and 1-155 respectively. Thus, the PTB domain runs from residues 378 to 469 in p52Shc and residues 333-424 in p46Shc.

Shc proteins are essential for insulin sensitivity and regulation of fuel selection by cells. Glucose metabolism is regulated by insulin. When sugar is not available, the cells switch on utilizing lipids, ketone bodies and proteins. Shc proteins are adaptors which interact with receptor tyrosine kinases and transmit growth signals towards induction of protein synthesis and cell division, and are known to interact with the insulin receptor by way of the phospho tyrosine binding (PTB) domain. Shc proteins also oppose metabolic insulin signaling, thus regulating fuel selection by the cell. The p52Shc isoform is preferred to identify compounds for Shc PTB domain binding because it is the most highly expressed of all Shc isoforms and is correctly folded and non-toxic in many mammalian cells lines.

III. Compounds

In certain embodiments, the subject matter described herein is directed to a compound of Formula II:

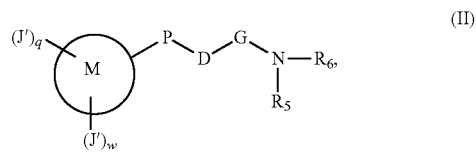

(II)

wherein,
ring M is selected from the group consisting of aryl, heteroaryl, cycloalkyl, and heterocyclo;
J and J' are each independently selected from the group consisting of halo, hydroxyl, linear or branched alkyl, alkoxy, nitro, mercapto, cyano, heterocyclo, cycloalkyl, aryl, and heteroaryl, wherein said aryl, heterocyclo, cycloalkyl, or heteroaryl is optionally substituted 1 to 3 times, in each instance, with one or a combination of alkoxy, linear or branched alkyl, halo, hydroxyl, or cyano;
w and q are each independently 0 or 1;
P is S, NH, or a bond;
D is $(CR_3R_4)_y$, wherein y is 0 or 1;
$R_3$ and $R_4$ are each hydrogen;
G is $CH_2$ or C=O;
$R_5$ is selected from the group consisting of hydrogen, linear or branched alkyl, hydroxyl, alkoxy, hydroxyalkyl, and halo; or, R₅ is taken together with the nitrogen to which it is attached and G, D, and one of R₃ and R₄ to form a heterocyclo;

R₆ is selected from the group consisting of halo, linear or branched alkyl, haloalkyl, alkenyl, alkynyl, cycloalkyl, cycloalkylalkyl, aryl, heteroaryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, —(CH₂)$_f$NHC(O)-aryl, —(CH₂)$_f$NHC(O)-heteroaryl, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, heteroaryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro, and cyano; wherein, f is 0, 1, 2, 3, 4, or 5;

m is 0, 1, 2 or 3; and said heteroaryl, aryl, heterocyclo, heterocycloalkyl, cycloalkyl, or S in —S(O)$_m$ is optionally substituted 1 to 3 times, in each instance, with one or a combination of linear or branched alkyl, —NR₅₀C(O)(CH₂)$_b$N(R₆₀R₇₀), halo, arylalkyl, aryl, hydroxyl, alkoxy, heterocycloalkyl, heteroarylalkyl, or heteroaryl; wherein, R₅₀ is hydrogen or linear or branched alkyl;

b is 0, 1, or 2;

R₆₀ and R₇₀ are each independently selected from the group consisting of hydrogen, linear or branched alkyl, halo, and haloalkyl; and wherein said heterocycloalkyl, heterocyclo, heteroarylalkyl, aryl, or heteroaryl is optionally substituted 1 to 3 times, in each instance, with one or a combination of heterocyclo, cycloalkyl, alkoxy, halo, or linear or branched alkyl; or, R₅ and R₆ are taken together with the nitrogen to which they are attached to form a heteroaryl or heterocyclo, wherein said heteroaryl or heterocyclo is optionally substituted 1 to 3 times, in each instance, with one or a combination of branched or linear alkyl, aryl, hydroxyl, haloalkoxy, hydroxyalkyl, heteroaryl, arylalkyl, heterocyclo, halo, alkoxy, —(CH₂)$_f$NHC(O)-aryl, or —(CH₂)$_f$NHC(O)-heteroaryl, wherein said heteroaryl, aryl, heterocyclo, or arylalkyl is optionally substituted 1 to 3 times, in each instance, with one or a combination of branched or linear alkyl, heterocyclo, halo, nitro, hydroxy, hydroxyalkyl, alkoxy, haloalkoxy, heteroaryl, or aryl, wherein said heteroaryl, heterocyclo, or aryl is optionally substituted 1 to 3 times, in each instance, with one or a combination of hydroxyl, aryl, branched or linear alkyl, alkoxy, haloalkoxy, or halo; or pharmaceutically acceptable salt thereof.

In certain embodiments, the subject matter described herein is directed to a compound of Formula II:

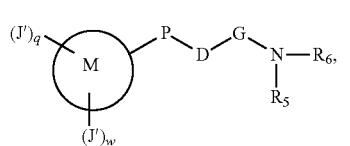

(II)

wherein ring M is selected from the group consisting of aryl, heteroaryl, cycloalkyl, and heterocyclo;

J and J' are each independently selected from the group consisting of hydrogen, halo, hydroxyl, linear or branched alkyl, alkoxy, nitro, mercapto, cyano, heterocyclo, cycloalkyl, aryl, and heteroaryl, wherein said aryl or heteroaryl is optionally substituted 1 to 3 times with alkoxy, linear or branched alkyl, halo, hydroxyl, or cyano;

w is 0 or 1

P is S, NH, or a bond;

D is (CR₃R₄)$_y$, wherein y is 0 or 1; and

R₃ and R₄ are each hydrogen;

G is CH₂ or C=O;

R₅ is selected from the group consisting of hydrogen, linear or branched alkyl, hydroxyl, alkoxy, hydroxyalkyl, and halo;

R₆ is selected from the group consisting of halo, alkyl, haloalkyl, alkenyl, alkynyl, cycloalkyl, cycloalkylalkyl, aryl, heteroaryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, —(CH₂)$_f$NHC(O)-aryl, —(CH₂)$_f$NHC(O)-heteroaryl, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heteroaryl-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano, where f=0, 1, 2, 3, 4, or 5; m=0, 1, 2 or 3, and wherein the heteroaryl, aryl, heterocyclo, or S in —S(O)$_m$ is optionally substituted 1 to 3 times with one or a combination of linear or branched alkyl, —NR₅₀C(O)(CH₂)$_b$N(R₆₀R₇₀), halo, arylalkyl, aryl, heterocyclo, heterocycloalkyl, heteroarylalkyl, or heteroaryl; wherein R₅₀ is selected from hydrogen and linear or branched alkyl;

b is 0, 1, or 2;

R₆₀ and R₇₀ are each independently selected from the group consisting of hydrogen, linear or branched alkyl, halo, and haloalkyl; and wherein said heterocyclo, heterocycloalkyl, heteroarylalkyl, aryl, or heteroaryl is optionally substituted 1 to 3 times with one or a combination of heterocyclo, halo, or linear or branched alkyl; or, wherein R₅ may be taken together with the nitrogen to which it is attached and G, D, and one of R₃ and R₄ to form a heterocyclo; or, R₅ and R₆ may be taken together with the nitrogen to which they are attached to form a heteroaryl or heterocyclo, wherein the heteroaryl or heterocyclo is optionally substituted 1 to 3 times with one or a combination of branched or linear alkyl, aryl, hydroxy, hydroxyalkyl, heteroaryl, arylalkyl, heterocyclo, halo, alkoxy, —(CH₂)$_f$NHC(O)-aryl, or —(CH₂)$_f$NHC(O)—heteroaryl, wherein said heteroaryl, heterocyclo, or arylalkyl is optionally substituted 1 to 3 times with one or a combination of branched or linear alkyl, halo, nitro, hydroxy, hydroxyalkyl, alkoxy, heteroaryl, or aryl, wherein said heteroaryl, heterocyclo, or aryl is optionally substituted 1 to 3 times with one or a combination of hydroxyl, branched or linear alkyl, haloalkoxy, or halo, or pharmaceutically acceptable salt thereof.

Useful compounds of Formula II include those where ring M is a $C_6$-$C_{12}$ aryl, 5- to 12-membered heterocyclo, or 5- to 12-membered heteroaryl, and wherein said heterocyclo or heteroaryl contains one, two, or three ring heteroatoms. Useful compounds of Formula II include those where M is selected from the group consisting of

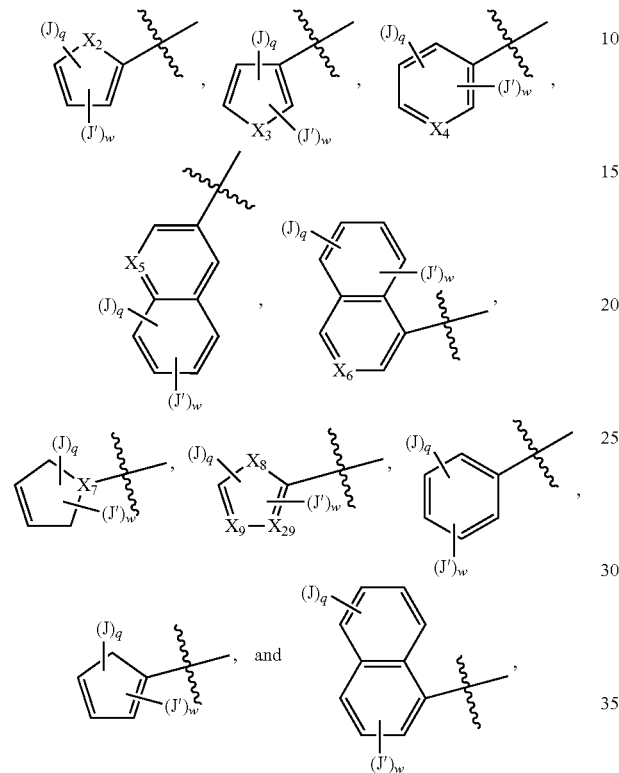

wherein $X_2$, $X_3$, $X_4$, $X_5$, $X_6$, $X_7$, $X_8$, $X_9$, and $X_{10}$ are each independently selected from the group consisting of O, N, NH, and S, where the squiggle line indicates the point of attachment to P. Useful compounds of Formula II include those where $X_4$ is N. Useful compounds of Formula II include those where $X_3$ is S. Useful compounds of Formula II include those where $X_3$ is NH. Useful compounds of Formula II include those where $X_6$ is N. Useful compounds of Formula II include those where $X_5$ is N. Useful compounds of Formula II include those where $X_7$ is N. Useful compounds of Formula II include those where $X_2$ is O. Useful compounds of Formula II include those where $X_2$ is NH. Useful compounds of Formula II include those where $X_9$ and $X_{10}$ are each N and $X_8$ is O. Useful compounds of Formula II include those where J is selected from the group consisting of hydrogen, halo, hydroxyl, and linear or branched $C_1$-$C_3$ alkyl. Useful compounds of Formula II include those where J is selected from the group consisting of halo, hydroxyl, or linear or branched $C_1$-$C_3$ alkyl. Useful compounds of Formula II include those where, wherein halo is selected from the group consisting of fluoro, chloro, and bromo. Useful compounds of Formula II include those where halo is fluoro. Useful compounds of Formula II include those where J is selected from the group consisting of methyl, fluoro, and hydroxyl. Useful compounds of Formula II include those where J' is selected from the group consisting of aryl, heteroaryl, heterocyclo, cycloalkyl, and halo, wherein said aryl or heteroaryl is optionally substituted 1 to 3 times with one or a combination of alkoxy, $C_1$-$C_3$ alkyl, halo, hydroxyl, or cyano. Useful compounds of Formula II include those where J' is alkoxy. Useful compounds of Formula II include those where J' is methoxy. Useful compounds of Formula II include those where J' is selected from the group consisting of aryl, heteroaryl, heterocyclo, cycloalkyl, and halo, wherein said aryl, heteroaryl, heterocyclo, or cycloalkyl is optionally substituted 1 to 3 times, in each instance, with alkoxy, linear or branched $C_1$-$C_3$ alkyl, halo, hydroxyl, or cyano. Useful compounds of Formula II include those where J' is selected from the group consisting of phenyl, naphthalenyl, dihydrobenzofuranyl, pyrrolyl, and pyrazolyl, optionally substituted 1 to 3 times, in each instance, with methoxy, fluoro, methyl, or cyano. Useful compounds of Formula II include those where q is 0. In other embodiments, useful compounds of Formula II include those where q is 1. Useful compounds of Formula II include those where w is 0. In other embodiments, useful compounds of Formula II include those where w is 1.

Useful compounds of Formula II include those where ring M is selected from the group consisting of

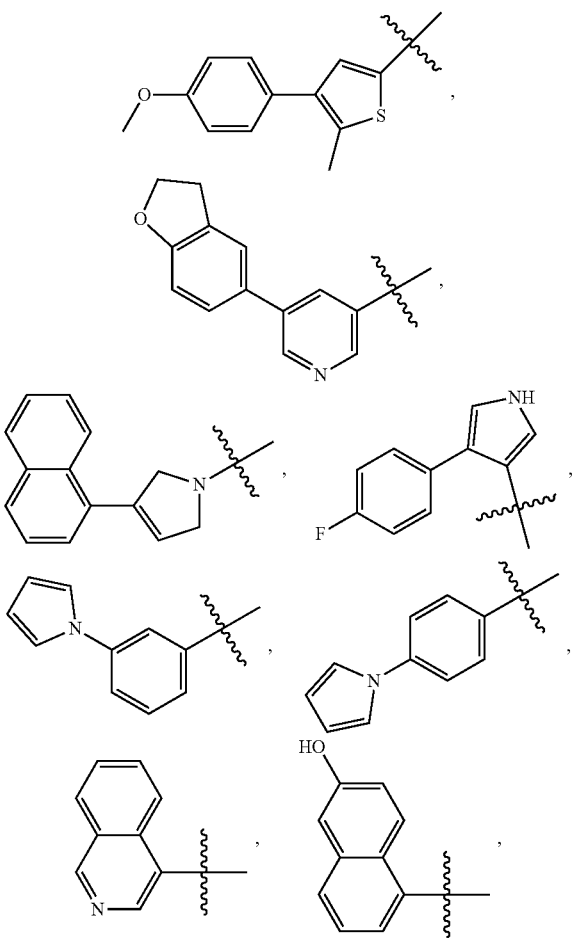

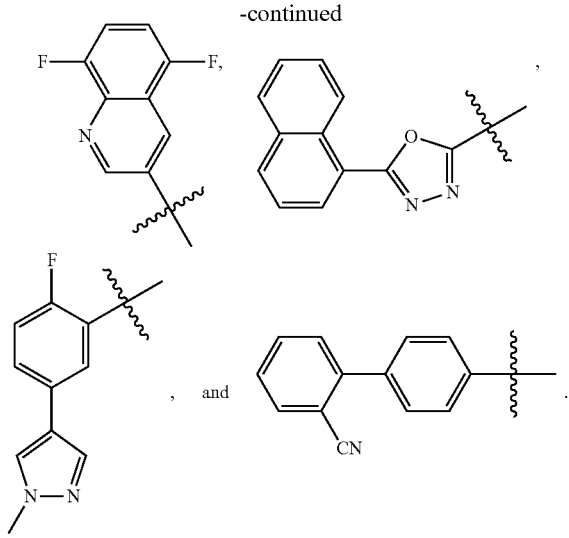

In this embodiment, both ring M and each of J and J' are depicted, if w and/or q are each 1.

Useful compounds of Formula II include those where G is C=O.

Useful compounds of Formula II include those where D is $(CR_3R_4)_y$, where $R_3$ and $R_4$ are each hydrogen. Useful compounds of Formula II include those where D is $(CR_3R_4)_y$ and y is 0.

Useful compounds of Formula II include those where P is a bond.

Useful compounds of Formula II include those where $R_5$ is selected from the group consisting of hydrogen, hydroxyl, and linear or branched $C_1$-$C_3$ alkyl. Useful compounds of Formula II include those where $R_5$ is hydrogen. Useful compounds of Formula II include those where $R_5$ is hydroxyl.

Useful compounds of Formula II include those where $R_6$ is selected from the group consisting of aryl, heteroaryl, cycloalkyl, heterocyclo, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, and heteroaryl-S(O)$_m$, wherein said aryl, heterocyclo, heteroaryl, aryl, heterocyclo, or S in —S(O)$_m$ is optionally substituted 1 to 3 times with one or a combination of linear or branched $C_1$-$C_3$ alkyl, halo, arylalkyl, aryl, or heteroaryl, and wherein said aryl or heteroaryl is optionally substituted 1 to 3 times with one or a combination of heterocyclo, halo, or linear or branched $C_1$-$C_3$ alkyl. Useful compounds of Formula II include those where $R_6$ is alkyl-S(O)$_m$, wherein S in S(O)$_m$ is optionally substituted 1 to 3 times with one or a combination of linear or branched $C_1$-$C_3$ alkyl, arylalkyl, aryl, or heteroaryl. Useful compounds of Formula II include those where m is 2. Useful compounds of Formula II include those where $R_6$ is —CH$_2$CH$_2$—S(O)$_2$, wherein S is substituted with benzyl. Useful compounds of Formula II include those where $R_6$ is selected from the group consisting of aryl, heteroaryl, and, heterocyclo, optionally substituted 1 to 3 times with one or a combination of aryl, heteroaryl, arylalkyl, —NR$_{50}$C(O) (CH$_2$)$_b$N(R$_{60}$R$_{70}$), or heterocyclo, wherein said aryl, heteroaryl, arylalkyl, or heterocyclo is optionally substituted 1 to 3 times with one or a combination of cycloalkyl, linear or branched $C_1$-$C_3$ alkyl, or halo. Useful compounds of Formula II include those where $R_6$ is phenyl, wherein said phenyl is substituted 1 to 3 times with one or a combination of aryl, heteroaryl, arylalkyl, or, heterocyclo, wherein said aryl, heteroaryl, arylalkyl, —NR$_{50}$C(O)(CH$_2$)$_b$N(R$_{60}$R$_{70}$), or heterocyclo is optionally substituted 1 to 3 times with one or a combination of cycloalkyl, linear or branched $C_1$-$C_3$ alkyl, or halo. Useful compounds of Formula II include those where $R_6$ is heteroaryl, wherein said heteroaryl is selected from the group consisting of acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl, wherein said heteroaryl is substituted 1 to 3 times with one or a combination of aryl, heteroaryl, arylalkyl, or, heterocyclo, wherein said aryl, heteroaryl, arylalkyl, or heterocyclo is optionally substituted 1 to 3 times with one or a combination of cycloalkyl, linear or branched $C_1$-$C_3$ alkyl, or halo.

Useful compounds of Formula II include those where $R_6$ is selected from the group consisting of

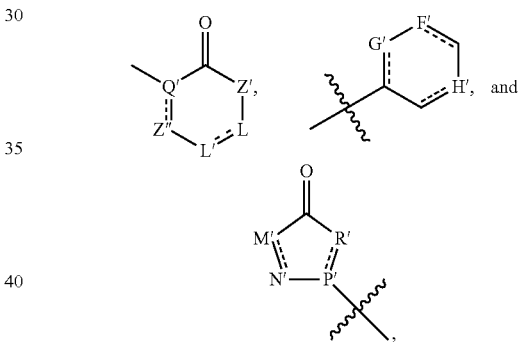

wherein the double bonds are absent or present, Q', Z", L', L, Z', G', F', H, M', N', P, and R' are each independently selected from the group consisting of N, O, S, NH, C, CH$_2$, and CH, and wherein $R_6$ is substituted 1 to 3 times with one or a combination of aryl, heteroaryl, arylalkyl, or, heterocyclo, wherein said aryl, heteroaryl, arylalkyl, or heterocyclo is optionally substituted 1 to 3 times with one or a combination of cycloalkyl, linear or branched $C_1$-$C_3$ alkyl, or halo, where the squiggle line is the point of attachment to N.

Useful compounds of Formula II include those where $R_6$ is

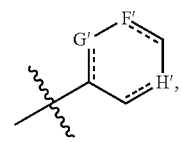

wherein G', F', and H' are each CH and the double bonds are present, and wherein $R_6$ is substituted 1 to 3 times with one or a combination of aryl, heteroaryl, arylalkyl, or, heterocyclo, wherein said aryl, heteroaryl, arylalkyl, or heterocyclo is optionally substituted 1 to 3 times with one or a combination of cycloalkyl, linear or branched $C_1$-$C_3$ alkyl, or halo.

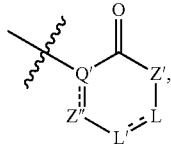

Useful compounds of Formula II include those where $R_6$ is wherein the double bonds are present, Q' is C; Z", L', L, are each CH; and Z' is N (wherein Z' is substituted), and wherein $R_6$ is substituted 1 to 3 times with one or a combination of aryl, heteroaryl, arylalkyl, or, heterocyclo, wherein said aryl, heteroaryl, arylalkyl, or heterocyclo is optionally substituted 1 to 3 times with one or a combination of cycloalkyl, linear or branched $C_1$-$C_3$ alkyl, or halo.

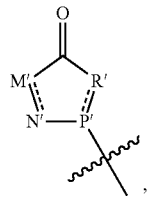

Useful compounds of Formula II include those where $R_6$ is wherein each of the double bonds is absent, M' is NH or N (wherein M' is substituted), N' is $CH_2$, P' is CH, and R' is $CH_2$, and wherein $R_6$ is substituted 1 to 3 times with one or a combination of aryl, heteroaryl, arylalkyl, or, heterocyclo, wherein said aryl, heteroaryl, arylalkyl, or heterocyclo is optionally substituted 1 to 3 times with one or a combination of cycloalkyl, linear or branched $C_1$-$C_3$ alkyl, or halo.

Useful compounds of Formula II include those where $R_6$ is substituted with a substituent selected from the group consisting of phenyl, benzyl, benzimidazolyl, benzothiazolyl, benzindolyl, benzofuranyl, benzothiazolyl, benzothiadiazolyl, furanyl, isothiazolyl, imidazolyl, indazolyl, indolyl, indazolyl, isoindolyl, isoquinolyl, isoxazolyl, naphthyridinyl, oxadiazolyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, and triazinyl, wherein said substituent is optionally substituted 1 to 3 times with one or a combination of cyclopropyl, cyclopentyl, cyclobutyl, cyclohexyl, methyl, ethyl, propyl, chloro, fluoro, bromo, methoxy, or ethoxy.

Useful compounds of Formula II include those where $R_6$ is substituted with a substituent selected from the group consisting of phenyl, benzyl, and tetrazolyl, wherein said substituent is optionally substituted 1 to 3 times with one or a combination of cyclopropyl, cyclopentyl, cyclobutyl, cyclohexyl, methyl, ethyl, propyl, chloro, fluoro, bromo, methoxy, or ethoxy.

Useful compounds of Formula II include those where $R_6$ is phenyl substituted with tetrazolyl, wherein said tetrazolyl is substituted with cyclopropyl.

Useful compounds of Formula II include those where $R_6$ is pyrrolidin-2-one, wherein said pyrrolidin-2-one is substituted with phenyl, and wherein said phenyl is substituted twice with chloro and fluoro.

Useful compounds of Formula II include those where $R_6$ is pyridin-2-one, wherein said pyridin-2-one is substituted with benzyl, and wherein said benzyl is substituted with methyl.

Useful compounds of Formula II include those where $R_5$ and $R_6$ may be taken together with the nitrogen to which they are attached to form a heteroaryl or heterocyclo, wherein the heteroaryl or heterocyclo is optionally substituted 1 to 3 times with one or a combination of branched or linear alkyl, hydroxyl, hydroxyalkyl, heteroaryl, arylalkyl, heterocyclo, halo, alkoxy, —$(CH_2)_f$NHC(O)-aryl, or —$(CH_2)_f$NHC(O)-heteroaryl, wherein said heteroaryl, heterocyclo, or arylalkyl is optionally substituted 1 to 3 times with one or a combination of branched or linear alkyl, halo, hydroxyl, hydroxyalkyl, alkoxy, heteroaryl, or aryl, wherein said heteroaryl or aryl is optionally substituted 1 to 3 times with hydroxyl, branched or linear alkyl, haloalkoxy, or halo.

Useful compounds of Formula II include those where $R_5$ and $R_6$ may be taken together with the nitrogen to which they are attached to form a 5-10-membered mono, bridged, fused, or spiro heterocyclo wherein said heterocyclo or heteroaryl contains one or two heteroatoms, and wherein said heterocyclo is optionally substituted 1 to 3 times with aryl, hydroxy, hydroxyalkyl, linear or branched $C_1$-$C_6$ alkyl, haloalkoxy, heteroaryl, heterocyclo, or —$(CH_2)_f$NHC(O)-heteroaryl, wherein f is 1, and wherein said aryl, heteroaryl, or heterocyclo is optionally substituted 1 to 3 times with haloalkoxy, halo, linear or branched $C_1$-$C_6$ alkyl.

Useful compounds of Formula II include those where $R_5$ and $R_6$ may be taken together with the nitrogen to which they are attached to form a 9-membered spiro heterocyclo, wherein said spiro heterocyclo is

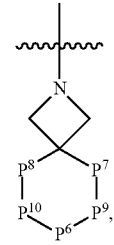

wherein $P_6$, $P_7$, $P_8$, $P_9$, and $P_{10}$ are each independently selected from the group consisting of NH O, S, and $CH_2$, wherein the squiggle line represents the point of attachment to G, and wherein the spiro heterocyclo is optionally substituted 1 to 3 times with aryl, hydroxy, hydroxyalkyl, linear or branched $C_1$-$C_6$ alkyl, haloalkoxy, heteroaryl, heterocyclo, or —$(CH_2)_f$NHC(O)-heteroaryl, wherein f is 1, and wherein said aryl, heteroaryl, or heterocyclo is optionally substituted 1 to 3 times with haloalkoxy, halo, linear or branched $C_1$-$C_6$ alkyl.

Useful compounds of Formula II include those where $P_6$ is O. In certain embodiments, $P_7$, $P_8$, $P_9$, and $P_{10}$ are each $CH_2$.

Useful compounds of Formula II include those where the spiro heterocyclo is substituted with a heterocyclo, wherein said heterocyclo is further substituted with $C_1$-$C_6$ alkyl.

Useful compounds of Formula II include those where the spiro heterocyclo is substituted with a pyrazole, wherein said pyrazole is further substituted with isobutyl.

Useful compounds of Formula II include those where $R_5$ and $R_6$ may be taken together with the nitrogen to which they are attached to form a compound selected from the group consisting of pyrrolidine, piperidine, or morpholine, wherein said pyrrolidine, piperidine, or morpholine is optionally substituted 1 to 3 times with one or a combination of aryl, hydroxy, hydroxyalkyl, linear or branched $C_1$-$C_6$ alkyl, haloalkoxy, heteroaryl, heterocyclo, or —(CH$_2$)$_f$NHC(O)-heteroaryl, wherein f is 1, and wherein said aryl, heteroaryl, or heterocyclo is optionally substituted 1 to 3 times with one or a combination of haloalkoxy, halo, and linear or branched $C_1$-$C_6$ alkyl.

Useful compounds of Formula II include those where $R_5$ and $R_6$ may be taken together with the nitrogen to which they are attached to form a pyrrolidine, wherein said pyrrolidine ring is substituted with hydroxyalkyl and benzyl, wherein said benzyl is substituted with fluoro.

Useful compounds of Formula II include those where $R_5$ and $R_6$ may be taken together with the nitrogen to which they are attached to form a pyrrolidine, wherein said pyrrolidine ring is substituted with methyl and —(CH$_2$)$_f$NHC(O)-heteroaryl, wherein f is 1 and said heteroaryl is isoquinolinyl.

Useful compounds of Formula II include those where $R_5$ and $R_6$ may be taken together with the nitrogen to which they are attached to form a pyrrolidine, wherein said pyrrolidine is substituted with isobutyl and hydroxyalkyl.

Useful compounds of Formula II include those where $R_5$ and $R_6$ may be taken together with the nitrogen to which they are attached to form a morpholine ring, wherein said morpholine ring is substituted with phenyl, and wherein said phenyl ring is substituted with haloalkoxy.

Useful compounds of Formula II include those where $R_5$ and $R_6$ may be taken together with the nitrogen to which they are attached to form a piperidine ring, wherein said piperidine ring is substituted with an imidazole ring, and wherein said imidazole ring is substituted with phenyl, and wherein said phenyl is substituted with fluoro.

Useful compounds of Formula II include those where P is S.

Useful compounds of Formula II include those where y is 1.

Useful compounds of Formula II include those where $R_5$ may be taken together with the nitrogen to which it is attached and G, D, and one of $R_3$ and $R_4$ to form a heterocyclo.

Useful compounds of Formula II include those where the heterocyclo is a 5 or 6 membered heterocyclo containing one or two heteroatoms.

Useful compounds of Formula II include those where $R_6$ is selected from the group consisting of aryl, heteroaryl, heterocyclo, and cycloalkyl, and wherein said aryl or heteroaryl is optionally substituted 1 to 3 times with one or a combination of linear or branched $C_1$-$C_3$ alkyl, hydroxyl, alkoxy, or halo.

Useful compounds of Formula II include those where $R_6$ is aryl, optionally substituted 1 to 3 times with alkoxy or hydroxyl.

Useful compounds of Formula II include those where $R_6$ is phenyl, optionally substituted 1 to 3 times with methoxy.

Useful compounds of Formula II include those where $R_6$ is phenyl substituted twice with methoxy.

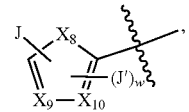

Useful compounds of Formula II include those where M is wherein $X_8$, $X_9$, and $X_{10}$ are each independently selected from N, NH, or O.

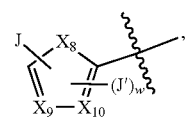

Useful compounds of Formula II include those where M is wherein $X_8$ is O and $X_9$ and $X_{10}$ are each N.

Useful compounds of Formula II include those where J is $C_6$-$C_{10}$ aryl.

Useful compounds of Formula II include those where w is 0.

Useful compounds of Formula II include those where M is aryl.

Useful compounds of Formula II include those where M is phenyl.

Useful compounds of Formula II include those where J' is selected from the group consisting of aryl, heteroaryl, heterocyclo, and cycloalkyl, wherein said aryl or heteroaryl is optionally substituted 1 to 3 times with one or a combination of alkoxy, $C_1$-$C_3$ alkyl, halo, hydroxyl, or cyano. Useful compounds of Formula II include those where J' is phenyl substituted with cyano.

Useful compounds of Formula II include those where w is 1.

Useful compounds of Formula II include those where P is a bond.

Useful compounds of Formula II include those where G is $CH_2$.

Useful compounds of Formula II include those where y is 0.

Useful compounds of Formula II include those where $R_5$ is selected from the group consisting of hydroxyalkyl, hydrogen, halo, and alkoxy. Useful compounds of Formula II include those where $R_5$ is hydroxyalkyl. Useful compounds of Formula II include those where $R_5$ is hydroxyethyl.

Useful compounds of Formula II include those where $R_6$ is selected from the group consisting of halo, linear or branched $C_1$-$C_6$ alkyl, haloalkyl, alkenyl, and alkynyl. Useful compounds of Formula II include those where $R_6$ is linear or branched $C_1$-$C_6$ alkyl. Useful compounds of Formula II include those where $R_6$ is neo-pentyl.

Useful compounds of Formula II include those selected from the group consisting of

| Compound No. | Structure |
|---|---|
| RTX57548183 (Compound 1) | 4-(4-methoxyphenyl)-N-(3-(1-cyclopropyl-1H-tetrazol-5-yl)phenyl)-5-methylthiophene-2-carboxamide |
| RTX06107454 (Compound 2) | 5-(2,3-dihydrobenzofuran-5-yl)-N-(1-(4-methylbenzyl)-2-oxo-1,2-dihydropyridin-3-yl)nicotinamide |
| RTX60933293 (Compound 3) | 3-(naphthalen-1-yl)-N-(2-(benzylsulfonyl)ethyl)-2,5-dihydro-1H-pyrrole-1-carboxamide |
| RTX26466486 (Compound 4) | 1-(4-chloro-3-fluorophenyl)-N-(4-(4-fluorophenyl)-1H-pyrrol-3-yl carboxamide)-5-oxopyrrolidin-3-yl |
| RTX73145433 (Compound 5) | (2-(3-(difluoromethoxy)phenyl)morpholino)(3-(1H-pyrrol-1-yl)phenyl)methanone |

-continued
| Compound No. | Structure |
|---|---|
| RTX45332746 (Compound 6) | 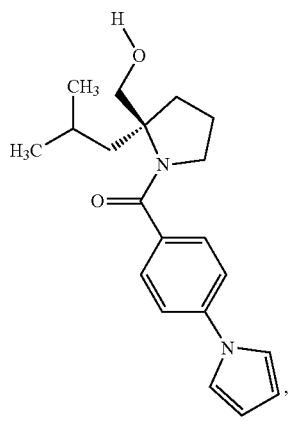 |
| RTX04306230 (Compound 7) | 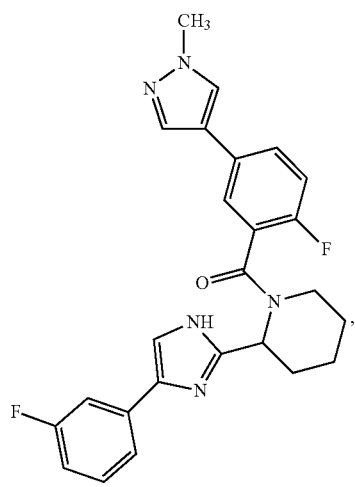 [SMILES: Cn1cc(-c2ccc(F)c(C(=O)N3CCCCC3c3nc(-c4cccc(F)c4)c[nH]3)c2)cn1] |
| RTX70558122 (Compound 8) | 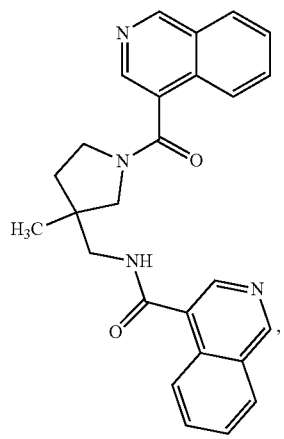 |

| Compound No. | Structure |
|---|---|
| RTX95655369 (Compound 9) | *(structure: 6-hydroxynaphthalene-1-carbonyl attached to N of a pyrrolidine bearing a hydroxymethyl and a 4-fluorobenzyl substituent)* |
| RTX71280707 (Compound 10) | *(structure: 5,8-difluoroquinoline-3-carbonyl attached to N of an azetidine spiro-linked to a tetrahydropyran, with a 1-isobutylpyrazol-4-yl substituent)* |
| RTX89483884 (Compound 11) | *(structure: 5-(naphthalen-1-yl)-1,3,4-oxadiazol-2-yl thioether linked to a 2-oxopyrrolidine N-substituted with 3,5-dimethoxyphenyl)*, and |
| RTX24380616 (Compound 12) | *(structure: 2'-cyanobiphenyl-4-ylmethyl N-substituent bearing a neopentyl group and a 2-hydroxyethyl group)*. |

The compounds bind to the PTB domain of Shc and sensitize liver cells to insulin as shown in the Examples. The compounds can also reduce insulin intolerance and related conditions in animal models, as shown in the Examples.

IV. Subjects Amenable to Treatment

Subjects amenable to treatment include individuals at risk of a condition but not showing symptoms, as well as subjects presently showing symptoms of impaired insulin sensitivity, glucose tolerance, obesity, diabetes, metabolic syndrome, NAFLD, NASH, PSC, PBC, or other metabolic syndrome component conditions. For example, the subject can be presently exhibiting symptoms of impaired insulin sensitivity, glucose tolerance, obesity, diabetes, metabolic syndrome, or other metabolic syndrome component conditions.

For example, the subject can have a body mass index of at least 30, or have body weight 30% or more above what is considered normal.

The present methods are useful for subjects who have a known genetic risk of impaired insulin sensitivity, glucose tolerance, obesity, diabetes, metabolic syndrome, NAFLD, NASH, PSC, PBC, or other metabolic syndrome component conditions, whether they are asymptomatic or showing symptoms of a condition. For example, the subject can be asymptomatic but has familial and/or genetic risk factors for developing impaired insulin sensitivity, glucose tolerance, obesity, diabetes, metabolic syndrome, or other metabolic syndrome component conditions. Such individuals include those having relatives who have experienced this condition (e.g., a parent, a grandparent, a sibling), and those whose risk is determined by analysis of genetic and/or biochemical markers. For example, such individuals include those having normal insulin sensitivity and blood glucose but a family history of diabetes or a genetic predisposition to obesity.

Genetic markers of risk toward impaired insulin sensitivity, glucose tolerance, obesity, diabetes, metabolic syndrome, or other metabolic syndrome component diseases are well-known. For example, genes that have been implicated in predisposition to obesity include UCP1 and UCP2 (whose gene products regulate body temperature), LEP (whose gene product, leptin, acts on the hypothalamus to reduce appetite and increase the body's metabolism), LEPR (leptin receptor), PCSK1 (whose gene product, proprotein convertase subtilisin/kexin type 1, processes hormone precursors such as POMC), POMC (whose gene product, among other functions, stimulates adrenal glands), MC4R (whose gene product is a melanocortin 4 receptor) and Insig2 (whose gene product regulates fatty acid and cholesterol synthesis).

Other genes, which have been associated or linked with human obesity phenotypes now number above 200. Obesity gene map databases are available on the worldwide web and genes and gene maps are described in the scientific literature (see, e.g., Perusse et al., Obesity Res. 13:381-490, 2005). Any of these factors can be taken into consideration when determining a subject's risk of obesity.

Some genes implicated in developing type 2 diabetes encode the sulfonylurea receptor (ABCC8), the calpain 10 enzyme (CAPN10), the glucagon receptor (GCGR), the enzyme glucokinase (GCK), the glucose transporter (GLUT2), the transcription factor HNF4A, the insulin hormone (INS), the insulin receptor (INSR), the potassium channel KCNJ11, the enzyme lipoprotein lipase (LPL), the transcription factor PPAR gamma, the regulatory subunit of phosphorylating enzyme (PIK3R1) and others. These genes can be evaluated when identifying a subject who may benefit from the present methods. About 18 regions of the genome have been linked with type 1 diabetes risk (see, e.g., Dean et al., "The Genetic Landscape of Diabetes," National Center for Biotechnology Information (NCBI)). These regions, each of which may contain several genes, have been labeled IDDM1 to IDDM18. The most well-studied is IDDM1, which contains the HLA genes that encode immune response proteins. There are two other non-HLA genes which have been identified thus far. One, IDDM2, is the insulin gene, and the other maps close to CTLA4, which has a regulatory role in the immune response.

The present methods are also useful in suppressing the negative sequelae associated with impaired insulin sensitivity, glucose tolerance, obesity, diabetes, metabolic syndrome, NAFLD, NASH, PSC, PBC, or other metabolic syndrome component conditions. Accordingly, patients amenable to treatment include individuals having one or more of these negative sequelae, including atherosclerosis, angina, claudication, heart attack, stroke, congestive heart failure, myocardial infarction, sleep apnea, and arthritis, vascular degeneration, macrophage proliferation and hyperactivity, plaque formation, hyperglycemia, hyper fatty acidemia, increased tumor necrosis factor and resistin levels, hypoadiponectinemia, hyper or hypo insulinemia, impaired thiol redox status (hypo-glutathione and cysteine-emia), PPARγ inactivity, and mitochondrial energy uncoupling with elevated $H_2O_2$, OHOO, cytoplasmic cytochrome c, high blood pressure, high blood cholesterol, dyslipidemia, hyperlipidemia, dyslipidemia, atherosclerotic condition including stroke, coronary artery condition or myocardial infarction, hyperinsulinemia and/or hyperproinsulinemia, microalbuminuria, delayed insulin release, diabetic complications, including coronary heart condition, angina pectoris, congestive heart failure, stroke, cognitive functions in dementia, retinopathy, peripheral neuropathy, nephropathy, glomerulonephritis, glomerulosclerosis, nephrotic syndrome, hypertensive enephrosclerosis, some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related conditions, such as gallstones, cholecystitis and cholelithiasis, gout, obstructive sleep apnea and respiratory problems, osteoarthritis, and prevention and treatment of bone loss, e.g. osteoporosis.

Patients amenable to treatment include also individuals undergoing premature aging (e.g., biological age greater than chronological age), or even individuals undergoing normal aging (biological age equal to chronological age) with a view to slowing the aging process.

Some subjects are free of a condition treatable with the compounds other than the conditions disclosed herein (e.g., diabetes, obesity, metabolic syndrome and its components, or premature aging).

V. General Procedures for Preparing Compounds of Formula II

Compounds can be synthesized by synthetic routes that include processes analogous to those well-known in the chemical arts, particularly in light of the description contained herein, and those for other compounds described in: Comprehensive Heterocyclic Chemistry II, Editors Katritzky and Rees, Elsevier, 1997, e.g., Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database). DTT refers to dithiothreitol. DHAA refers to dehydroascorbic acid.

Synthetic chemistry transformations and protecting group methodologies (protection and deprotection) useful in synthesizing compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3$^{rd}$ Ed., John Wiley and Sons (1999); and L. Paquette, ed., Encyclopedia of Reagents for Organic Synthesis, John Wiley and Sons (1995) and subsequent editions thereof.

Compounds may be prepared singly or as compound libraries comprising at least 2, for example 5 to 1,000 compounds, or 10 to 100 compounds. Libraries of compounds of Formula II may be prepared by a combinatorial 'split and mix' approach or by multiple parallel syntheses using either solution phase or solid phase chemistry, by procedures known to those skilled in the art. Thus, according to a further aspect, there is provided a compound library comprising at least 2 compounds, or pharmaceutically acceptable salts thereof.

The General Procedures and Examples provide exemplary methods for preparing compounds. Those skilled in the art will appreciate that other synthetic routes may be used to synthesize the compounds. Although specific starting materials and reagents are depicted and discussed in the Schemes, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

VI. Methods of Treatment and Prophylaxis

The subject may already exhibit symptoms of a condition or be diagnosed as having impaired insulin sensitivity, glucose tolerance, obesity, diabetes, metabolic syndrome, NAFLD, NASH, PSC, PBC, or other metabolic syndrome component condition. In such subjects, administration of the present compounds can reverse or delay progression of and or reduce the severity of symptoms.

The effectiveness of treatment can be determined by comparing a baseline measure of a parameter of a condition before administration of the present compounds is commenced to the same parameter one or more time points after the present compounds has been administered. The parameter of a condition can be one or more of the signs or symptoms of impaired insulin sensitivity, glucose tolerance, obesity, diabetes, metabolic syndrome, NAFLD, NASH, PSC, PBC, or other metabolic syndrome component conditions described herein. Measurement of a level of various biomarkers described herein in response to treatment can indicate that treatment is effective.

In certain embodiments, the compounds of Formula II are useful in the prophylactic or therapeutic treatment of amyloidogenic diseases and conditions that are characterized by the presence of deposits of amyloid proteins, such as amylin or Aβ peptide. Such diseases include, but are not limited to, Alzheimer's disease, Down's syndrome and cognitive impairment, type II diabetes, Parkinson's disease, amyloidoses such as hereditary or systemic amyloidoses, and diseases caused all or in part by prion infection. In certain embodiments, the subject matter described herein is directed to a method of inhibiting beta amyloid toxicity in a subject, comprising administering to a subject in need thereof an effective regime of a compound of Formula II. In certain embodiments, the subject matter described herein is directed to a method of treating an amyloid-β related disease in a subject, comprising administering to a subject in need thereof an effective regime of a compound of Formula II. In certain embodiments, the amyloid-β related disease is Alzheimer's disease.

For the purposes of prophylaxis, the subject may be asymptomatic, but have one or more risk factors (genetic or non-genetic) described herein. For example, subjects may be asymptomatic but judged to be at high risk based on genetic tests, or other predictive tests. Alternatively, the subject may be exhibiting symptoms of early stages of a condition. In such subjects, administration of one of the present compounds can inhibit or delay onset or progression of conditions into later stages of conditions, and/or reduce the severity of the condition once present.

Measurable parameters for evaluating the effectiveness of the prevention regime are as discussed herein for therapy and monitoring.

VII. Formulation and Administration of Compounds a. Formulation

The compounds described herein or pharmaceutically acceptable salts thereof can be administered orally, parenterally, (intravenously (IV), intramuscularly (IM), depo-IM, subcutaneously (SQ), and depo-SQ), sublingually, intranasally (e.g., inhalation, nasal mist or drops), intrathecally, topically, transmucosally, bucally, sublingually, ionophoretically or rectally.

Compositions are provided that contain therapeutically effective amounts of one of the present compounds. The compounds are preferably formulated into suitable pharmaceutical preparations such as tablets, capsules, or elixirs for oral administration or in sterile solutions or suspensions for parenteral administration.

The present compounds can be administered in the "native" form or, if desired, in the form of pharmaceutically acceptable salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the compounds can be prepared using standard procedures described, for example, by March (1992) Advanced Organic Chemistry; Reactions, Mechanisms and Structure, 4th Ed. N.Y. Wiley-Interscience. Prodrugs of the compounds readily undergo chemical changes under physiological conditions to provide the compounds of the present invention. Conversion usually occurs after administration to a subject.

Such derivatives can be formulated by conventional methods. For example, the disulfide salts of a number of delivery agents are described in WO 2000/059863 which is incorporated herein by reference. Similarly, acid salts of compounds can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include to both organic acids, e.g., acetic acid, carboxylic acid, propionic acid, glycolic acid, pyruvic acid, oxalic acid, malic acid, malonic acid, succinic acid, suberic acid, lactic acid, benzene sulfonic acid, p-tolylsulfonic acid, arginine, glucuronic acid, galactunoric acid phthalic acid, maleic acid, fumaric acid, tartaric acid, citric acid, benzoic acid, cinnamic acid isobutyric, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like (see, e.g., Berge et al., J. Pharm. Sci. 66, 1-19 (1977).

Although compounds can be supplied in the form of an HCl salt, acid salts with weaker acids (e.g., pKa 1-6-9 or preferably pKa 4-6.5) are preferred for parenteral administration. An acid addition salt can be reconverted to the free base by treatment with a suitable base. Preferred acid addition salts include halide salts, such as may be prepared using hydrochloric or hydrobromic acids. Basic salts of the compounds of this invention are prepared in a similar manner using a pharmaceutically acceptable base such as sodium hydroxide, potassium hydroxide, ammonium hydroxide, calcium hydroxide, trimethylamine, or the like. For example, basic salts can include alkali metal salts, e.g., the sodium salt, and copper salts.

For the preparation of salt forms of basic drugs, the pKa of the counterion is preferably at least about 2 pH lower than the pKa of the drug. Similarly, for the preparation of salt forms of acidic drugs, the pKa of the counterion is preferably at least about 2 pH higher than the pKa of the drug. This permits the counterion to bring the solution's pH to a level lower than the pHmax to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include acetate, benzoate, besylate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like. Suitable cationic salt forms include aluminum, benzathine, calcium, ethylene diamine, lysine, magnesium, meglumine, potassium, procaine, sodium, tromethamine, zinc, and the like.

Preparation of esters can typically involve functionalization of hydroxyl and/or carboxyl groups that are present within the molecular structure of the compound. For example, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques described in the pertinent literature. For example, amides may be prepared from esters, using suitable amine reactants, or they may be prepared from an anhydride or an acid chloride by reaction with ammonia or a lower alkyl amine.

About 1 to 1000 mg of a compound is compounded with a physiologically acceptable vehicle, carrier, excipient, binder, preservative, stabilizer, flavor, and so forth, in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 1-1000 mg, 2-800 mg, 5-500 mg, 10-400 mg, 50-200 mg, e.g., about 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 200 mg, 300 mg, 400 mg, 500 mg, 600 mg, 700 mg, 800 mg, 900 mg or 1000 mg of the active ingredient. The term "unit dosage from" refers to physically discrete units suitable as unitary (i.e., single) dosages for human subjects and other mammals, each unit containing a predetermined quantity of active material calculated to produce the desired therapeutic effect, in association with a suitable pharmaceutical excipient.

To prepare compositions, the one or more compounds is mixed with a suitable pharmaceutically acceptable carrier. On mixing or addition of the compound(s), the resulting mixture may be a solution, suspension, emulsion, or the like. Liposomal suspensions may also be suitable as pharmaceutically acceptable carriers. The form of the resulting mixture depends upon a number of factors, including the intended mode of administration and the solubility of the compound in the selected carrier or vehicle. The effective concentration is sufficient for lessening or ameliorating at least one symptom of the condition may be empirically determined.

Pharmaceutical carriers or vehicles suitable for administration of the compounds provided herein include any such carriers known to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods include, using cosolvents such as dimethylsulfoxide (DMSO), using surfactants such as Tween™, and dissolution in aqueous sodium bicarbonate. Derivatives of the compounds, such as salts or prodrugs may also be used in formulating effective pharmaceutical compositions.

The concentration of the one or more compounds is effective for delivery of an amount upon administration that lessens or ameliorates at least one symptom of the condition for which the compound is administered and/or that is effective in a prophylactic context. Typically, the compositions are formulated for single dosage (e.g., daily) administration.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated condition. A therapeutically or prophylactically effective dose can be determined by first administering a low dose, and then incrementally increasing until a dose is reached that achieves the desired effect with minimal or no undesired side effects.

The compounds described herein, derivatives and/or pharmaceutically acceptable salts thereof can be enclosed in multiple or single dose containers. The enclosed compounds and compositions can be provided in kits, for example, including component parts that can be assembled for use. For example, a compound in lyophilized form and a suitable diluent may be provided as separated components for combination prior to use. A kit may include an compound and a second therapeutic compound for co-administration. The compound and the second therapeutic compound may be provided as separate component parts. A kit may include a plurality of containers, each container holding one or more unit dose of the one or more active compounds. The containers are preferably adapted for the desired mode of administration, including to tablets, gel capsules, sustained-release capsules, and the like for oral administration; depot products, pre-filled syringes, ampules, vials, and the like for parenteral administration; and patches, medipads, creams, and the like for topical or transdermal administration. Optionally, such containers contain a unit dose for single administration.

The concentration and/or amount of active compound in the drug composition depend on absorption, inactivation, and excretion rates of the active compound, the dosage schedule, and amount administered as well as other factors.

The active ingredient may be administered at once, or may be divided into a number of smaller doses to be administered at intervals of time. The precise dosage and duration of treatment is a function of the condition being treated and may be determined empirically using known testing protocols or by extrapolation from in vivo or in vitro test data. Concentrations and dosage values may also vary with the severity of the condition to be alleviated. For any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be provided in a formulation that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, gum tragacanth, acacia, corn starch, or gelatin; an excipient such as microcrystalline cellulose, starch, or lactose; a disintegrating agent such as, alginic acid and corn starch; a lubricant such as magnesium stearate; a glidant, such as, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, medicated chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Suitable carriers for intravenous administration include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The present compounds may be prepared with carriers that protect them against rapid elimination from the body, such as time-release formulations or coatings. Controlled release is a mechanism of formulation to release a drug over an extended time. Use of controlled release formulation may reduce the frequency of administration, reduce fluctuations in blood concentration and protect the gastrointestinal tract from side effects. The active compounds may be prepared with carriers that protect the compound against rapid elimination from the body, such as time-release formulations or coating. Such carriers include controlled release formulations (also known as modified, delayed, extended or sustained release or gastric retention dosage forms, such as the Depomed GR™ system in which agents are encapsulated by polymers that swell in the stomach and are retained for about eight hours, sufficient for daily dosing of many drugs). Controlled release systems include microencapsulated delivery systems, implants and biodegradable, biocompatible polymers such as collagen, ethylene vinyl acetate, polyanhydrides, polyglycolic acid, polyorthoesters, polylactic acid, matrix controlled release devices, osmotic controlled release devices, multiparticulate controlled release devices, ion-exchange resins, enteric coatings, multilayered coatings, microspheres, liposomes, and combinations thereof. The release rate of the active ingredient can also be modified by varying the particle size of the active ingredient(s). Examples of modified release include, e.g., those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

b) Route of Administration and Dosing

The compounds can be administered orally, parenterally (IV, IM, depo-IM, SQ, and depo-SQ), sublingually, intranasally (inhalation), intraspinally, intrathecally, topically, or rectally.

The compounds can be administered enterally or parenterally. Oral formulations include tablets and capsules as well as liquid dosage forms such as solutions, suspensions, and elixirs. When the solid dosage forms are used, it is preferred that they be of the sustained release type so that the one or more active agents need to be administered only once or twice daily (or less frequency).

The oral dosage forms can be administered to the patient 1, 2, 3, or 4 times daily or less frequently, such as on alternate days, every third day, twice a week or once a week. It is preferred that the one or more active agents be administered either three or fewer times, more preferably once or twice daily. Oral dosage forms are preferably designed so as to protect the one or more active agents from the acidic environment of the stomach, such as by enteric coated or by use of capsules filled with small spheres each coated to protect from the acidic stomach.

When administered orally, an administered amount therapeutically effective to prevent, mitigate or treat impaired insulin sensitivity, glucose tolerance, obesity, diabetes, aging, metabolic syndrome, or other metabolic syndrome component conditions is from about 0.1 mg/day to about 200 mg/day, for example, from about 1 mg/day to about 100 mg/day, for example, from about 5 mg/day to about 50 mg/day. The subject can be administered a compound at a dose of about 0.05 to about 0.50 mg/kg or 0.1 mg/kg-10 mg/kg or 0.5 mg/kg to 5 mg/kg, for example, about 0.05 mg/kg, 0.10 mg/kg, 0.20 mg/kg, 0.33 mg/kg, 0.50 mg/kg, 1 mg/kg, 5 mg/kg or 10 mg/kg. Although a patient may be started at one dose, that dose may be varied (increased or decreased, as appropriate) over time as the patient's condition changes. Depending on outcome evaluations, higher doses may be used. For example, in certain subjects, up to as much as 1000 mg/day can be administered, e.g., 200 mg/day, 300 mg/day, 400 mg/day, 500 mg/day, 600 mg/day, 700 mg/day, 800 mg/day, 900 mg/day or 1000 mg/day.

The present compounds can also be delivered in a nano crystal dispersion formulation (see U.S. Pat. No. 5,145,684 or 6,045,829). The nano crystalline formulations typically afford greater bioavailability of drug compounds.

The present compounds can be administered parenterally, for example, by IV, IM, depo-IM, SC, or depo-SC. When administered parenterally, a therapeutically effective amount of about 0.5 to about 1000 mg/day, preferably from about 5 to about 500 or 50-200 mg daily should be delivered. The parenteral dosage form can be a depo formulation in which case a larger amount of drug can be administered with reduced frequency.

The present compounds can be administered sublingually. When given sublingually, the one or more active agents and/or analogs thereof can be given one to four times daily in the amounts described above for IM administration.

The present compounds can be administered intranasally. Appropriate formulations include a nasal spray or dry powder. The dosage of the one or more active agents and/or analogs thereof for intranasal administration is the amount described above for IM administration.

The present compounds can be administered intrathecally in a parenteral formulation. The dosage of the one or more active agents and/or analogs thereof for intrathecal administration is the amount described above for IM administration.

The present compounds can be administered topically or transdermally. When given by this route, the appropriate dosage form is a cream, ointment, or patch. When administered topically, the dosage can be from about 0.5 mg/day to about 200 mg/day. Because the amount that can be delivered by a patch is limited, two or more patches may be used. The number and size of the patch is not important, what is important is that a therapeutically effective amount of the one or more active agents and/or analogs thereof be delivered. The one or more active agents and/or analogs thereof can be administered rectally by suppository. When administered by suppository, the therapeutically effective amount can be from about 0.5 mg to about 500 mg.

The present compounds can be administered by implants. When administering one or more active agents by implant, the therapeutically effective amount is the amount described above for depot administration.

The exact dosage and frequency of administration depends on the particular condition being treated, the severity of the condition being treated, the age, weight, general physical condition of the particular patient, and other medication the individual may be taking.

VII. Combination Therapies

The present compounds can be used in combination with each other or with other therapeutic agents or approaches used to treat, mitigate or prevent impaired insulin sensitivity, glucose tolerance, obesity, diabetes, metabolic syndrome, NAFLD, NASH, PSC, PBC, or other metabolic syndrome component conditions. For example, the one or more active agents described herein and/or analogs thereof can be co-administered with insulin. Insulin is frequently required in patients with long standing diabetes mellitus, and one or more active agents described herein may lower the insulin requirements. Insulin at high doses may have a proatherogenic effect. The combination drug will, therefore, have multiple benefits compared to insulin alone.

The present compounds can be co-administered with other diabetes drugs and obesity drugs. Diabetes drugs suitable for combination therapy include sulfonylurea agents such as glipizide, glyburide (glibenclamide), chlorpropamide, tolbutamide, tolazamide and glimepiride, or the pharmaceutically acceptable salt forms thereof (see, e.g., U.S. 2003/008869); biguanide agents such as metformin and its pharmaceutically acceptable salt forms (see, e.g., U.S. patent Pub. No. 2003/0018028); thiazolidinedione agents pioglitazone or rosiglitazone, or a pharmaceutically acceptable salt form thereof (see, e.g., U.S. 2002/0198203); alpha-glucosidase inhibitors such as miglitol or acarbose, or a pharmaceutically acceptable salt form thereof (see, e.g., U.S. 2003/0013709); antilipemic agents (also known as antihyperlipidemic agents) such as bile acid sequestrants, fibric acid derivatives, HMG-CoA reductase inhibitors and nicotinic acid compounds (see, e.g., U.S. Patent Application No. 2002/0198202); angiotensin converting enzyme (ACE) inhibitors such as quinapril, ramipril, verapamil, captopril, diltiazem, clonidine, hydrochlorothiazide, benazepril, prazosin, fosinopril, lisinopril, atenolol, enalapril, perindopril, perindopril tert-butylamine, trandolapril and moexipril, or a pharmaceutically acceptable salt form thereof (see, e.g., U.S. Patent Application No. 2003/0055058); aldose reductase inhibitors (preventing eye and nerve damage in people with diabetes) such as minalrestat Tolrestat, Sorbinil, Methosorbinil, Zopolrestat, Epalrestat, Zenarestat Imirestat, and Ponalrestat or the pharmaceutically acceptable salt forms thereof (see, e.g., U.S. Patent Application No. 2002/0198201). Obesity drugs suitable for combination therapy include central nervous system (CNS) stimulants such as phentermines (e.g., those sold under the tradenames Ionamin® and Adipex-P®) (see, e.g., U.S. Pat. No. 5,019,594). The phentermines are members of a class of drugs known as the sympathomimetics for their ability to mimic stimulation of the central nervous system; re-uptake inhibitors such as 5HT-2C inhibitors (e.g., Meridia® (sibutramine), Lorcaserin (APD-356)) (see, e.g., U.S. Pat. No. 4,929,629); CB-1 antagonists such as rimonabant (Acomplia®) and CP-945598 (see, e.g., U.S. Pat. No. 5,624,941); and GLP-1 agonists or mimetics such as exenatide (Byetta®) (see, e.g., U.S. Pat. No. 5,424,286).

IX. Monitoring Efficacy

Clinical efficacy can be monitored by measuring one or more of the condition parameters or physical symptoms of impaired insulin sensitivity, glucose tolerance, obesity, diabetes, metabolic syndrome, NAFLD, NASH, PSC, PBC, or other metabolic syndrome component conditions, including blood pressure, blood insulin, free fatty acid, bodyweight, triglyceride levels, blood glucose levels, high body mass index. Observation of the stabilization, improvement and/or reversal of one or more symptoms indicates that the treatment or prophylaxis regime is efficacious. Observation of the progression, increase or exacerbation of one or more symptoms indicates that the treatment or prophylaxis regime is not efficacious.

Clinical efficacy can also be monitored using biomarkers. Biomarkers for assessing treatment are preferably assessed at the protein level, but measurement of mRNA encoding biomarkers can also be used as a surrogate measure of biomarker expression. Such a level can be measured in a blood sample, e.g., on PBMC's. The level of some biomarkers are reduced in subjects with impaired insulin sensitivity, glucose tolerance, obesity, diabetes, metabolic syndrome, NAFLD, NASH, PSC, PBC, or other metabolic syndrome component conditions relative to a control population of normal individuals (i.e., free of known conditions). An increase in level of such a marker provides an indication of a favorable treatment response, whereas an unchanged or decreasing levels provides an indication of unfavorable or at least non-optimal treatment response. The level of other biomarkers is increased in subjects with impaired insulin sensitivity, glucose tolerance, obesity, diabetes, metabolic syndrome, NAFLD, NASH, PSC, PBC, or other metabolic syndrome component conditions relative to a control population of normal individuals. An decrease in level of such a biomarker provides an indication of a favorable treatment response, whereas an unchanged or increasing levels provides an indication of unfavorable or at least non-optimal treatment response.

The monitoring methods can entail determining a baseline value of a measurable biomarker or condition parameter in a subject before administering a dosage of the one or more active agents described herein, and comparing this with a value for the same measurable biomarker or parameter after a course of treatment.

In other methods, a control value (i.e., a mean and standard deviation) of the measurable biomarker or parameter is determined for a control population. A suitable control population is one in which subjects have not received prior treatment and do not have a target condition, nor are at known risk of developing a target condition. In such methods, if the value of the measurable biomarker or clinical parameter approaches the control value, then treatment is considered efficacious. In other methods, the individuals in the control population have not received prior treatment and have been diagnosed with a target condition. In such methods, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation or preferably two standard deviations) determined in population of subjects after undergoing a course of treatment. Alternatively, the measured value in the subject can be compared with a control value in populations of prophylactically treated subjects who remain free of symptoms of a condition, or populations of therapeutically treated subjects who show amelioration of the condition's characteristics. In such cases, if the value of the measurable biomarker or clinical parameter approaches the control value, then treatment is considered efficacious and need not be resumed. On the other hand, a significant difference relative to the control level (i.e., more than one or preferably two standard deviations) is an indicator that treatment should be resumed in the subject.

The subject matter described herein is directed to the following embodiments: 1B. A compound of Formula II:

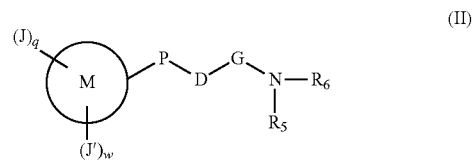

(II)

wherein, ring M is selected from the group consisting of aryl, heteroaryl, cycloalkyl, and heterocyclo;

J and J' are each independently selected from the group consisting of halo, hydroxyl, linear or branched alkyl, alkoxy, nitro, mercapto, cyano, heterocyclo, cycloalkyl, aryl, and heteroaryl, wherein said aryl, heterocyclo, cycloalkyl, or heteroaryl is optionally substituted 1 to 3 times, in each instance, with one or a combination of alkoxy, linear or branched alkyl, halo, hydroxyl, or cyano;

w and q are each independently 0 or 1;

P is S, NH, or a bond;

D is $(CR_3R_4)_y$, wherein y is 0 or 1;

$R_3$ and $R_4$ are each hydrogen;

G is $CH_2$ or C=O;

$R_5$ is selected from the group consisting of hydrogen, linear or branched alkyl, hydroxyl, alkoxy, hydroxyalkyl, and halo; or, $R_5$ is taken together with the nitrogen to which it is attached and G, D, and one of $R_3$ and $R_4$ to form a heterocyclo;

$R_6$ (A) is selected from the group consisting of halo, linear or branched alkyl, haloalkyl, alkenyl, alkynyl, cycloalkyl, cycloalkylalkyl, aryl, heteroaryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, —$(CH_2)_f$NHC(O)-aryl, —$(CH_2)_f$NHC(O)-heteroaryl, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, heteroaryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro, and cyano; wherein, f is 0, 1, 2, 3, 4, or 5;

m is 0, 1, 2 or 3; and said heteroaryl, aryl, heterocyclo, heterocycloalkyl, cycloalkyl, or S in —S(O)$_m$ (A) is optionally substituted 1 to 3 times, in each instance, with one or a combination of linear or branched alkyl, —NR$_{50}$C(O)(CH$_2$)$_b$N(R$_{60}$R$_{70}$), halo, arylalkyl, aryl, hydroxyl, alkoxy, heterocycloalkyl, heteroarylalkyl, or heteroaryl (B); wherein, R$_{50}$ is hydrogen or linear or branched alkyl;

b is 0, 1, or 2;

R$_{60}$ and R$_{70}$ are each independently selected from the group consisting of hydrogen, linear or branched alkyl, halo, and haloalkyl; and wherein said heterocycloalkyl, heterocyclo, heteroarylalkyl, aryl, or heteroaryl (B) is optionally substituted 1 to 3 times, in each instance, with one or a combination of heterocyclo, cycloalkyl, alkoxy, halo, or linear or branched alkyl; or, R$_5$ and R$_6$ are taken together with the nitrogen to which they are attached to form a heteroaryl or heterocyclo, wherein said heteroaryl or heterocyclo (C) is optionally substituted 1 to 3 times, in each instance, with one or a combination of branched or linear alkyl, aryl, hydroxyl, haloalkoxy, hydroxyalkyl, heteroaryl, arylalkyl, heterocyclo, halo, alkoxy, —(CH$_2$)$_f$NHC(O)-aryl, or —(CH$_2$)$_f$NHC(O)-heteroaryl (D), wherein said heteroaryl, aryl, heterocyclo, or arylalkyl (D) is optionally substituted 1 to 3 times, in each instance, with one or a combination of branched or linear alkyl, heterocyclo, halo, nitro, hydroxy, hydroxyalkyl, alkoxy, haloalkoxy, heteroaryl, or aryl (E), wherein said heteroaryl, heterocyclo, or aryl (E) is optionally substituted 1 to 3 times, in each instance, with one or a combination of hydroxyl, aryl, branched or linear alkyl, alkoxy, haloalkoxy, or halo; or pharmaceutically acceptable salt thereof.

1A. A compound of Formula II:

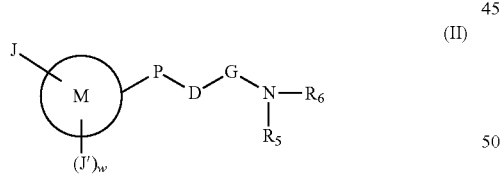

(II)

wherein ring M is selected from the group consisting of aryl, heteroaryl, cycloalkyl, and heterocyclo;

J and J' are each independently selected from the group consisting of hydrogen, halo, hydroxyl, linear or branched alkyl, alkoxy, nitro, mercapto, cyano, heterocyclo, cycloalkyl, aryl, and heteroaryl, wherein said aryl or heteroaryl is optionally substituted 1 to 3 times with one or a combination of alkoxy, linear or branched alkyl, halo, hydroxyl, or cyano;

w is 0 or 1

P is S, NH, or a bond;

D is (CR$_3$R$_4$)$_y$, wherein y is 0 or 1;

R$_3$, and R$_4$ are each hydrogen;

G is CH$_2$ or C=O;

R$_5$ is selected from the group consisting of hydrogen, linear or branched alkyl, hydroxyl, alkoxy, hydroxyalkyl, and halo;

R$_6$ is selected from the group consisting of halo, alkyl, haloalkyl, alkenyl, alkynyl, cycloalkyl, cycloalkylalkyl, aryl, heteroaryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, —(CH$_2$)$_f$NHC(O)-aryl, —(CH$_2$)$_f$NHC(O)-heteroaryl, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heteroaryl-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano, wherein f=0, 1, 2, 3, 4, or 5; m=0, 1, 2 or 3, and wherein the heteroaryl, aryl, heterocyclo, or S in —S(O)$_m$ is optionally substituted 1 to 3 times with one or a combination of linear or branched alkyl, —NR$_{50}$C(O)(CH$_2$)$_b$N(R$_{60}$R$_{70}$), halo, arylalkyl, aryl, heterocyclo, heterocycloalkyl, heteroarylalkyl, or heteroaryl;

wherein R$_{50}$ is hydrogen or linear or branched alkyl;

b is 0, 1, or 2;

R$_{60}$ and R$_{70}$ are each independently selected from the group consisting of hydrogen, linear or branched alkyl, halo, and haloalkyl; and wherein said heterocyclo, heterocycloalkyl, heteroarylalkyl, aryl, or heteroaryl is optionally substituted 1 to 3 times with one or a combination of heterocyclo, halo, or linear or branched alkyl; or, R$_5$ may be taken together with the nitrogen to which it is attached and G, D, and one of R$_3$ and R$_4$ to form a heterocyclo; or R$_5$ and R$_6$ may be taken together with the nitrogen to which they are attached to form a heteroaryl or heterocyclo, wherein the heteroaryl or heterocyclo is optionally substituted 1 to 3 times with one or a combination of branched or linear alkyl, aryl, hydroxy, hydroxyalkyl, heteroaryl, arylalkyl, heterocyclo, halo, alkoxy, —(CH$_2$)$_f$NHC(O)-aryl, or —(CH$_2$)$_f$NHC(O)-heteroaryl, wherein said heteroaryl, heterocyclo, or arylalkyl is optionally substituted 1 to 3 times with one or a combination of branched or linear alkyl, halo, nitro, hydroxy, hydroxyalkyl, alkoxy, heteroaryl, or aryl, wherein said heteroaryl, heterocyclo, or aryl is optionally substituted 1 to 3 times with one or a combination of hydroxyl, branched or linear alkyl, haloalkoxy, or halo, or pharmaceutically acceptable salt thereof.

2A. The compound of embodiment 1A or 1B, wherein M is a C$_6$-C$_{12}$ aryl, 5-12 membered heterocyclo, or 5-12 membered heteroaryl, containing one, two, or three ring heteroatoms.

3A. The compound of embodiment 1A, 1B, or 2A, wherein M is selected from the group consisting of

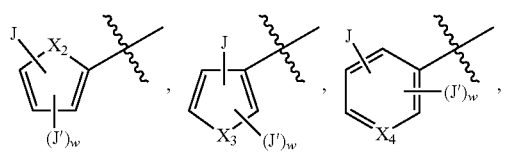

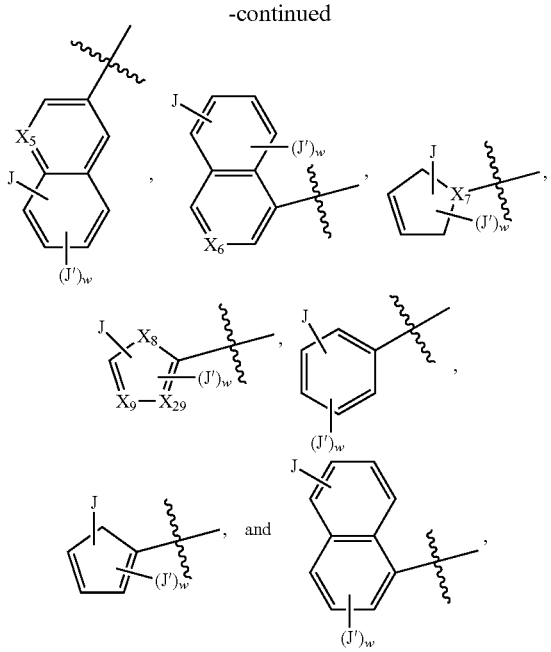

wherein $X_2$, $X_3$, $X_4$, $X_5$, $X_6$, $X_7$, $X_8$, $X_9$, and $X_{10}$ are each independently selected from the group consisting of O, N, NH, and S, and where the squiggle line indicates the point of attachment to P.

4A. The compound of any one of embodiments 1A-3A, wherein J is selected from the group consisting of hydrogen, halo, hydroxyl, and linear or branched $C_1$-$C_3$ alkyl.

5A. The compound of embodiment 4A, wherein halo is selected from the group consisting of fluoro, chloro, and bromo.

6A. The compound of embodiment 5A, wherein halo is fluoro.

7A. The compound of any one of embodiments 1B or 1A-6A, wherein J' is selected from the group consisting of aryl, heteroaryl, heterocyclo, cycloalkyl, and halo, wherein said aryl or heteroaryl is optionally substituted 1 to 3 times with alkoxy, $C_1$-$C_3$ alkyl, halo, hydroxyl, or cyano.

8A. The compound of embodiment 7A, wherein halo is fluoro.

9A. The compound of embodiment 7A, wherein alkoxy is methoxy.

10A. The compound of any one of embodiments 1B or 1A-7A, wherein G is C=O.

11A. The compound of any one of embodiments 1B or 1A-10A, wherein y is 0.

12A. The compound of any one of embodiments 1B or 1A-11A, wherein P is a bond.

13A. The compound of any one of embodiments 1B or 1A-12A, wherein $R_5$ is selected from the group consisting of hydrogen, hydroxyl, and linear or branched $C_1$-$C_3$ alkyl.

14A. The compound of any one of embodiments 1B or 1A-13A, wherein $R_5$ is hydrogen.

15A. The compound of any one of embodiments 1B or 1A-14A, wherein $R_6$ is selected from the group consisting of aryl, heteroaryl, cycloalkyl, heterocyclo, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, and heteroaryl-S(O)$_m$, wherein said aryl, heterocyclo, heteroaryl, aryl, heterocycloalkyl, or S in —S(O)$_m$ is optionally substituted 1 to 3 times with one or a combination of linear or branched $C_1$-$C_3$ alkyl, halo, arylalkyl, aryl, or heteroaryl, and wherein said aryl or heteroaryl is optionally substituted 1 to 3 times with one or a combination of heterocyclo, halo, or linear or branched $C_1$-$C_3$ alkyl.

16A. The compound of any one of embodiments 1B or 1A-15A, wherein $R_6$ is alkyl-S(O)$_m$, wherein S in S(O)$_m$ is optionally substituted 1 to 3 times with one or a combination of linear or branched $C_1$-$C_3$ alkyl, arylalkyl, aryl, or heteroaryl.

17A. The compound of any one of embodiments 1B or 1A-16A, wherein m is 2.

18A. The compound of embodiment 17A, wherein $R_6$ is —CH$_2$CH$_2$—S(O)$_2$, wherein S is substituted with benzyl.

19A. The compound of embodiment 18A, wherein said compound has the structure

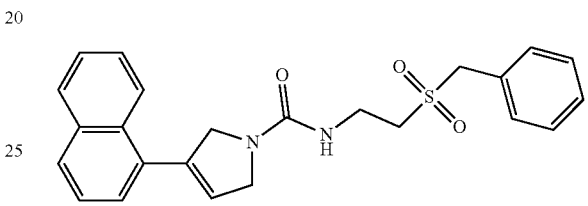

20A. The compound of embodiment 15A, wherein $R_6$ is selected from the group consisting of aryl, heteroaryl, and heterocyclo, optionally substituted 1 to 3 times with one or a combination of aryl, heteroaryl, arylalkyl, —NR$_{50}$C(O)(CH$_2$)$_b$N(R$_{60}$R$_{70}$), or heterocyclo, wherein said aryl, heteroaryl, arylalkyl, or heterocyclo is optionally substituted 1 to 3 times with one or a combination of cycloalkyl, linear or branched $C_1$-$C_3$ alkyl, or halo.

21A. The compound of embodiment 20A, wherein $R_6$ is phenyl, wherein said phenyl is substituted 1 to 3 times with one or a combination of aryl, heteroaryl, arylalkyl, —NR$_{50}$C(O)(CH$_2$)$_b$N(R$_{60}$R$_{70}$), or heterocyclo, wherein said aryl, heteroaryl, arylalkyl, or heterocyclo is optionally substituted 1 to 3 times with one or a combination of cycloalkyl, linear or branched $C_1$-$C_3$ alkyl, or halo.

22A. The compound of embodiment 20A, wherein $R_6$ is heteroaryl, wherein said heteroaryl is selected from the group consisting of acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl, wherein said heteroaryl is substituted 1 to 3 times with one or a combination of aryl, heteroaryl, arylalkyl, or, heterocyclo, and wherein said aryl, heteroaryl, arylalkyl, or heterocyclo is optionally substituted 1 to 3 times with one or a combination of cycloalkyl, linear or branched $C_1$-$C_3$ alkyl, or halo.

23A. The compound of embodiment 20A, wherein $R_6$ is selected from the group consisting of

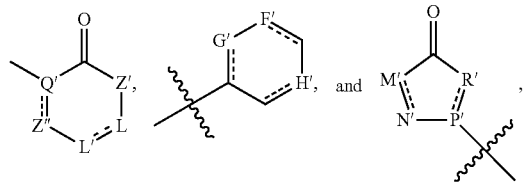

wherein the double bonds are absent or present, Q', Z", L', L, Z', G', F', H, M', N', P, and R' are each independently selected from the group consisting of N, O, S, NH, C, $CH_2$, and CH, and wherein $R_6$ is optionally substituted 1 to 3 times with one or a combination of aryl, heteroaryl, arylalkyl, or, heterocyclo, wherein said aryl, heteroaryl, arylalkyl, or heterocyclo is optionally substituted 1 to 3 times with one or a combination of cycloalkyl, linear or branched $C_1$-$C_3$ alkyl, or halo, and where the squiggle line is the point of attachment to N.

24A. The compound of embodiment 23A, wherein $R_6$ is

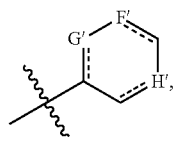

wherein G', F', and H' are each CH, the double bonds are present, and wherein $R_6$ is optionally substituted 1 to 3 times with one or a combination of aryl, heteroaryl, arylalkyl, or, heterocyclo, wherein said aryl, heteroaryl, arylalkyl, or heterocyclo is optionally substituted 1 to 3 times with one or a combination of cycloalkyl, linear or branched $C_1$-$C_3$ alkyl, or halo.

25A. The compound of embodiment 23A, wherein $R_6$ is

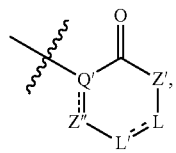

wherein the double bonds are present, Q' is C; Z", L', L, are each CH; and Z' is N (wherein Z' is substituted); and wherein $R_6$ is optionally substituted 1 to 3 times with one or a combination of aryl, heteroaryl, arylalkyl, or, heterocyclo, wherein said aryl, heteroaryl, arylalkyl, or heterocyclo is optionally substituted 1 to 3 times with one or a combination of cycloalkyl, linear or branched $C_1$-$C_3$ alkyl, or halo.

26A. The compound of embodiment 23A, wherein $R_6$ is

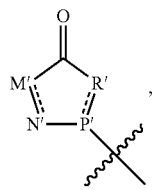

wherein each of the double bonds is absent, M' is NH or N (wherein M' is substituted), N' is $CH_2$, P' is CH, and R' is $CH_2$, and wherein $R_6$ is optionally substituted 1 to 3 times with one or a combination of aryl, heteroaryl, arylalkyl, or, heteroaryl, wherein said aryl, heteroaryl, arylalkyl, or heterocyclo is optionally substituted 1 to 3 times with one or a combination of cycloalkyl, linear or branched $C_1$-$C_3$ alkyl, or halo.

27A. The compound of embodiment 20A, wherein $R_6$ is substituted with a substituent selected from the group consisting of phenyl, benzyl, benzimidazolyl, benzothiazolyl, benzindolyl, benzofuranyl, benzothiazolyl, benzothiadiazolyl, furanyl, isothiazolyl, imidazolyl, indazolyl, indolyl, indazolyl, isoindolyl, isoquinolyl, isoxazolyl, naphthyridinyl, oxadiazolyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, and triazinyl, wherein said substituent is optionally substituted 1 to 3 times with one or a combination of cyclopropyl, cyclopentyl, cyclobutyl, cyclohexyl, methyl, ethyl, propyl, chloro, fluoro, bromo, methoxy, or ethoxy.

28A. The compound of embodiment 27A, wherein $R_6$ is substituted with a substituent selected from the group consisting of phenyl, benzyl, and tetrazolyl, wherein said substituent is optionally substituted 1 to 3 times with one or a combination of cyclopropyl, cyclopentyl, cyclobutyl, cyclohexyl, methyl, ethyl, propyl, chloro, fluoro, bromo, methoxy, or ethoxy.

29A. The compound of any one of embodiments 1B or 1A-28A, wherein said compound is selected from the group consisting of

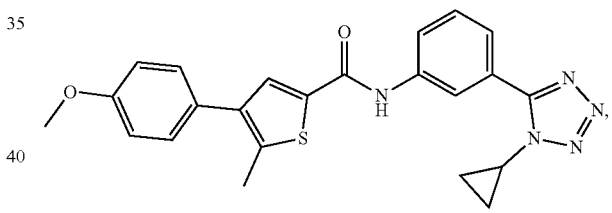

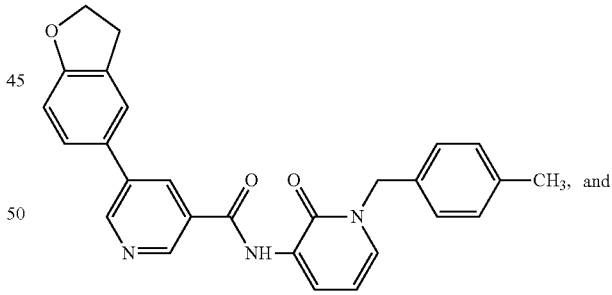

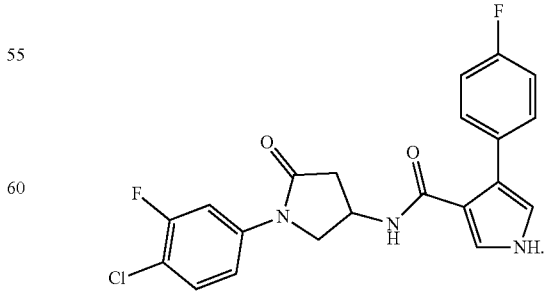

30A. The compound of any one of embodiments 1B or 1A-12A, wherein $R_5$ and $R_6$ may be taken together with the nitrogen to which they are attached to form a heteroaryl or heterocyclo, wherein the heteroaryl or heterocyclo is optionally substituted 1 to 3 times with one or a combination of branched or linear alkyl, hydroxyl, hydroxyalkyl, heteroaryl, arylalkyl, heterocyclo, halo, alkoxy, —(CH$_2$)$_f$NHC(O)-aryl, or —(CH$_2$)$_f$NHC(O)-heteroaryl, wherein said heteroaryl, heterocyclo, or arylalkyl is optionally substituted 1 to 3 times with one or a combination of branched or linear alkyl, halo, hydroxyl, hydroxyalkyl, alkoxy, heteroaryl, or aryl, wherein said heteroaryl or aryl is optionally substituted 1 to 3 times with one or a combination of hydroxyl, branched or linear alkyl, haloalkoxy, or halo.

31A. The compound of embodiment 30A, wherein R$_5$ and R$_6$ may be taken together with the nitrogen to which they are attached to form a 5-10-membered mono, bridged, fused, or spiro heterocyclo, wherein said heterocyclo or heteroaryl contains one or two heteroatoms, and wherein said heterocyclo is optionally substituted 1 to 3 times with one or a combination of aryl, hydroxy, hydroxyalkyl, linear or branched C$_1$-C$_6$ alkyl, haloalkoxy, heteroaryl, heterocyclo, or —(CH$_2$)$_f$NHC(O)-heteroaryl, wherein f is 1, and wherein said aryl, heteroaryl, or heterocyclo is optionally substituted 1 to 3 times with haloalkoxy, halo, linear or branched C$_1$-C$_6$ alkyl.

32A. The compound of any one of embodiments 1B or 1A-31A, wherein R$_5$ and R$_6$ may be taken together with the nitrogen to which they are attached to form a 9-membered spiro heterocyclo, wherein said spiro heterocyclo is

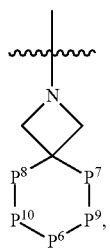

wherein P$_6$, P$_7$, P$_8$, P$_9$, and P$_{10}$ are each independently selected from the group consisting of N, NH O, S, and CH$_2$, wherein the squiggle line represents the point of attachment to G, and wherein the spiro heterocyclo is optionally substituted 1 to 3 times with aryl, hydroxy, hydroxyalkyl, linear or branched C$_1$-C$_6$ alkyl, haloalkoxy, heteroaryl, heterocyclo, or —(CH$_2$)$_f$NHC(O)-heteroaryl, wherein f is 1, and wherein said aryl, heteroaryl, or heterocyclo is optionally substituted 1 to 3 times with one or a combination of haloalkoxy, halo, linear or branched C$_1$-C$_6$ alkyl.

33A. The compound of embodiment 32A, wherein, P$_6$ is O and P$_7$, P$_8$, P$_9$, and P$_{10}$ are each hydrogen.

34A. The compound of embodiment 32A or 33A, wherein the spiro heterocyclo is substituted with a heterocyclo, wherein said heterocyclo is further substituted with C$_1$-C$_6$ alkyl.

35A. The compound of any one of embodiments 32A-34A, wherein the spiro heterocyclo is substituted with a pyrazole, and wherein said pyrazole is substituted with isobutyl.

36A. The compound of embodiment 32A, wherein R$_5$ and R$_6$ may be taken together with the nitrogen to which they are attached to form a compound selected from the group consisting of pyrrolidine, piperidine, or morpholine, wherein said pyrrolidine, piperidine, or morpholine is optionally substituted 1 to 3 times with one or a combination of aryl, hydroxy, hydroxyalkyl, linear or branched C$_1$-C$_6$ alkyl, haloalkoxy, heteroaryl, heterocyclo, or —(CH$_2$)$_f$NHC(O)-heteroaryl, wherein f is 1, and wherein said aryl, heteroaryl, or heterocyclo is optionally substituted 1 to 3 times with one or a combination of haloalkoxy, halo, and linear or branched C$_1$-C$_6$ alkyl.

37A. The compound of any one of embodiments 30A-36A, wherein said compound is selected from the group consisting of

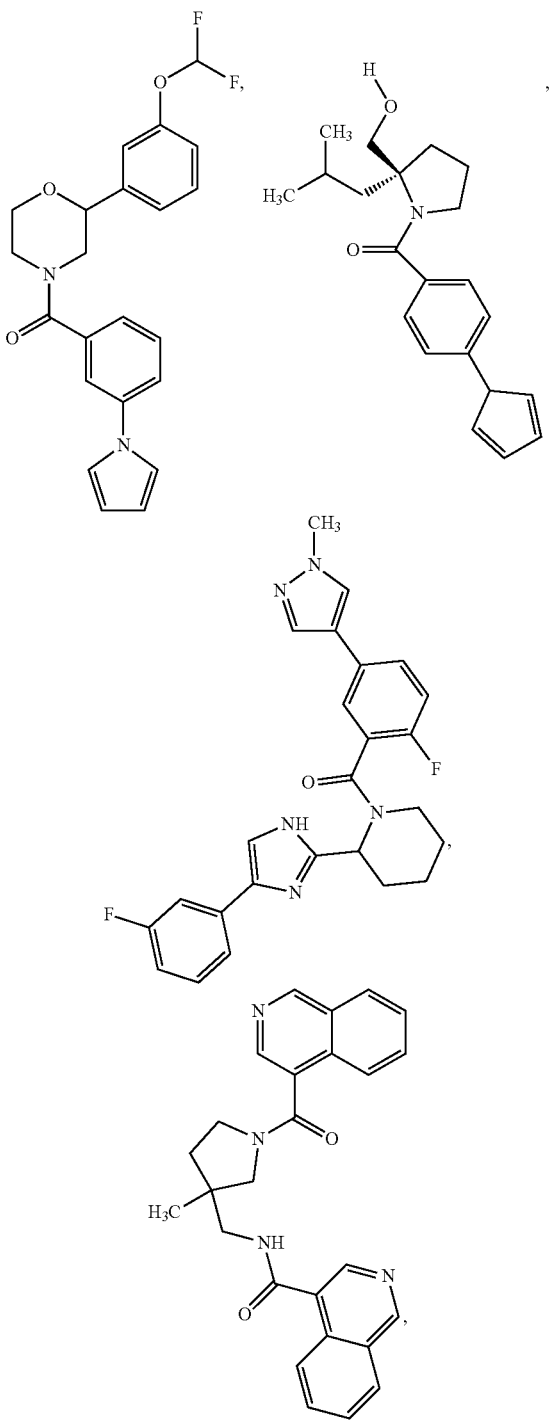

-continued

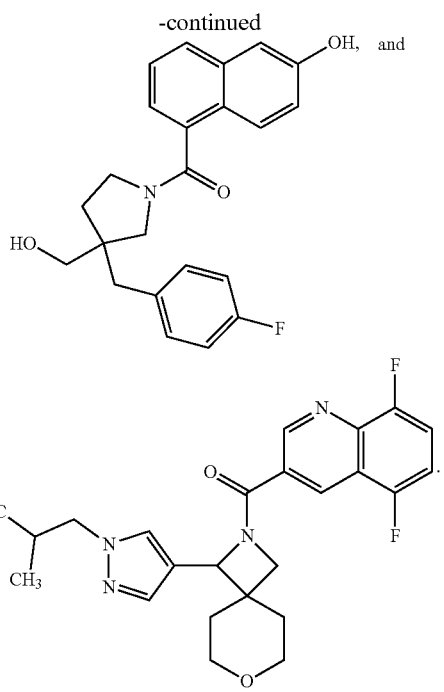

38A. The compound of any one of embodiments 1B or 1A-10A, where P is S.
39A. The compound of embodiment 38A, wherein D is $(CR_3R_4)_y$, wherein $R_3$ and $R_4$ are each hydrogen, and y is 1.
40A. The compound of embodiment 38A or 39A, where $R_5$ may be taken together with the nitrogen to which it is attached and G, D, and one of $R_3$ and $R_4$ to form a heterocyclo.
41A. The compound of embodiment 40A, wherein the heterocyclo is a 5- or 6-membered heterocyclo containing one or two heteroatoms.
42A. The compound of any one of embodiments 38A-41A, wherein $R_6$ is selected from the group consisting of aryl, heteroaryl, heterocyclo, and cycloalkyl, and wherein said aryl or heteroaryl is optionally substituted 1 to 3 times with one or a combination of linear or branched $C_1$-$C_3$ alkyl, hydroxyl, alkoxy, or halo.
43A. The compound of embodiment 42A, wherein $R_6$ is aryl, optionally substituted 1 to 3 times with alkoxy or hydroxyl.
44A. The compound of embodiment 42A or 43A, wherein $R_6$ is phenyl, optionally substituted 1 to 3 times with methoxy.
45A. The compound of any one of embodiments 38A-44A, wherein M is

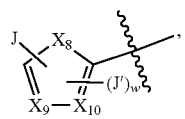

wherein $X_8$, $X_9$, and $X_{10}$ are each independently selected from N, NH, or O.

46A. The compound of any one of embodiments 38A-45A, wherein M is

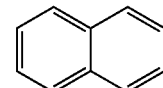

wherein $X_8$ is O and $X_9$ and $X_{10}$ are each N.
47A. The compound of any one of embodiments 38A-46A, wherein J is $C_6$-$C_{10}$ aryl.
48A. The compound of any one of embodiments 38A-47A, wherein w is 0.
49A. The compound of embodiment 48A, wherein said compound is

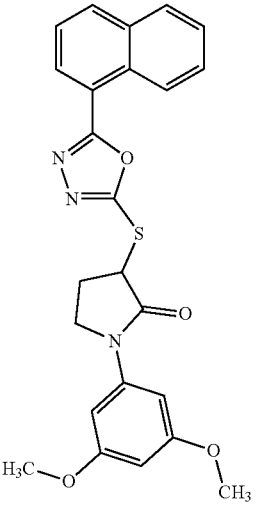

50A. The compound of embodiment 1B, 1A or 2A, wherein M is aryl.
51A. The compound of embodiment 50A, wherein M is phenyl.
52A. The compound of embodiment 50A or 51A, wherein J is hydrogen.
53A. The compound of any one of embodiments 50A-52A, wherein J' is selected from the group consisting of aryl, heteroaryl, heterocyclo, and cycloalkyl, wherein said aryl or heteroaryl is optionally substituted 1 to 3 times with one or a combination of alkoxy, $C_1$-$C_3$ alkyl, halo, hydroxyl, or cyano.
54A. The compound of embodiment 53A, wherein J' is aryl substituted with cyano.
55A. The compound of any one of embodiments 50A-54A, wherein P is a bond.
56A. The compound of any one of embodiments 50A-55A, wherein G is $CH_2$.
57A. The compound of any one of embodiments 50A-56A, wherein y is 0.
58A. The compound of any one of embodiments 50A-57A, wherein $R_5$ is selected from the group consisting of hydroxyalkyl, hydrogen, halo, and alkoxy.
59A. The compound of embodiment 58A, wherein $R_5$ is hydroxyalkyl.
60A. The compound of embodiment 58A or 59A, wherein $R_5$ is hydroxyethyl.

61A. The compound of any one of embodiments 50A-60A, wherein $R_6$ is selected from the group consisting of halo, linear or branched $C_1$-$C_6$ alkyl, haloalkyl, alkenyl, and alkynyl.

62A. The compound of embodiment 61A, wherein $R_6$ is linear or branched $C_1$-$C_6$ alkyl.

63A. The compound of embodiment 61A or 62A, wherein $R_6$ is neo-pentyl.

64A. The compound of embodiment 63A, wherein said compound is

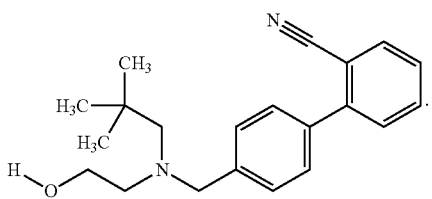 [SMILES: CC(C)(C)CN(CCO)Cc1ccc(-c2ccccc2C#N)cc1]

2B. The compound of embodiment 1B, wherein ring M is a $C_6$-$C_{12}$ aryl, 5- to 12-membered heterocyclo, or 5- to 12-membered heteroaryl, and wherein said heterocyclo or heteroaryl contains one, two, or three ring heteroatoms.

3B. The compound of embodiment 1B or 2B, wherein ring M is selected from the group consisting of

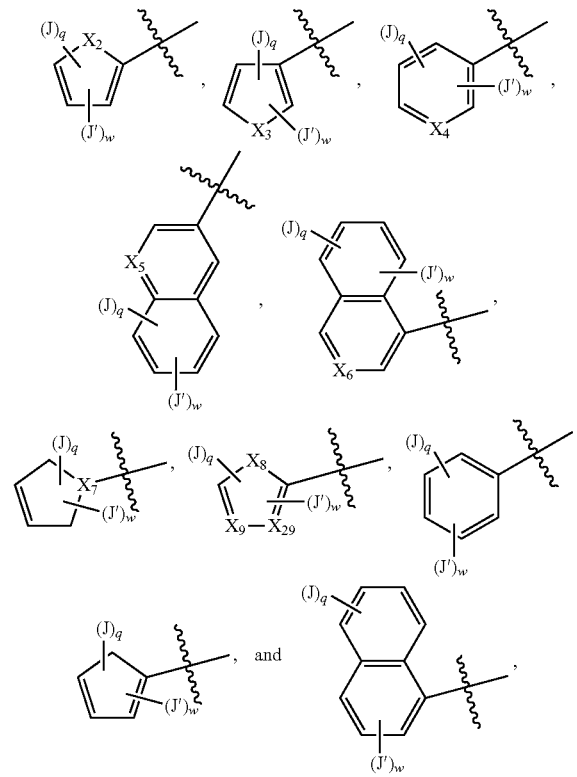

wherein $X_2$, $X_3$, $X_4$, $X_5$, $X_6$, $X_7$, $X_8$, $X_9$, and $X_{10}$ are each independently selected from the group consisting of O, N, NH, and S, and wherein ⌇ indicates the point of attachment of ring M to P.

4B. The compound of embodiment 3B, wherein $X_2$ is S; $X_3$ is NH; $X_4$ is N; $X_5$ is N; $X_6$ is N; $X_7$ is N; $X_9$ and $X_{10}$ are each N, and $X_8$ is O.

5B. The compound of embodiment 3B or 4B, wherein J is selected from the group consisting of halo, hydroxyl, or linear or branched $C_1$-$C_3$ alkyl.

6B. The compound of any one of embodiments 1B-5B, wherein J is selected from the group consisting of methyl, fluoro, and hydroxyl.

7B. The compound of any one of embodiments 1B-6B, wherein J' is selected from the group consisting of aryl, heteroaryl, heterocyclo, cycloalkyl, and halo, wherein said aryl, heteroaryl, heterocyclo, or cycloalkyl is optionally substituted 1 to 3 times, in each instance, with alkoxy, linear or branched $C_1$-$C_3$ alkyl, halo, hydroxyl, or cyano.

8B. The compound of embodiment 7B, wherein J' is selected from the group consisting of phenyl, naphthalenyl, dihydrobenzofuranyl, pyrrolyl, and pyrazolyl, optionally substituted 1 to 3 times, in each instance, with methoxy, fluoro, methyl, or cyano.

9B. The compound of any one of embodiments 1B-8B, wherein q is 0.

10B. The compound of any one of embodiments 1B-8B, wherein q is 1.

11B. The compound of any one of embodiments 1B-10B, wherein w is 0.

12B. The compound of any one of embodiments 1B-10B, wherein w is 1.

13B. The compound of embodiment 1B, wherein ring M is selected from the group consisting of

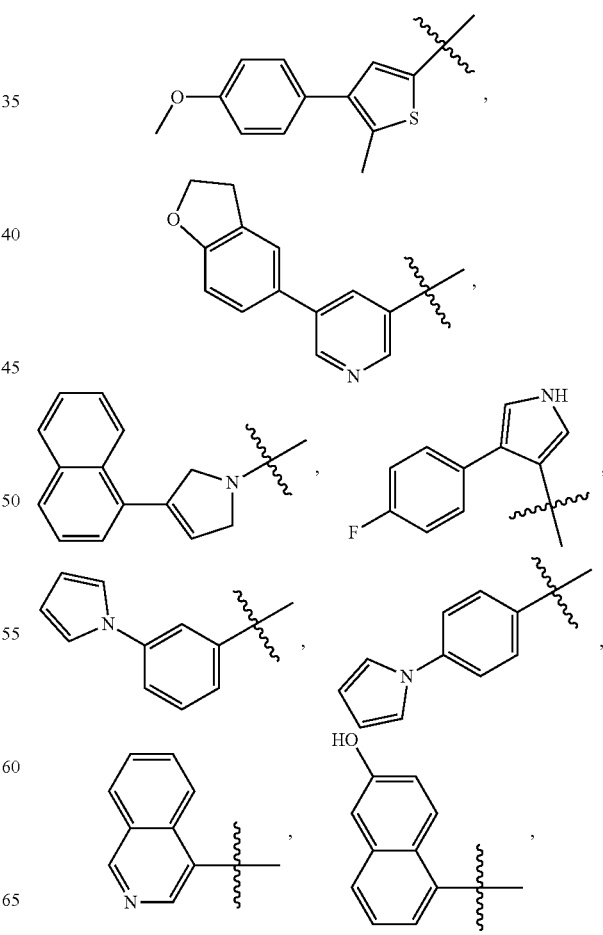

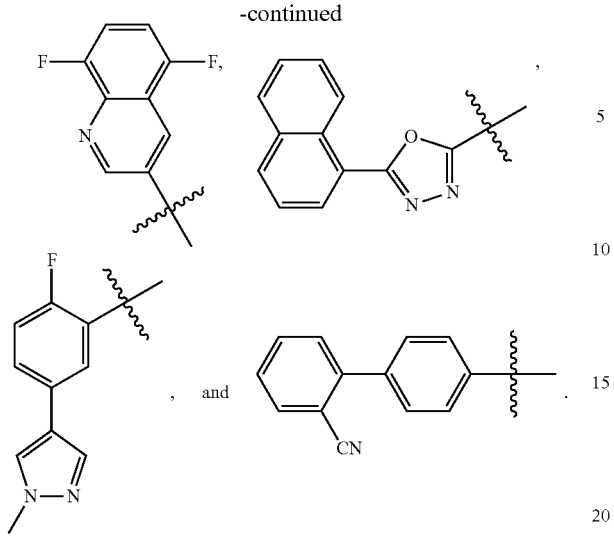

, and

14B. The compound of any one of embodiments 1B-13B, wherein G is C=O.
15B. The compound of any one of embodiments 1B-14B, wherein y is 0.
16B. The compound of any one of embodiments 1B-15B, wherein P is a bond.
17B. The compound of any one of embodiments 1B-16B, wherein $R_5$ is selected from the group consisting of hydrogen, hydroxyl, and linear or branched $C_1$-$C_3$ alkyl.
18B. The compound of any one of embodiments 1B-17B, wherein $R_5$ is hydrogen.
19B. The compound of embodiment 17B or 18B, wherein $R_6$ (A) is selected from the group consisting of aryl, heteroaryl, cycloalkyl, heterocyclo, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, and heteroaryl-S(O)$_m$, wherein said heterocyclo, heteroaryl, aryl, or S in —S(O)$_m$ (A) is optionally substituted 1 to 3 times, in each instance, with one or a combination of linear or branched $C_1$-$C_3$ alkyl, halo, arylalkyl, aryl, heterocyclo, or heteroaryl (B), and wherein said aryl or heteroaryl (B) is optionally substituted 1 to 3 times, in each instance, with one or a combination of heterocyclo, halo, cycloalkyl, alkoxy, or linear or branched $C_1$-$C_3$ alkyl.
20B. The compound of embodiment 19B, wherein $R_6$ is alkyl-S(O)$_m$, wherein S in S(O)$_m$ is optionally substituted 1 to 3 times, in each instance, with one or a combination of linear or branched $C_1$-$C_3$ alkyl, arylalkyl, aryl, or heteroaryl.
21B. The compound of embodiment 20B, wherein m is 2.
22B. The compound of embodiment 20B or 21B, wherein $R_6$ is alkyl-S(O)$_2$, wherein S is substituted once with aryl or arylalkyl.
23B. The compound of embodiment 22B, wherein $R_6$ is —CH$_2$CH$_2$—S(O)$_2$, wherein S is substituted once with benzyl.
24B. The compound of embodiment 23B, wherein ring M is a 5-membered heterocyclo.

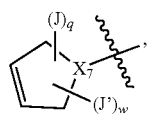

25B. The compound of embodiment 24B, wherein ring M is, wherein $X_7$ is N.
26B. The compound of embodiment 25B, wherein w is 1.
27B. The compound of embodiment 26B, wherein J' is aryl.
28B. The compound of embodiment 27B, wherein J' is naphthalenyl.
29B. The compound of embodiment 28B, wherein q is 0.
30B. The compound of any one of embodiments 24B-29B, wherein ring M is 31B. The compound of embodiment 30B, wherein said compound has the structure:

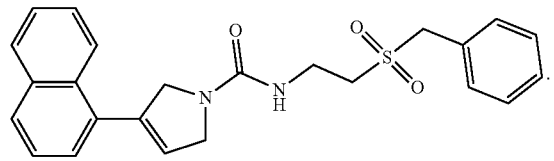 [SMILES: O=C(NCCS(=O)(=O)Cc1ccccc1)N1CC=C(c2cccc3ccccc23)C1]

31B. The compound of embodiment 19B, wherein $R_6$ (A) is selected from the group consisting of aryl, heteroaryl, and heterocyclo, optionally substituted 1 to 3 times, in each instance, with one or a combination of aryl, heteroaryl, arylalkyl, or heterocyclo (B), wherein said aryl, heteroaryl, arylalkyl, or heterocyclo (B) is optionally substituted 1 to 3 times, in each instance, with one or a combination of cycloalkyl, alkoxy, linear or branched $C_1$-$C_3$ alkyl, or halo.
32B. The compound of embodiment 31B, wherein $R_6$ (A) is phenyl, wherein said phenyl is optionally substituted 1 to 3 times, in each instance, with one or a combination of aryl, heteroaryl, arylalkyl, or heterocyclo (B), wherein said aryl, heteroaryl, arylalkyl, or heterocyclo (B) is optionally substituted 1 to 3 times, in each instance, with one or a combination of cycloalkyl, alkoxy, linear or branched $C_1$-$C_3$ alkyl, or halo.
33B. The compound of embodiment 31B, wherein $R_6$ (A) is heteroaryl, wherein said heteroaryl is selected from the group consisting of acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl, wherein said heteroaryl (A) is optionally substituted 1 to 3 times, in each instance, with one or a combination of aryl, heteroaryl, arylalkyl, or, heterocyclo (B), and wherein said aryl, heteroaryl, arylalkyl, or heterocyclo (B) is optionally substituted 1 to 3 times, in each instance, with one or a combination of cycloalkyl, alkoxy, linear or branched $C_1$-$C_3$ alkyl, or halo.

34B. The compound of embodiment 31B, wherein $R_6$ (A) is selected from the group consisting of

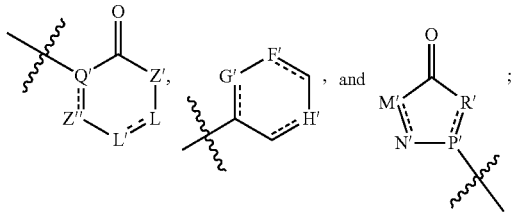

wherein the double bonds are each absent or present, Q', Z", L', L, Z', G', F', H', M', N', P', and R' are each independently selected from the group consisting of N, O, S, NH, C, $CH_2$, and CH, and wherein $R_6$ (A) is optionally substituted 1 to 3 times, in each instance, with one or a combination of aryl, heteroaryl, arylalkyl, or, heterocyclo (B), wherein said aryl, heteroaryl, arylalkyl, or heterocyclo (B) is optionally substituted 1 to 3 times, in each instance, with one or a combination of cycloalkyl, linear or branched $C_1$-$C_3$ alkyl, alkoxy or halo, and wherein ξ indicates the point of attachment to N in Formula II.

35B. The compound of embodiment 34B, wherein $R_6$ (A) is

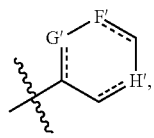

wherein G', F', and H' are each CH, each double bond is present, and wherein $R_6$ (A) is optionally substituted 1 to 3 times, in each instance, with one or a combination of aryl, heteroaryl, arylalkyl, or, heterocyclo (B), and wherein said aryl, heteroaryl, arylalkyl, or heterocyclo (B) is optionally substituted 1 to 3 times, in each instance, with one or a combination of cycloalkyl, alkoxy, linear or branched $C_1$-$C_3$ alkyl, or halo.

36B. The compound of embodiment 35B, wherein $R_6$ (A) is substituted once with heteroaryl (B), and wherein said heteroaryl (B) is substituted once with cyclopropyl, cyclobutyl, or cyclopentyl.

37B. The compound of embodiment 36B, wherein $R_6$ is substituted once with tetrazolyl, and wherein said tetrazolyl is substituted once with cyclopropyl.

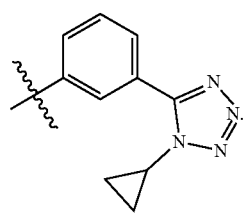 [SMILES: *c1cccc(-c2nnnn2C2CC2)c1]

38B. The compound of embodiment 37B, wherein $R_6$ is

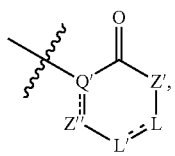

39B. The compound of embodiment 34B, wherein $R_6$ (A) is L each double bond is present, Q' is C; Z", L', L, are each CH; and Z' is NH or N (wherein Z' is substituted); and wherein $R_6$ (A) is optionally substituted 1 to 3 times, in each instance, with one or a combination of aryl, heteroaryl, arylalkyl, or, heterocyclo (B), wherein said aryl, heteroaryl, arylalkyl, or heterocyclo (B) is optionally substituted 1 to 3 times, in each instance, with one or a combination of cycloalkyl, alkoxy, linear or branched $C_1$-$C_3$ alkyl, or halo.

40B. The compound of embodiment 39B, wherein $R_6$ is substituted once with arylalkyl, and wherein said arylalkyl is substituted once with methyl, ethyl, or cyclopropyl.

41B. The compound of embodiment 40B, wherein $R_6$ is substituted once with benzyl, wherein said benzyl is substituted once with methyl.

42B. The compound of embodiment 41B, wherein $R_6$ is

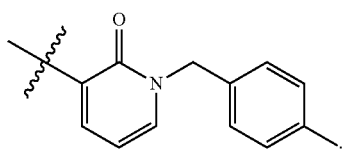

43B. The compound of embodiment 34B, wherein $R_6$ (A) is

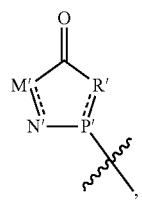

wherein each double bond is absent, M' is NH or N (wherein M' is substituted), N' is $CH_2$, P' is CH, and R' is $CH_2$, and wherein $R_6$ (A) is optionally substituted 1 to 3 times, in each instance, with one or a combination of aryl, heteroaryl, arylalkyl, or, heterocyclo (B), wherein said aryl, heteroaryl, arylalkyl, or heterocyclo (B) is optionally substituted 1 to 3 times, in each instance, with one or a combination of cycloalkyl, alkoxy, linear or branched $C_1$-$C_3$ alkyl, or halo.

44B. The compound of embodiment 43B, wherein $R_6$ is substituted once with aryl, and wherein said aryl is substituted twice with halo.

45B. The compound of embodiment 44B, wherein $R_6$ is substituted once with phenyl, and wherein said phenyl is substituted once with fluoro and once with chloro.

46B. The compound of embodiment 45B, wherein R₆ is

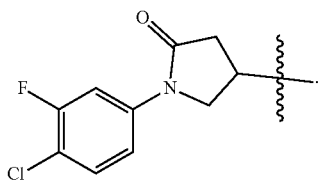

47B. The compound of embodiment 31B, wherein R₆ (A) is substituted with a substituent selected from the group consisting of phenyl, benzyl, benzimidazolyl, benzothiazolyl, benzindolyl, benzofuranyl, benzothiazolyl, benzothiadiazolyl, furanyl, isothiazolyl, imidazolyl, indazolyl, indolyl, indazolyl, isoindolyl, isoquinolyl, isoxazolyl, naphthyridinyl, oxadiazolyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, and triazinyl (B), wherein said substituent (B) is optionally substituted 1 to 3 times, in each instance, with one or a combination of cyclopropyl, cyclopentyl, cyclobutyl, cyclohexyl, methyl, ethyl, propyl, chloro, fluoro, bromo, methoxy, or ethoxy.

48B. The compound of embodiment 47B, wherein R₆ (A) is substituted with a substituent selected from the group consisting of phenyl, benzyl, and tetrazolyl (B), wherein said substituent (B) is optionally substituted 1 to 3 times, in each instance, with one or a combination of cyclopropyl, cyclopentyl, cyclobutyl, cyclohexyl, methyl, ethyl, propyl, chloro, fluoro, bromo, methoxy, or ethoxy.

48bb. The compound of any one of embodiments 31B-48B, wherein ring M is selected from the group consisting of

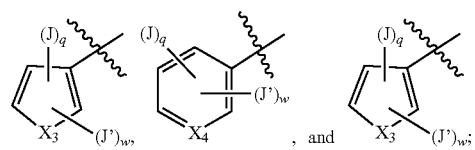

wherein J' is selected from the group consisting of aryl and heterocyclo, wherein said aryl or heterocyclo is optionally substituted with halo or alkoxy; and wherein J is linear or branched C₁-C₃ alkyl.

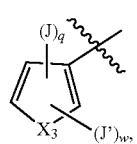

48bb1. The compound of embodiment 48bb, wherein ring M is wherein X₃ is S, J' is phenyl, wherein said phenyl is substituted with methoxy, w is 1, and q is 0.

48bb2. The compound of embodiment 48bb1, wherein ring M is

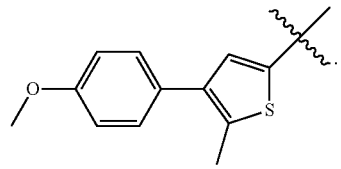 [SMILES: *c1cc(-c2ccc(OC)cc2)c(C)s1]

48bb3. The compound of embodiment 48bb, wherein ring M is

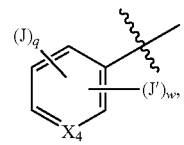

wherein X₄ is N, J' is dihydrobenzofuranyl, w is 1, and q is 0.

48bb4. The compound of embodiment 48bb3, wherein ring M is

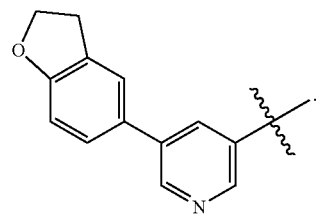 [SMILES: *c1cncc(-c2ccc3c(c2)CCO3)c1]

48bb5. The compound of embodiment 48bb, wherein ring M is

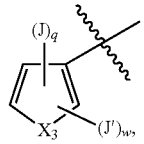

wherein X₃ is NH, J' is phenyl, wherein said phenyl is substituted with fluoro, w is 1, and q is 1.

48bb6. The compound of embodiment 48bb5, wherein ring M is

49B. The compound of any one of embodiments 31B-48B, 48bb, 48bb1, 48bb2, 48bb3, 48bb4, 48bb5, or 48bb6, wherein ring M is selected from the group consisting of

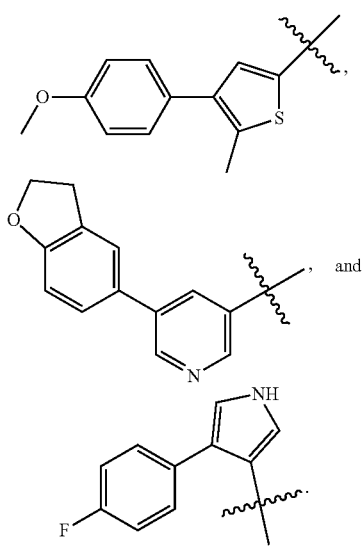

50B. The compound of embodiment 49B, wherein said compound is selected from the group consisting of

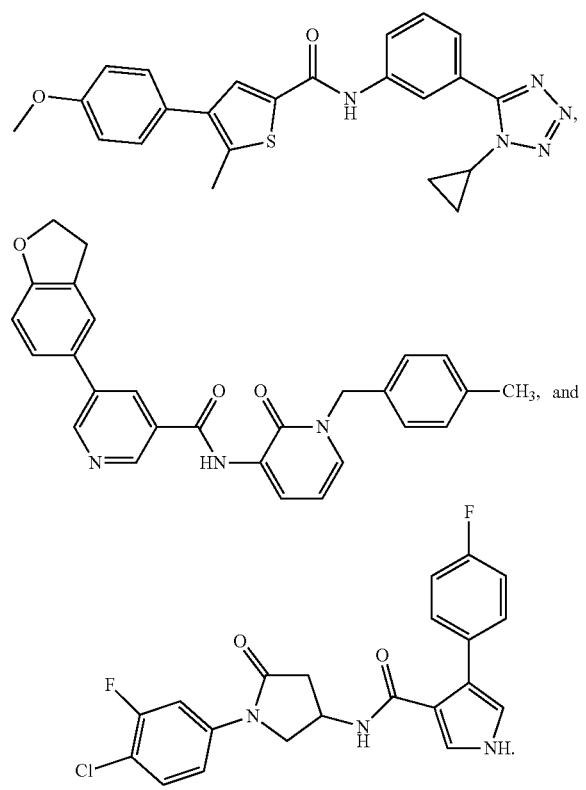

51B. The compound of embodiment 16B, wherein $R_5$ and $R_6$ are taken together with the nitrogen to which they are attached to form a heteroaryl or heterocyclo (C), wherein said heteroaryl or heterocyclo (C) is optionally substituted 1 to 3 times, in each instance, with one or a combination of branched or linear alkyl, hydroxyl, hydroxyalkyl, heteroaryl, aryl, arylalkyl, heterocyclo, halo, alkoxy, —(CH$_2$)$_j$NHC(O)-aryl, or —(CH$_2$)$_j$NHC(O)-heteroaryl (D), wherein said heteroaryl, aryl, heterocyclo, or arylalkyl (D) is optionally substituted 1 to 3 times, in each instance, with one or a combination of branched or linear alkyl, halo, haloalkoxy, hydroxyl, hydroxyalkyl, alkoxy, heteroaryl, or aryl (E), and wherein said heteroaryl or aryl (E) is optionally substituted 1 to 3 times, in each instance, with one or a combination of aryl, hydroxyl, alkoxy, branched or linear alkyl, haloalkoxy, or halo.

52B. The compound of embodiment 51B, wherein $R_5$ and $R_6$ are taken together with the nitrogen to which they are attached to form a 5-10-membered mono, bridged, fused, or spiro heterocyclo (C), wherein said heterocyclo (C) contains one or two heteroatoms, and wherein said heterocyclo is optionally substituted 1 to 3 times, in each instance, with one or a combination of aryl, arylalkyl, hydroxy, hydroxyalkyl, linear or branched $C_1$-$C_6$ alkyl, haloalkoxy, heteroaryl, heterocyclo, or —(CH$_2$)$_j$NHC(O)-heteroaryl (D), wherein said aryl, arylalkyl, heteroaryl, or heterocyclo (D) is optionally substituted 1 to 3 times, in each instance, with aryl, haloalkoxy, halo, or linear or branched $C_1$-$C_6$ alkyl (E), and wherein said aryl (E) is optionally substituted 1 to 3 times, in each instance, with one or a combination of linear or branched $C_1$-$C_3$ alkyl, alkoxy, or halo.

53B. The compound of embodiment 52B, wherein $R_5$ and $R_6$ are taken together with the nitrogen to which they are attached to form a pyrrolidinyl, piperidinyl, or morpholinyl ring (C), wherein said pyrrolidinyl, piperidinyl, or morpholinyl ring (C) is optionally substituted 1 to 3 times, in each instance, with one or a combination of aryl, arylalkyl, hydroxyl, hydroxyalkyl, linear or branched $C_1$-$C_6$ alkyl, haloalkoxy, heteroaryl, heterocyclo, or —CH$_2$NHC(O)-heteroaryl (D), wherein said aryl, arylalkyl, heteroaryl, or heterocyclo (D) is optionally substituted 1 to 3 times, in each instance, with one or a combination of aryl, haloalkoxy, halo, or linear or branched $C_1$-$C_6$ alkyl (E), and wherein said aryl (E) is optionally substituted 1 to 3 times, in each instance, with one or a combination of linear or branched $C_1$-$C_3$ alkyl, alkoxy, or halo.

54B. The compound of embodiment 53B, wherein $R_5$ and $R_6$ are taken together with the nitrogen to which they are attached to form a morpholinyl ring, wherein said morpholinyl ring is optionally substituted with phenyl, and wherein said phenyl ring is optionally substituted 1 to 3 times, in each instance, with methoxy, difluoromethoxy, trifluoromethoxy, or methyl.

55B. The compound of embodiment 54B, wherein $R_5$ and $R_6$ are taken together with the nitrogen to which they are attached to form a morpholinyl ring, wherein said morpholinyl ring is substituted once with phenyl, and wherein said phenyl ring is substituted once with difluoromethoxy.

56B. The compound of embodiment 55B, wherein $R_5$ and $R_6$ are taken together with the nitrogen to which they are attached to form

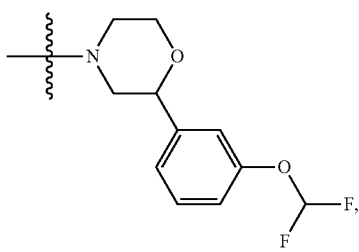 [SMILES: *N1CCOC(c2cccc(OC(F)F)c2)C1]

wherein ⁞ indicates the point of attachment to G.

57B. The compound of embodiment 53B, wherein $R_5$ and $R_6$ are taken together with the nitrogen to which they are attached to form a piperidinyl ring, wherein said piperidinyl ring is optionally substituted with imidazolyl, wherein said imidazolyl is optionally substituted with phenyl, and wherein said phenyl ring is optionally substituted 1 to 3 times, in each instance, with one or a combination of fluoro, chloro, methoxy, or methyl.

58B. The compound of embodiment 57B, wherein $R_5$ and $R_6$ are taken together with the nitrogen to which they are attached to form a piperidinyl ring, wherein said piperidinyl ring is substituted once with imidazolyl, wherein said imidazolyl is substituted once with phenyl, and wherein said phenyl is substituted once with fluoro.

59B. The compound of embodiment 58B, wherein $R_5$ and $R_6$ are taken together with the nitrogen to which they are attached to form

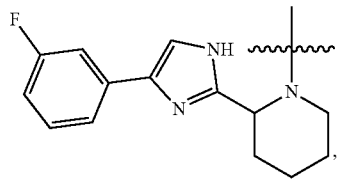 [SMILES: *N1CCCCC1c1nc(-c2cccc(F)c2)c[nH]1]

wherein § indicates the point of attachment to G.

60B. The compound of embodiment 53B, wherein $R_5$ and $R_6$ are taken together with the nitrogen to which they are attached to form a pyrrolidinyl ring, wherein said pyrrolidinyl ring is optionally substituted 1 to 3 times, in each instance, with one or a combination of hydroxyalkyl, linear or branched $C_1$-$C_6$ alkyl, benzyl, or —$CH_2NHC(O)$-heteroaryl, wherein said benzyl is optionally substituted one to three times, in each instance, with fluoro, chloro, methyl, or methoxy.

61B. The compound of embodiment 60B, wherein hydroxyalkyl is hydroxymethyl.

61bb. The compound of embodiment 60B, wherein $R_5$ and $R_6$ are taken together with the nitrogen to which they are attached to form a pyrrolidinyl ring, wherein said pyrrolidinyl ring is substituted once with hydroxymethyl and once with butyl.

61bb1. The compound of embodiment 61bb, wherein butyl is iso-butyl.

61bb2. The compound of embodiment 60B, wherein $R_5$ and $R_6$ are taken together with the nitrogen to which they are attached to form a pyrrolidinyl ring, wherein said pyrrolidinyl ring is substituted once with hydroxymethyl and once with benzyl, wherein said benzyl is substituted once with fluoro.

61bb3. The compound of embodiment 60B, wherein $R_5$ and $R_6$ are taken together with the nitrogen to which they are attached to form a pyrrolidinyl ring, wherein said pyrrolidinyl ring is substituted with once with methyl and once with —$CH_2NHC(O)$-heteroaryl.

61bb4. The compound of embodiment 61bb3, wherein said heteroaryl in —$CH_2NHC(O)$-heteroaryl is isoquinolinyl.

62B. The compound of embodiment 60B or 61B, wherein $R_5$ and $R_6$ are taken together with the nitrogen to which they are attached to form

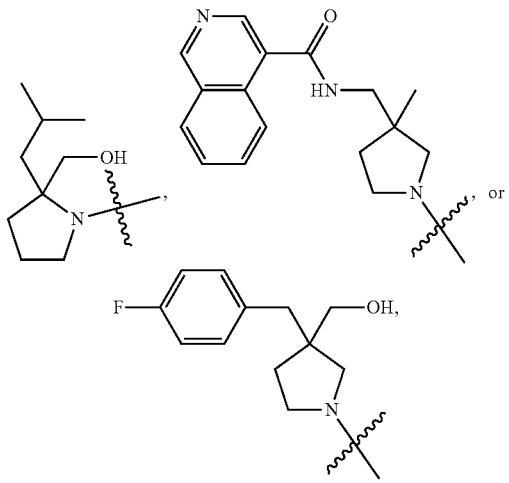

wherein § indicates the point of attachment to G.

63B. The compound of embodiment 52B, wherein $R_5$ and $R_6$ taken together with the nitrogen to which they are attached form a 9-membered spiro heterocyclo (C), wherein said spiro heterocyclo is

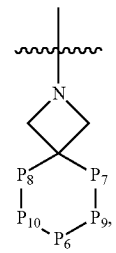

wherein $P_6$, $P_7$, $P_8$, $P_9$, and $P_{10}$ are each independently selected § from the group consisting of NH O, S, and $CH_2$, wherein § indicates the point of attachment to G, and wherein said spiro heterocyclo (C) is optionally substituted 1 to 3 times, in each instance, with aryl, hydroxy, hydroxyalkyl, linear or branched $C_1$-$C_6$ alkyl, haloalkoxy, heteroaryl, heterocyclo, or —$(CH_2)_j$NHC(O)-heteroaryl (D), and wherein said aryl, heteroaryl, or heterocyclo (D) is optionally substituted 1 to 3 times, in each instance, with haloalkoxy, halo, or linear or branched $C_1$-$C_6$ alkyl.

64B. The compound of embodiment 63B, wherein, $P_6$ is O and $P_7$, $P_8$, $P_9$, and $P_{10}$ are each $CH_2$.

65B. The compound of embodiment 63B or 64B, wherein said spiro heterocyclo is substituted with a heteroaryl, wherein said heteroaryl is further substituted with linear or branched $C_1$-$C_6$ alkyl.

66B. The compound of embodiment 65B, wherein said spiro heterocyclo is substituted with imidazolyl or pyrazolyl, and wherein said imidazolyl or pyrazolyl is substituted once with methyl, ethyl, propyl, butyl, pentyl, or hexyl.

66bb. The compound of embodiment 66B, wherein said spiro heterocyclo is substituted with pyrazolyl, wherein said pyrazolyl is substituted with butyl.

66bb1. The compound of embodiment 66bb, wherein said butyl is isobutyl.

67B. The compound of embodiment 66B, wherein said spiro heterocyclyl is

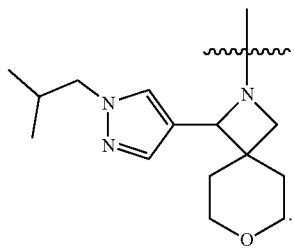 [SMILES: *N1CC2(CCOCC2)C1c1cnn(CC(C)C)c1]

69B. The compound of embodiment 68B, wherein ring M is

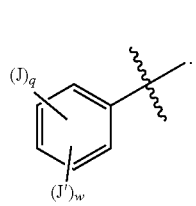

70B. The compound of embodiment 69B, wherein J' is heteroaryl.

71B. The compound of embodiment 70B, wherein J' is selected from the group consisting of pyrazolyl, pyrrolyl, imidazolyl, pyrimidinyl, and pyridinyl.

72B. The compound of embodiment 71B, wherein J' is pyrrolyl.

73B. The compound of embodiment 69B, wherein q is 0.

74B. The compound of embodiment 69B, wherein w is 1.

75B. The compound of embodiment 69B, wherein ring M is

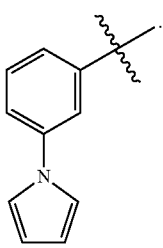 [SMILES: *c1cccc(-n2cccc2)c1]

76B. The compound of any one of embodiments 56B or 68B-75B, wherein the compound is

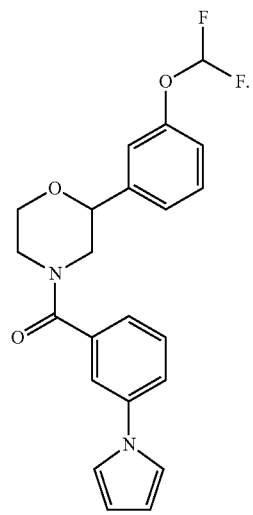 [SMILES: O=C(c1cccc(-n2cccc2)c1)N1CCOC(c2cccc(OC(F)F)c2)C1]

76bb. The compound of embodiment 59B, wherein ring M is

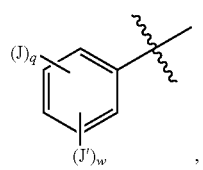

wherein J' is heteroaryl, wherein said heteroaryl is optionally substituted with linear or branched $C_1$-$C_3$ alkyl, and J is halo.

76bb1. The compound of embodiment 76bb, wherein J' is pyrazolyl, wherein said pyrazolyl is substituted once with methyl, and J is fluoro.

77B. The compound of any one of embodiments 59B, 76bb, or 76bb1, wherein ring M is

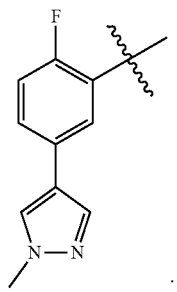 [SMILES: *c1cc(-c2cnn(C)c2)ccc1F]

78B. The compound of embodiment 77B, wherein the compound is

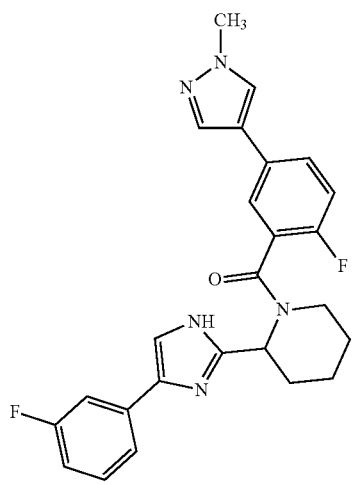

78bb. The compound of embodiment 62B, wherein ring M is

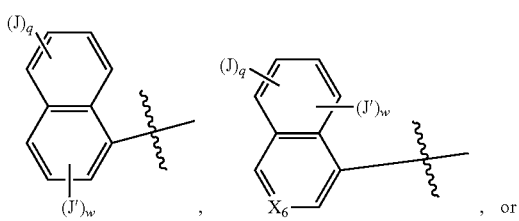, or

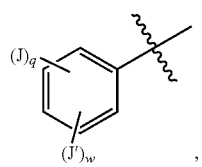, wherein J' is heteroaryl and J is selected from the group consisting of hydroxy and linear or branched $C_1$-$C_3$ alkyl.

78bb1. The compound of embodiment 78bb, wherein ring M is

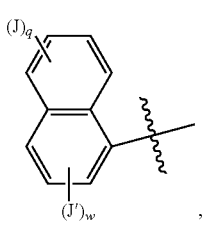, wherein w is 0, q is 1, and J is hydroxy.

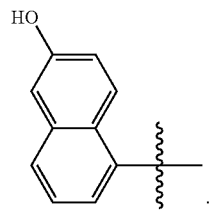

78bb2. The compound of embodiment 78bb1, wherein ring M is.

78bb3. The compound of embodiment 78bb, wherein ring M is

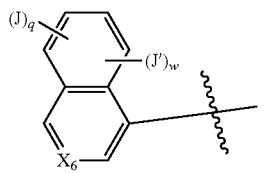, $X_6$ is N, and q and w are each 0.

78bb4. The compound of embodiment 78bb, wherein ring M is

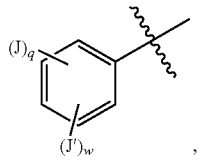, wherein J' is w is 1, q is 0, and J' is pyrrolyl.

78bb5. The compound of embodiment 78bb, wherein ring M is

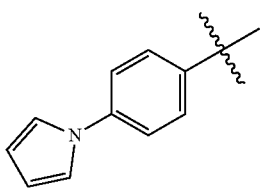.

79B. The compound of any one of embodiments 62B, 78bb, 78bb1, 78bb2, 78bb3, or 78bb4, wherein ring M is

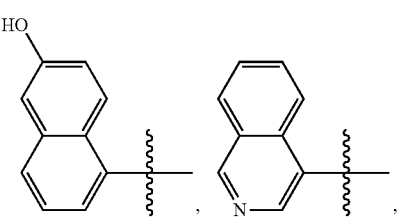, or

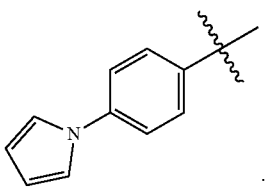 [SMILES: *c1ccc(-n2cccc2)cc1]

80B. The compound of embodiment 79B, wherein the compound is selected from the group consisting of

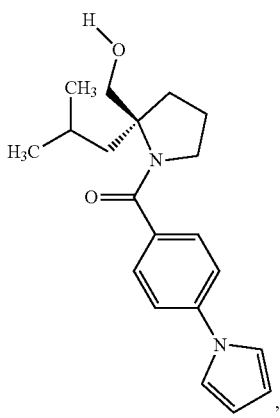

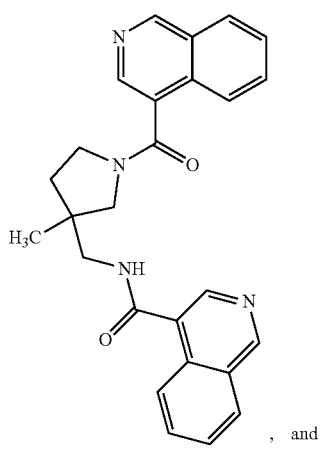

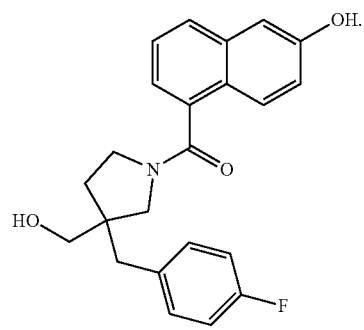

80bb. The compound of embodiment 67B, wherein ring M is

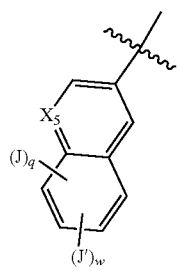

wherein J and J' are each halo.

80bb1. The compound of embodiment 80bb, wherein $X_5$ is N, J and J' are each fluoro, and w and q are each 1.

81B. The compound of any one of embodiments 67B, 80bb, or 80bb1, wherein ring M is

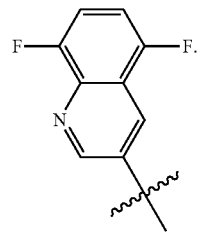

82B. The compound of embodiment 81B, wherein the compound is

83B. The compound of embodiment 1B, where P is S.

84B. The compound of embodiment 83B, wherein G is C=O.

85B. The compound of embodiment 84B, wherein y is 1.

86B. The compound of any one of embodiments 83B-85B, where $R_5$ is taken together with the nitrogen to which it is attached and G, D, and one of $R_3$ and $R_4$ to form a heterocyclo.

87B. The compound of embodiment 86B, wherein said heterocyclo is a 5- or 6-membered heterocyclo containing one or two heteroatoms.

88B. The compound of embodiment 87B, wherein $R_6$ is selected from the group consisting of aryl, heteroaryl, heterocyclo, and cycloalkyl, wherein said aryl, heteroaryl, heterocyclo, or cycloalkyl is optionally substituted 1 to 3 times, in each instance, with one or a combination of linear or branched $C_1$-$C_3$ alkyl, hydroxyl, alkoxy, or halo.

89B. The compound of embodiment 88B, wherein R₆ is aryl, optionally substituted 1 to 3 times, in each instance, with alkoxy or hydroxyl.

90B. The compound of embodiment 89B, wherein R₆ is phenyl, optionally substituted 1 to 3 times with methoxy.

91B. The compound of c embodiment 90B, wherein R₆ is

92B. The compound of any one of embodiments 83B-91B, wherein ring M is wherein $X_9$ and $X_{10}$ are each N and $X_8$ is selected from the group consisting of NH and O.

93B. The compound of embodiment 92B, wherein ring M is wherein $X_8$ is O and $X_9$ and $X_{10}$ are each N.

94B. The compound of embodiment 93B, wherein J' is $C_6$-$C_{10}$ aryl.

95B. The compound of embodiment 94B, wherein J' is naphthalenyl.

96B. The compound of embodiment 93B, wherein w is 1.

97B. The compound of embodiment 93B, wherein q is 0.

98B. The compound of any one of embodiments 92B-97B, wherein ring M is

99B. The compound of embodiment 98B, wherein said compound is

100B. The compound of embodiment 3B, wherein ring M is

101B. The compound of embodiment 100B, wherein J' is selected from the group consisting of aryl, heteroaryl, and heterocyclo, wherein said aryl, heteroaryl, or heterocyclo is optionally substituted 1 to 3 times, in each instance, with one or a combination of alkoxy, linear or branched $C_1$-$C_3$ alkyl, halo, hydroxyl, or cyano.

102B. The compound of embodiment 101B, wherein J' is aryl, optionally substituted once with cyano, methyl, hydroxyl, or methoxy.

103B. The compound of embodiment 102B, wherein J' is phenyl, substituted with cyano.

104B. The compound of embodiment 103B, wherein q is 0.

105B. The compound of embodiment 104B, wherein ring M is

106B. The compound of any one of embodiments 100-105, wherein P is a bond.

107B. The compound of embodiment 106B, wherein G is CH₂.

108B. The compound of embodiment 107B, wherein y is 0.

109B. The compound of any one of embodiments 106B-108B, wherein R₅ is selected from the group consisting of hydroxyalkyl, hydrogen, halo, and alkoxy.

110B. The compound of embodiment 109B, wherein R₅ is hydroxyalkyl.

111B. The compound of embodiment 110B, wherein $R_5$ is selected from the group consisting of hydroxymethyl, hydroxyethyl, hydroxypropyl, and hydroxybutyl.

112B. The compound of any one of embodiment 109B-111B, wherein $R_6$ is selected from the group consisting of halo, linear or branched $C_1$-$C_6$ alkyl, haloalkyl, alkenyl, and alkynyl.

113B. The compound of embodiment 112B, wherein $R_6$ is linear or branched $C_1$-$C_6$ alkyl.

114B. The compound of embodiment 113B, wherein $R_6$ is selected from the group consisting of methyl, ethyl, n-propyl, iso-propyl, n-butyl, sec-butyl, iso-butyl, tert-butyl, n-pentyl, isopentyl, neopentyl, and n-hexyl.

115B. The compound of embodiment 114B, wherein $R_6$ is neopentyl.

116B. The compound of embodiment 115B, wherein said compound is

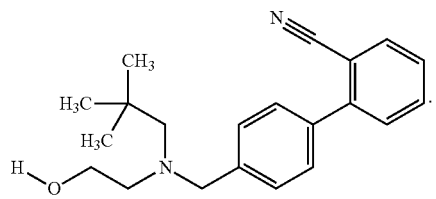 [SMILES: CC(C)(C)CN(CCO)Cc1ccc(-c2ccccc2C#N)cc1]

117B. The compound of any one of embodiments 1A-64A or 1B-116B, wherein the compound is selected from the group consisting of:

| Compound No. | Structure |
| --- | --- |
| RTX57548183 (Compound 1) | 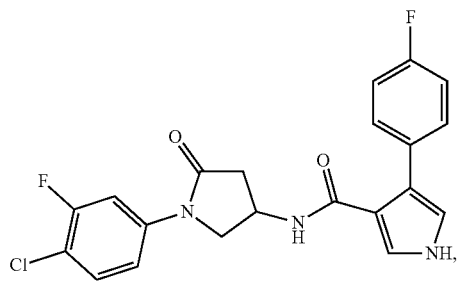 |
| RTX06107454 (Compound 2) | 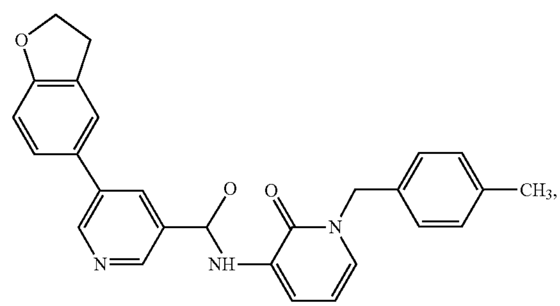 [SMILES: Cc1ccc(Cn2cccc(NCOCc3cncc(-c4ccc5c(c4)CCO5)c3)c2=O)cc1] |
| RTX60933293 (Compound 3) | 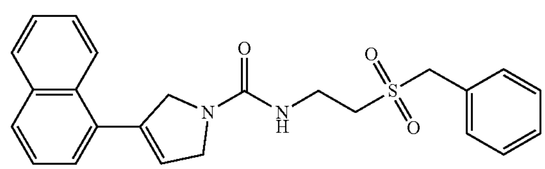 |
| RTX26466486 (Compound 4) | 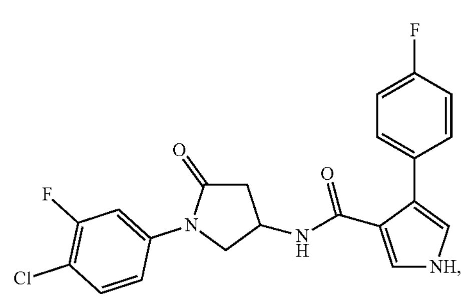 [SMILES: O=C(NC1CC(=O)N(c2ccc(Cl)c(F)c2)C1)c1c[nH]cc1-c1ccc(F)cc1] |

-continued

| Compound No. | Structure |
|---|---|
| RTX73145433 (Compound 5) | 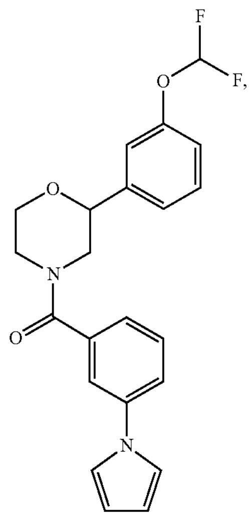 [SMILES: O=C(c1cccc(-n2cccc2)c1)N1CCOC(c2cccc(OC(F)F)c2)C1] |
| RTX45332746 (Compound 6) | 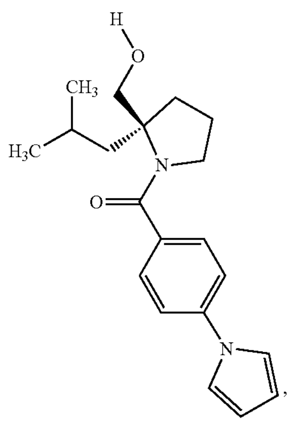 [SMILES: CC(C)C[C@]1(CO)CCCN1C(=O)c1ccc(-n2cccc2)cc1] |
| RTX04306230 (Compound 7) | 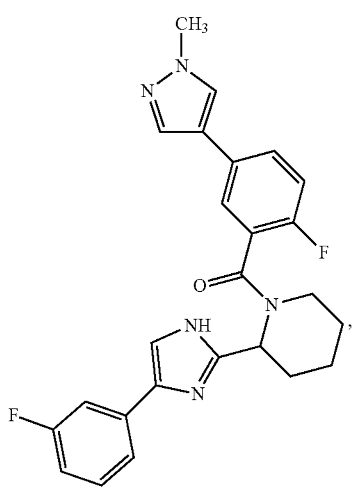 [SMILES: Cn1cc(-c2ccc(F)c(C(=O)N3CCCCC3c3nc(-c4cccc(F)c4)c[nH]3)c2)cn1] |

-continued

| Compound No. | Structure |
|---|---|
| RTX70558122 (Compound 8) | 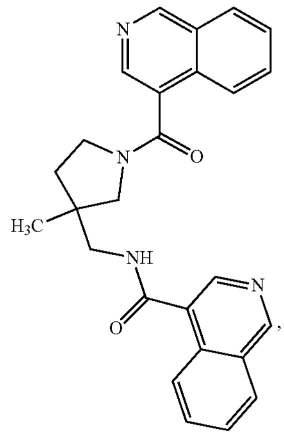 [SMILES: CC1(CNC(=O)c2cncc3ccccc23)CCN(C(=O)c2cncc3ccccc23)C1] |
| RTX95655369 (Compound 9) | 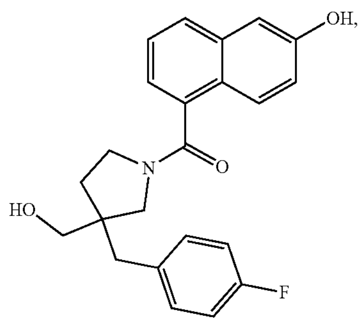 [SMILES: O=C(c1cccc2cc(O)ccc12)N1CCC(CO)(Cc2ccc(F)cc2)C1] |
| RTX71280707 (Compound 10) | 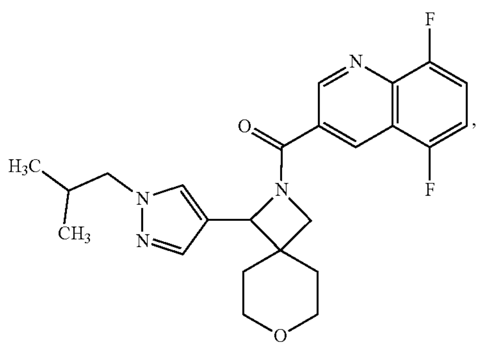 [SMILES: CC(C)Cn1cc(C2N(C(=O)c3cnc4c(F)ccc(F)c4c3)CC23CCOCC3)cn1] |
| RTX89483884 (Compound 11) | , and |

| Compound No. | Structure |
| --- | --- |
| RTX24380616 (Compound 12) | 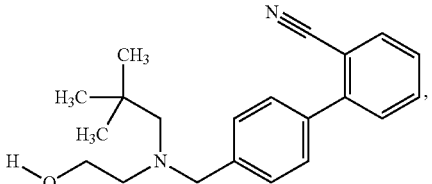 | or a pharmaceutically acceptable salt thereof.

118B. A pharmaceutical composition comprising a compound or pharmaceutically acceptable salt thereof of any one of embodiments 1A-64A or 1B-116B, and a carrier acceptable for human administration.

119B. The pharmaceutical composition of embodiment 118B, formulated for oral administration.

120B. The pharmaceutical composition of embodiment 118B, formulated as a pill or capsule.

121B. The pharmaceutical composition of embodiment 118B, formulated for parenteral administration.

122B. The pharmaceutical composition of embodiment 118B, packaged in a vial containing a unit dose of the compound.

123B. A method of treating or effecting prophylaxis of impaired insulin sensitivity, glucose tolerance, or obesity, comprising administering to a subject having the impaired insulin sensitivity, glucose tolerance, or obesity an effective regime of a compound or pharmaceutical composition of any one of embodiments 1A-64A or 1B-116B.

124B. The method of embodiment 123B, wherein the subject has type 2 diabetes.

125B. The method of embodiment 123B, wherein the subject has a body mass index of at least 30.

126B. The method of embodiment 123B, wherein the subject is obese.

127B. The method of embodiment 123B, wherein the subject has impaired insulin sensitivity and/or glucose tolerance.

128B. The method of embodiment 123B, wherein the subject has hyperglycemia.

129B. The method of embodiment 123B, wherein the subject has dyslipidemia.

130B. The method of embodiment 123B, wherein the subject has microalbuminuria.

131B. A method of treating a subject having non-alcoholic fatty liver disease (NAFLD), comprising administering to the subject an effective regime of a compound of any one of embodiments 1A-64A or 1B-116B.

132B. The method of embodiment 131B, wherein the subject has nonalcoholic steatohepatitis (NASH).

133B. The method of embodiment 131B, wherein the subject has fibrosis.

134B. The method of embodiment 131B, further comprising monitoring the subject for change(s) in sign(s) and/or symptom(s) of NAFLD responsive to administering the compound.

135B. A method of treating a subject having nonalcoholic steatohepatitis (NASH) comprising administering to the subject an effective regime of a compound of any one of embodiments 1A-64A or 1B-116B.

136B. The method of embodiment 135B, wherein the subject has fibrosis.

137B. The method of embodiment 135B, further comprising monitoring the subject for change(s) in sign(s) and/or symptom(s) of NASH responsive to administering.

138B. A method of treating a subject having primary sclerosing cholangitis (PSC) comprising administering to the subject an effective regime of a compound of any one of embodiments 1A-64A or 1B-116B.

139B. A method of treating a subject having primary biliary cholangitis (PBC) comprising administering to the subject an effective regime of a compound of any one of embodiments 1A-64A or 1B-116B.

140B. A method of inhibiting beta amyloid toxicity in a subject, comprising administering to a subject in need thereof an effective regime of a compound of any one of embodiments 1A-64A or 1B-116B.

The following examples are offered by way of illustration and not by way of limitation.

EXAMPLES

Example 1: Assay Results of Novel Compounds

Unless indicated otherwise, all cells were incubated at 37° C. in 5% $CO_2$.

Example 1A: Screening of Compounds for Protection of Primary Hepatocytes from Palmitate Toxicity Primary hepatocytes were isolated from 3-month-old C57Bl6 male mice and plated onto Nunc 384-well polystyrene black 384 well plates, Cat #164564 (Thermo Fisher Scientific, Rochester, N.Y.), 2,000 cells per well, in DMEM 10% FBS, 25 mM glucose medium, and were allowed to attach for 3 hours. Media was replaced with DMEM 1% FBS, 0.2 nM insulin, and compounds were supplemented to 1 uM and 10 uM; palmitate was supplemented to 200 mM. Cells were incubated for 24 hours, washed with Calcein-AM DW assay buffer, Cat #4892-010-02 (Trevigen, Gaithersburg, Md.), and stained with Calcein AM, Cat #4892-010-01 (Trevigen, Gaithersburg, Md.) according to manufacturer instructions; fluorescence was measured using 490Ex/ 520Em wavelengths. Hits were identified as 2 Standard Deviations different from the assay mean, and exhibited a 10% false discovery rate estimate. Each compound was tested 28 times at 1 uM and 28 times at 10 uM concentrations. The number of times a compound was a significant hit was counted and plotted.

Example 1B: Screening of Compounds for Protection of Primary Hepatocytes from Alcohol Toxicity Primary hepatocytes were isolated from 3-month-old C57Bl6 male mice and plated onto Nunc 384-well polystyrene black 384 well plates, Cat #164564 (Thermo Fisher Scientific, Rochester, N.Y.), 2,000 cells per well, in DMEM 10% FBS, 25 mM glucose medium, and were allowed to attach for 3 hours. Media was replaced with DMEM 1% FBS, 0.2 nM insulin, and compounds were supplemented to 1 uM and 10 uM; alcohol was supplemented to 720 mM. Cells were incubated for 48 hours. Calcein-AM staining was performed as described above. Hits were identified as 2 Standard Deviations different from the assay mean, and had a 10% false discovery rate estimate. Each compound was tested 16 times at 1 uM and 16 times at 10 uM concentrations. The number of times a compound was a significant hit was counted and plotted.

Example 1C: Screening of Compounds for Protection from Amyloid Beta Toxicity in N2A Neuronal Cell Line The N2A cells were seeded onto Nunc 384-well polystyrene black 384 well plates, Cat #164564 (Thermo Fisher Scientific, Rochester, N.Y.), 7,000 cells per well, in 50% DMEM 50% OptiMEM 5% FBS, 25 mM glucose medium, and allowed to attach for 24 hours. Media was replaced with FBS free DMEM, 0 glucose; compounds were supplemented to 1 uM and 10 uM; aged amyloid beta was supplemented to 50 mM; cells were incubated for 72 hours; Calcein-AM staining was performed as described above. Hits were identified as 2 Standard Deviations different from the assay mean, and had a 10% false discovery rate estimate. Each compound was tested 8 times at 1 uM and 16 times at 10 uM concentrations. The number of times a compound was a significant hit was counted and plotted.

The results of all HTS for protection from palmitate, alcohol, beta-amyloid, HTS insulin sensitization, binding to p52Shc-PTB domain, affinity, and chemical scaffolding information were compared. The selected compounds were tested for insulin sensitization potency by measuring the insulin sensitivity of FL83B liver cells in the presence of 2 mM compounds and 0.1 nM insulin, as described below.

Example 1D: Insulin Sensitization Potency

The liver cell line FL83B was plated onto 24 well plates, 200,000 cells per well in 1 ml of DMEM-F12 10% FBS, 25 mM glucose medium, and allowed to grow for 48 hours. The media was changed to FBS-free DMEM-F12 25 mM glucose, and cells were incubated for 16 hours. Compounds were supplemented to 2 uM concentration in duplicates, and cells were incubated for 1 hour and stimulated with 0.1 nM insulin for 10 minutes. Cells were lysed with CelLytic MT Cell Lysis Reagent, Cat #3228-500 ML (Sigma, St. Louis, Mass.); lysates were analyzed with the Simple Western Capillary Electrophoresis instrument "Jess," Cat #004-650 (Protein Simple, Santa Clara, Calif.) for insulin-dependent activation of P-Akt with anti-Akt (pan) (40D4) Mouse monoclonal Antibody, Cat #2920 (Cell Signaling Technology Inc., Danvers, Mass.), anti-Phospho-Akt (Ser473) (193H12) Rabbit monoclonal Antibody, Cat #4058 (Cell Signaling Technology Inc., Danvers, Mass.), anti-beta actin antibody mouse monoclonal antibody, Cat #MAB8929 (R&D Systems, Minneapolis, Minn.); dilution factors were 50, 50, 100 respectively. The signals were normalized to total protein loaded on each capillary using protein normalization staining for Protein Capillary Electrophoresis, Cat #AM-PN01 (Protein Simple, Santa Clara, Calif.), the fold changes of insulin dependent P-Akt activation over vehicle were determined and plotted. No changes in total Akt or Actin were detected for any compounds (FIG. 2).

Provided in FIG. 1 and FIG. 2 are assay results exhibiting the effectiveness of the compounds in Shc protein binding, affinity in KD, Potency of insulin sensitization, potency of hepatocyte protection in palmitate assays in hepatocyte cell lines and in mouse hepatocytes ex vivo, hepatoprotection in the context of alcohol toxicity, and protection of neurons in the context of beta-amyloid toxicity.

Figure 3:
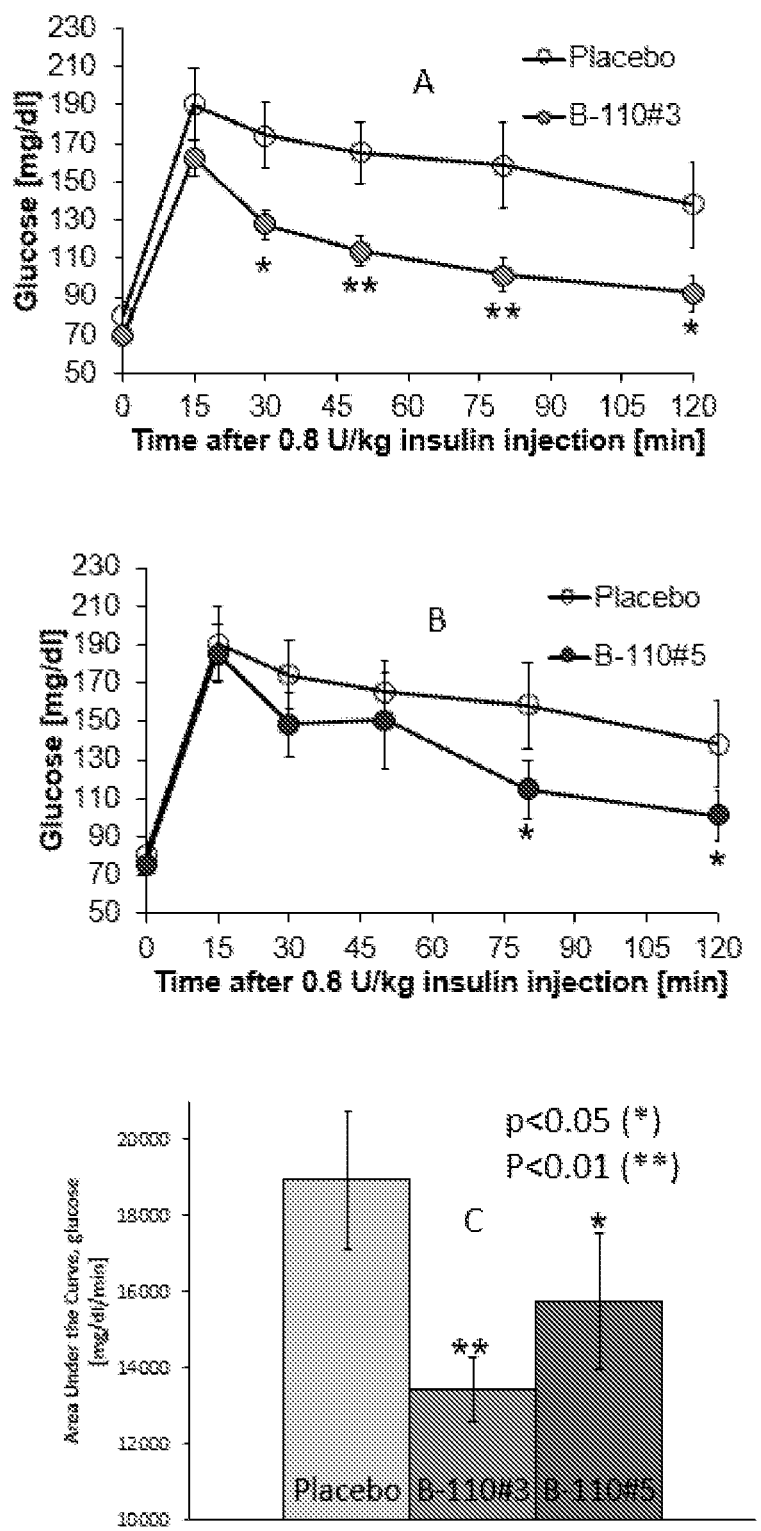
FIG. 3 shows how compound 3 and compound 5 reduce glucose intolerance in the Corticosterone model of Insulin resistance. In a standard model of glucose intolerance and insulin insensitivity, corticosterone (CS) was dosed for 21 days, and in the drug treated group mice were administered Shc Blocker #3=RTX60933293 or #5=RTX73145433 at a dose of 10 mg/kg i.p. for the final 5 days of the 21-day CS treatment. As seen in (A) by the standard GTT=Glucose Tolerance Test, compound number 3 reduced glucose intolerance significantly at 4 time points after glucose administration; (B), compound number 5 reduced glucose significantly at 2 time points after glucose administration, and (C) Area Under the Curve (AUC) analysis demonstrates that both molecules significantly reduced glucose intolerance relative to the placebo.

Example 1E: Novel Shc Blockers Make Insulin-Resistant Animals More Glucose-Tolerant By blocking the interaction of Shc protein with phosphotyrosines on the Insulin Receptor, a Shc blocker redirects more signaling to the insulin-sensitizing and glucose tolerizing phospho-Akt. Thus, peripheral cells become more sensitive per molecule insulin, and consequently more glucose tolerant. This prediction is borne out in the Corticosteroid model. Corticosterone is a known model of Type 2 Diabetes and Metabolic Syndrome, as Corticosterone induces peripheral insulin insensitivity. As shown in FIG. 3, both compound 3=RTX60933293 and compound 5=RTX73145433 are significantly glucose tolerizing.

Example 1F: Novel Shc Blockers Reduce Liver Fibrosis in NASH Models

Figure 4:
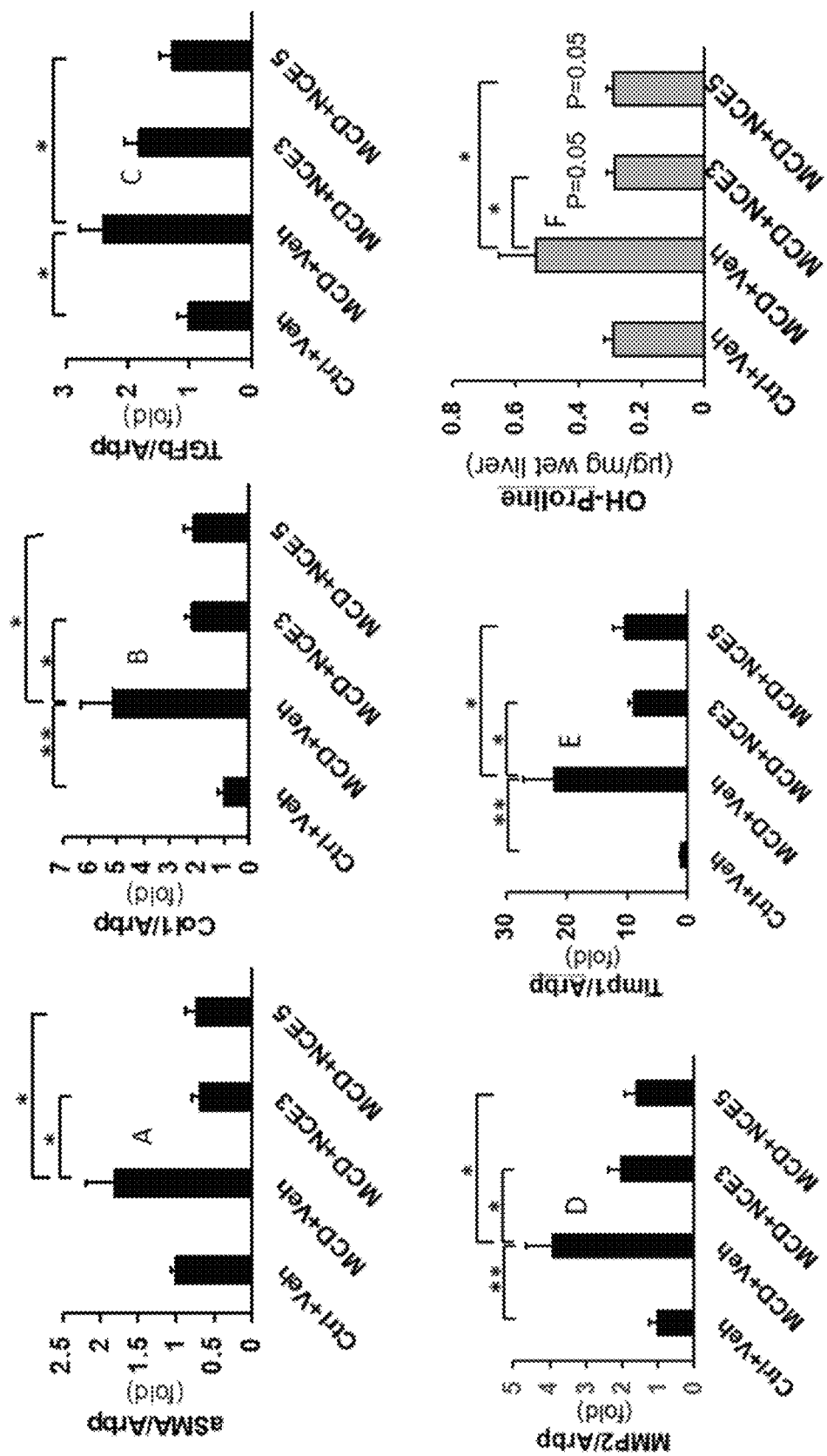
FIG. 4 shows how Shc Blocker compound number 3 and compound number 5 inhibit fibrosis in a MCD model of Non-alcoholic Steatohepatitis (NASH). Mice were fed the Liver fibrosis-inducing Methionine Choline-Deficient (MCD) Mouse model NASH for 8 weeks, and the last 4 weeks they were dosed orally with 20 mg/kg of compound number 3 (RTX60933293), compound number 5 (RTX73145433), or placebo. After 8 weeks of MCD dosing, mice were sacrificed, and livers were extracted for nucleic acids and classical markers of liver fibrosis were assayed by QRTPCR. In this treatment regimen, compounds 3 and 5 significantly reduced many standard markers of NASH liver fibrosis, including: (A), alpha-smooth muscle actin (aSMA); (B), Collagen 1a1 (Col1); (C), Transforming Growth Factor beta (TGF-b); (D), Matrix Metalloproteinase 2 (MMP2); and (E), Tissue metallopeptidase inhibitor 1 (TIMP1). In addition, the classical liver fibrosis bio marker hydroxyproline was measured, and both compounds 3 and 5 significantly reduced this marker. *=p<0.05; **=p<0.01

Without wishing to be bound by theory, NASH could be considered the next-most common metabolic disturbance after Type 2 Diabetes in the USA, and currently has no approved treatment. There is a usual progression from NAFLD (fatty liver) to the more fibrotic/cirrhotic NASH. While the precise mechanism of the transition of NAFLD to NASH is not completely understood, hepatocyte death and resulting fibrosis has been proposed. Fibrosis and fibrotic scarring are thought to be the most important pathophysiological endpoints to end-stage NASH, which typically necessitates an expensive and difficult liver transplant. As shown in other examples, Shc blockers through their sensitization to insulin, IGF-1 and other growth factors, are cytoprotective. Thus, by inhibiting hepatocyte death which promotes fibrosis, they should also be anti-fibrotic. Furthermore, as shown in FIG. 4, when fed to mice on the strongly liver fibrotic MCD diet, Shc blockers significantly reduced 6 out of 6 biomarkers of liver fibrosis, which suggests that they could be of benefit in human liver fibrosis.

Example 2: Synthetic Preparation of Compounds of Formula II
Example 2A: Preparation of RTX73145433 (Compound 5)
Scheme 1 depicts the preparation of an exemplary compound.
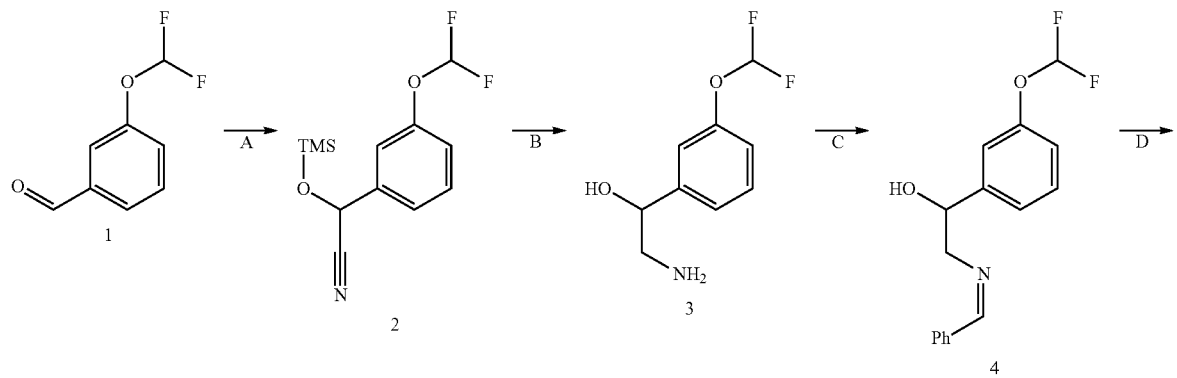
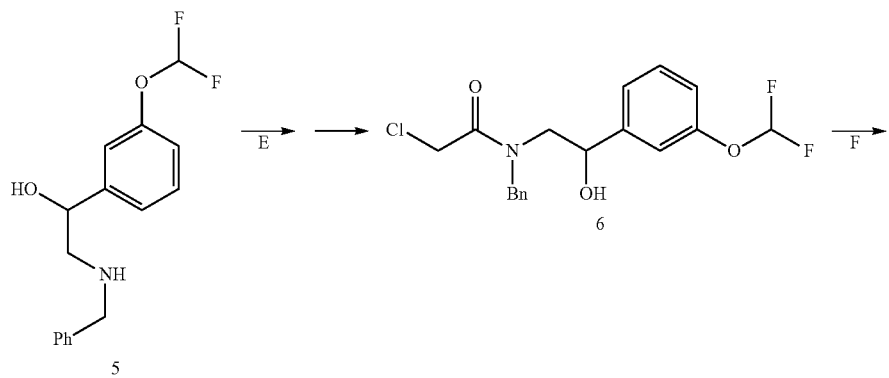
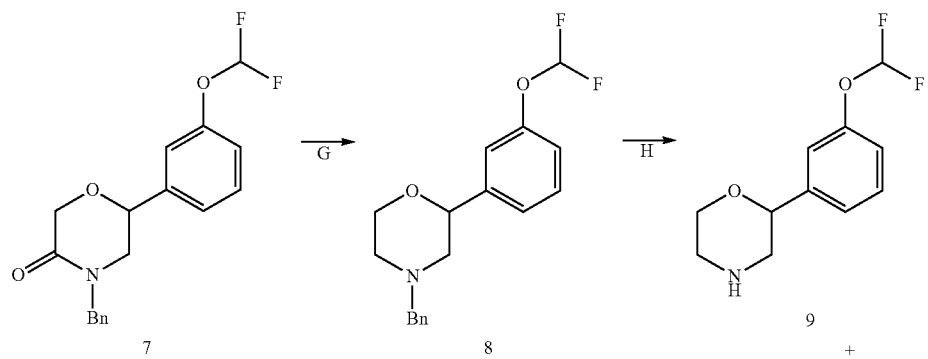

-continued

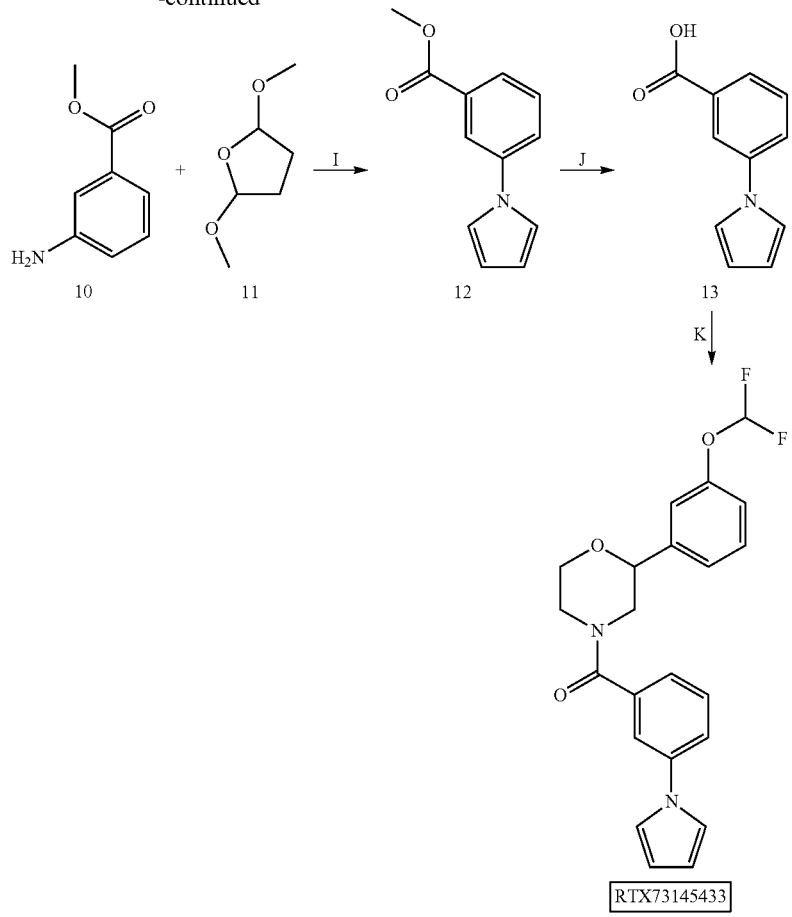

Step A: TMSCN, SnI$_2$, in Et$_2$O. 18 h, rt (Linn, J. A. et al. PCT Int. Appl., 2008024634).

Step B: a) LiAlH$_4$, in Et$_2$O, 20 min, reflux; 3 h, reflux; b) NaOH, in H$_2$O (Linn, J. A. et al. PCT Int. Appl., 2008024634).

Step C: EtOH, 2 h, rt; rt→0° C. (Yang, X. et al. *Journal of the American Chemical Society,* 134(42), 17605-17612; 2012).

Step D: NaBH$_4$, 0° C.; 1 h, 0° C.; b) NaOH, in H$_2$O; c) HCl, in H$_2$O (Yang, X. et al. *Journal of the American Chemical Society,* 134(42), 17605-17612; 2012).

Step E: Et$_3$N, in CH$_2$Cl$_2$, 1 h, 0° C. (Iwema Bakker, W. I. et al. PCT Int. Appl., 2011023795).

Step F: R:KOH, in i-PrOH, 3 h, rt (Iwema Bakker, W. I. et al. PCT Int. Appl., 2011023795).

Step G: a) BH$_3$-THF, in THF, 0° C.; 1 h, 0° C.; 0° C.→rt; 2 h, rt; b) MeOH, 0° C.; 30 min, rt; c) NaOH, in H$_2$O-MeOH, 1 h, reflux (Iwema Bakker, W. I. et al. PCT Int. Appl., 2011023795).

Step H: H$_2$, Pd(OH)$_2$, in MeOH, overnight, rt (Iwema Bakker, W. I. et al. PCT Int. Appl., 2011023795).

Step I: AcOH, 10 min, 170° C. (Brindisi, M. et al. *Future Medicinal Chemistry,* 8(13), 1573-1587; 2016).

Step J: NaOH, in H$_2$O-MeOH, 12 h, 25° C.; b) HCl, in H$_2$O, 25° C. (Brindisi, M. et al. Future Medicinal Chemistry, 8(13), 1573-1587; 2016).

Step K: EDC, HOBT, in DMF, rt, 24 h.

Example 2B: Preparation of RTX60933293 (Compound 3)

Scheme 2 depicts the preparation of an exemplary compound.

Scheme 2
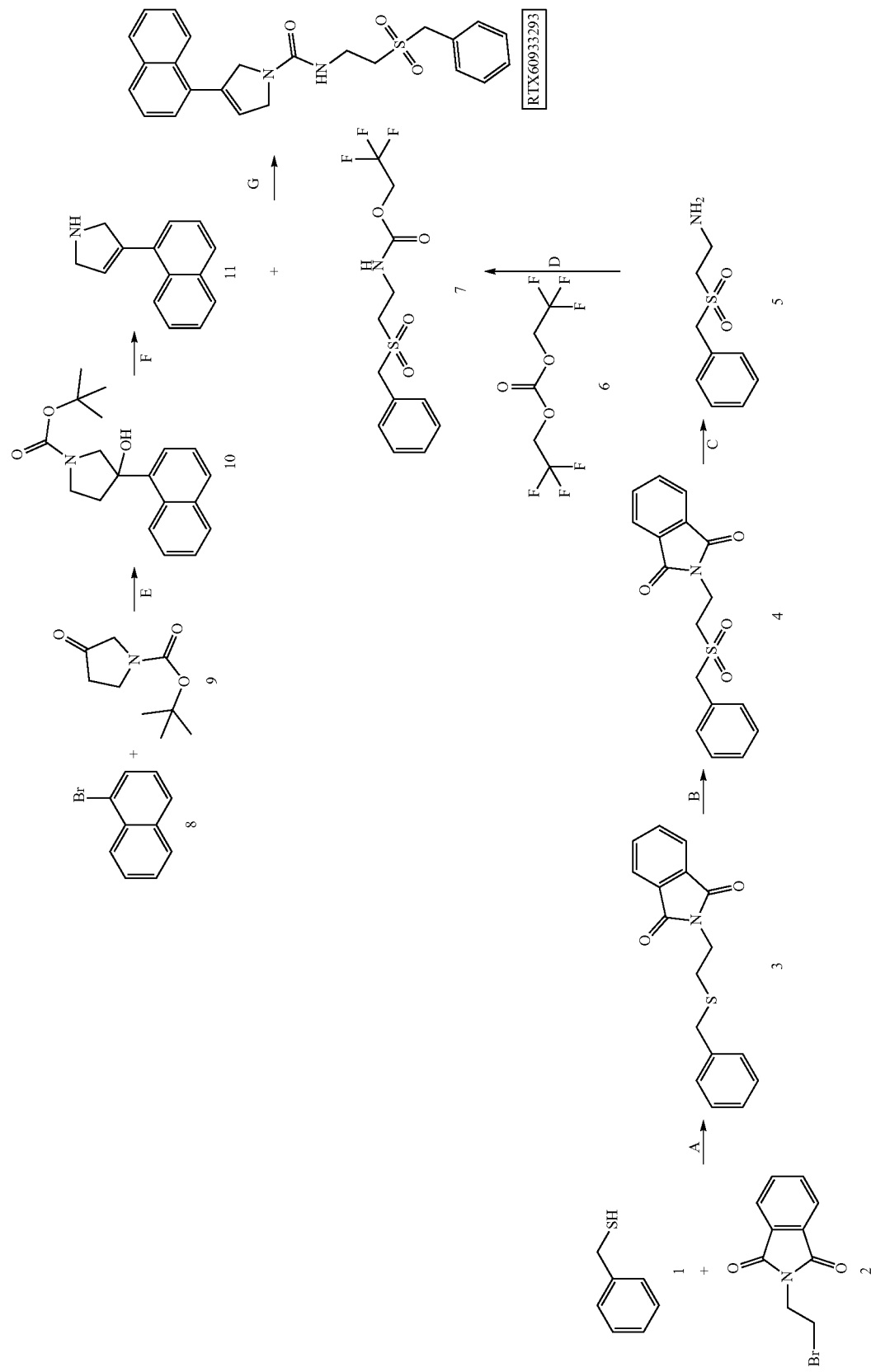

Step A: Et₃N, in DMF, 1 h, rt (Sami, S. M. et al. *Journal of Medicinal Chemistry*, 32(3), 703-8; 1989).

Step B: H₂O₂, in H₂O—AcOH, 0° C.; 2 h; b) Na₂SO₃, in H₂O, rt (Kilburn, John Paul et al. PCT Int. Appl., 2007051811).

Step C: N₂H4-H₂O, in EtOH—CHCl₃, 0° C.; overnight, rt (Kilburn, John Paul et al. PCT Int. Appl., 2007051811).

Step D (in situ): in DMF, rt, 1 h (Bogolubsky, A. V. et al. ACS Combinatorial Science (2014), 16(6), 303-8).

Step E: Mg, in THF, reflux, 2 h; b) in Et₂O; rt, overnight; b) NH₄C₁, in H₂O (Pinkerton, Anthony et al. PCT Int. Appl., 2014100501).

Step F: HCl in H₂O (Lee, Y. et al. *Journal of the American Chemical Society*, 124(41), 12135-12143; 2002).

Step G: DBU, in DMF, rt, 4 h (Bogolubsky, A. V. et al. ACS Combinatorial Science (2014), 16(6), 303-8).

Example 2C: Preparation of RTX04306230 (Compound 7)

Scheme 3 depicts the preparation of an exemplary compound.

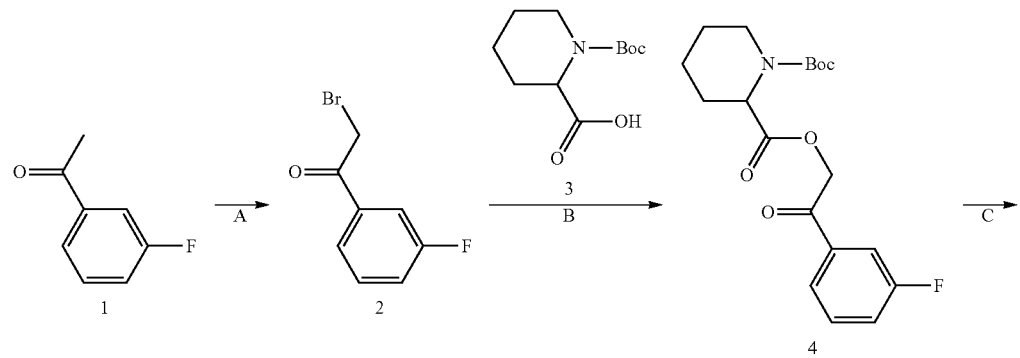

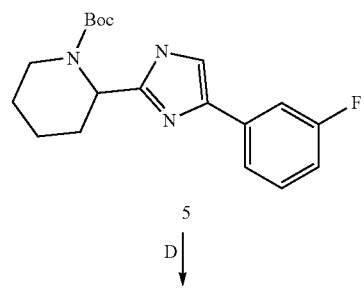

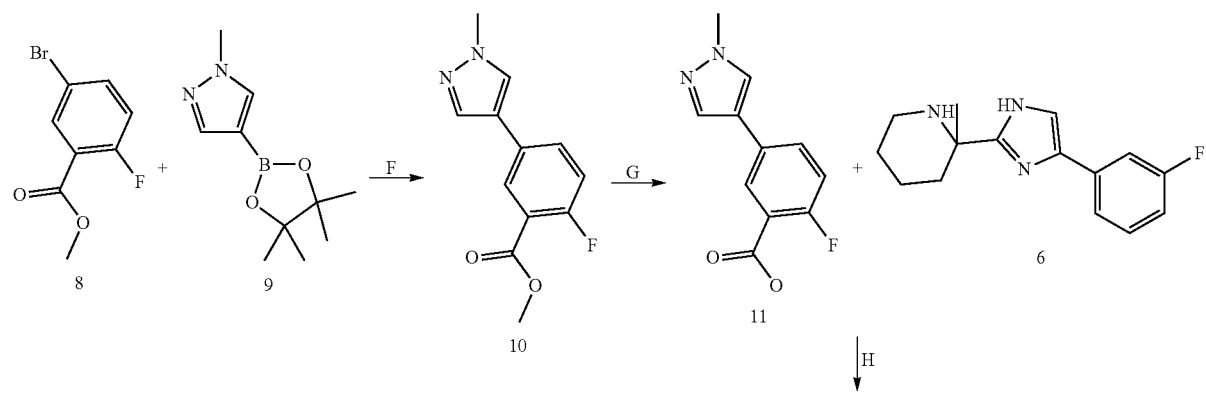

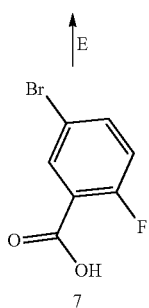

7

-continued

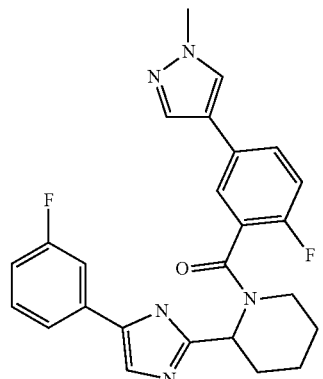

Step A: Br$_2$, in CHCl3, at 20° C. (LABORATORIOS ALMIRALL, S.A. WO200846598, 2008, A1).

Step B: DIPEA, in MeCN, rt, overnight (Zhang, Yang et al, PCT Int. Appl., 2015124063).

Step C: NH$_4$OAc, in PhMe, reflux overnight (Zhang, Yang et al. PCT Int. Appl., 2015124063).

Step D: TFA, in CH$_2$Cl$_2$, 0° C.; 4 h, rt (Zhang, Yang et al. PCT Int. Appl., 2015124063).

Step E: SOCl$_2$, in CH$_2$Cl$_2$, 3.5 h, rt→85° C.; b) MeOH, rt, 30 min (Corte, J. et al. PCT Int. Appl., 2005123680).

Step F: Pd(PPh$_3$)$_4$, Na$_2$CO$_3$, in dioxane-H$_2$O, 90° C., 8 h (Jones, Alison et al. PCT Int. Appl., 2016156816).

Step G: LiOH, S:THF—H$_2$O, rt, 3 h (Jones, Alison et al. PCT Int. Appl., 2016156816).

Step H: EDC, HOBT, in DMF, rt, 24 h.

What is claimed is:

1. A compound of Formula II:

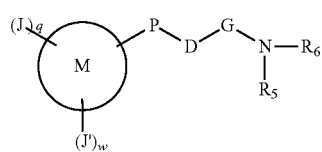

(II)

wherein,
Ring M, J, J', q, and w form

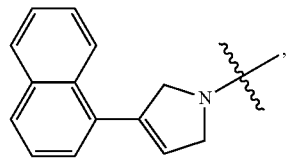

wherein J' is naphthalenyl, w is 1, and q is 0;
P is a bond;
D is absent;
G is C=O;
R$_5$ is selected from the group consisting of hydrogen, hydroxyl, and linear or branched C$_1$-C$_3$ alkyl;
R$_6$ is selected from the group consisting of alkyl-S(O)$_m$, haloalkyl-S(O)$_m$, alkenyl-S(O)$_m$, alkynyl-S(O)$_m$, cycloalkylalkyl-S(O)$_m$, aryl-S(O)$_m$, arylalkyl-S(O)$_m$, heterocycloalkyl-S(O)$_m$, and heteroaryl-S(O)$_m$, wherein S in —S(O)$_m$ is optionally substituted 1 to 3 times, in each instance, with arylalkyl, aryl, heterocyclo, or heteroaryl; and m is 1, 2 or 3;

or a pharmaceutically acceptable salt thereof.

2. The compound of claim 1, wherein R$_5$ is hydrogen.

3. The compound of claim 1, wherein R$_6$ is alkyl-S(O)$_m$, wherein S in S(O)$_m$ is optionally substituted 1 to 3 times, in each instance, with one or a combination of arylalkyl, aryl, or heteroaryl.

4. The compound of claim 3, wherein m is 2.

5. The compound of claim 3, wherein R$_6$ is alkyl-S(O)$_2$, wherein S is substituted once with aryl or arylalkyl.

6. The compound of claim 5, wherein R$_6$ is alkyl-S(O)$_2$, wherein S is substituted once with arylalkyl.

7. The compound of claim 6, wherein R$_6$ is —CH$_2$CH$_2$—S(O)$_2$, wherein S is substituted once with benzyl.

8. The compound of claim 1, wherein said compound has the structure:

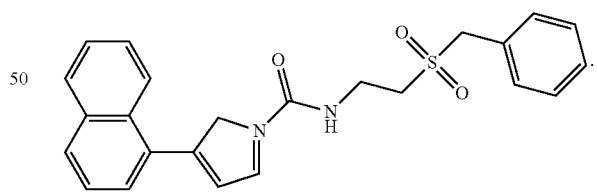

9. A compound of Formula II:

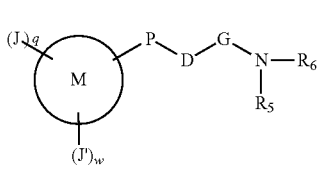

(II)

wherein,

Ring M, J, J', q, and w form

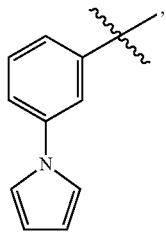

wherein J' is pyrrolyl, w is 1, and q is 0;

P is a bond;

D is absent;

G is C=O; and

R$_5$ and R$_6$ are taken together with the nitrogen to which they are attached to form a morpholinyl ring, wherein said morpholinyl ring is substituted with aryl, and wherein said aryl is substituted 1 to 3 times, in each instance, with branched or linear alkyl, alkoxy, or haloalkoxy; or a pharmaceutically acceptable salt thereof.

10. The compound of claim 9, wherein R$_5$ and R$_6$ are taken together with the nitrogen to which they are attached to form a morpholinyl ring, wherein said morpholinyl ring is substituted with phenyl, and wherein said phenyl ring is substituted 1 to 3 times, independently in each instance, with methoxy, difluoromethoxy, trifluoromethoxy, or methyl.

11. The compound of claim 10, wherein said morpholinyl ring is substituted once with phenyl, and wherein said phenyl ring is substituted once with difluoromethoxy.

12. The compound of claim 11, wherein said phenyl ring is substituted with difluoromethoxy in the meta position.

13. The compound of claim 12, wherein R$_5$ and R$_6$ are taken together with the nitrogen to which they are attached to form

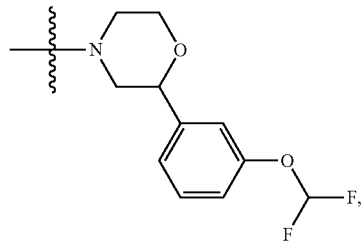 [SMILES: *N1CCOC(c2cccc(OC(F)F)c2)C1]

wherein ⸹ indicates the point of attachment to G.

14. The compound of claim 9, wherein the compound has the structure

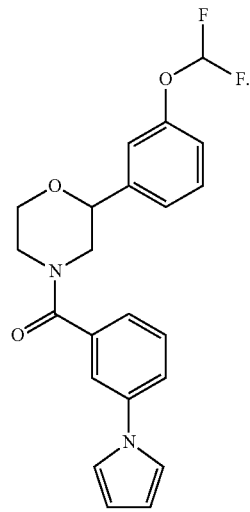 [SMILES: O=C(c1cccc(-n2cccc2)c1)N1CCOC(c2cccc(OC(F)F)c2)C1]

15. A pharmaceutical composition comprising a compound or pharmaceutically acceptable salt thereof of claim 1, and a carrier acceptable for human administration.

16. A pharmaceutical composition comprising a compound or pharmaceutically acceptable salt thereof of claim 9, and a carrier acceptable for human administration.

* * * * *